United States Patent

Varma et al.

[11] Patent Number: 5,264,455
[45] Date of Patent: Nov. 23, 1993

[54] SULFUR-SUBSTITUTED MEVINIC ACID DERIVATIVES

[75] Inventors: Ravi K. Varma, Vienna, Va.; Jeffrey O. Saunders, Acton, Mass.; Sam T. Chao, East Windsor, N.J.; Eric M. Gordon, Pennington, N.J.; Dinos P. Santafianos, Lawrenceville, N.J.

[73] Assignee: E. R. Squibb & Sons, Inc., Princeton, N.J.

[21] Appl. No.: 724,272

[22] Filed: Jul. 1, 1991

Related U.S. Application Data

[63] Continuation-in-part of Ser. No. 549,024, Jul. 6, 1990, abandoned.

[51] Int. Cl.⁵ .............. A61K 31/35; A61K 31/215; C07D 339/00
[52] U.S. Cl. .............. 514/459; 514/460; 514/529; 514/562; 514/574; 560/125; 562/501; 549/11; 549/21; 549/22; 549/39; 549/89; 549/90; 549/292
[58] Field of Search .............. 549/22, 11, 21, 39, 549/89, 90, 292; 514/436, 459, 460, 529, 562, 574; 560/125; 562/501

[56] References Cited

U.S. PATENT DOCUMENTS

| | | | |
|---|---|---|---|
| 3,983,140 | 9/1976 | Endo et al. | 260/343.5 |
| 4,049,495 | 9/1977 | Endo et al. | 195/36 |
| 4,231,938 | 11/1980 | Monaghan et al. | 260/343.5 |
| 4,346,227 | 8/1982 | Terahara et al. | 560/119 |
| 4,410,629 | 10/1983 | Terahara et al. | 435/146 |
| 4,444,784 | 4/1984 | Hoffman et al. | 424/279 |
| 4,448,979 | 5/1984 | Terahara et al. | 549/292 |
| 4,450,171 | 5/1984 | Hoffman et al. | 424/279 |

FOREIGN PATENT DOCUMENTS

| | | |
|---|---|---|
| 0065835 | 12/1982 | European Pat. Off. |
| 0137444 | 4/1985 | European Pat. Off. |
| 0251625 | 1/1988 | European Pat. Off. |
| 0306210 | 3/1989 | European Pat. Off. |
| 2075013A | 11/1981 | United Kingdom |

OTHER PUBLICATIONS

F. M. Singer et al., "New Inhibitors of in vitro Conversion of Acetate and Mevalonate to Cholesterol", Proc. Soc. Exper. Biol. Med., 102, 370 (1959).

F. H. Hulcher, "Inhibition of Hepatic Cholesterol Biosynthesis by 3,5-Dihydroxy-3,4,4-trimethylvaleric Acid and its Site of Action", Arch. Biochem. Biophys., 146, 422 (1971).

A. G. Brown et al., "Crystal and Molecular Structure of Compactin, a New Antifungal Metabolite from *Penicillium brevicompactum*", J. Chem. Soc. Perkin I. 1165-1170 (1976).

*Primary Examiner*—C. Warren Ivy
*Assistant Examiner*—A. Owens
*Attorney, Agent, or Firm*—Timothy J. Gaul

[57] ABSTRACT

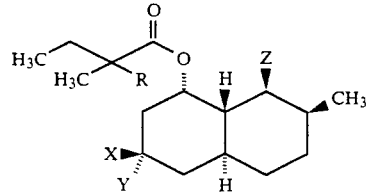

and pharmaceutically acceptable salts thereof possess activity as cell-selective HMG-CoA reductase inhibitors, thus making them useful as antihypercholesterolemic agents. In the above formula, X is hydrogen or $-S(O)_m-R^1$ and Y is hydrogen or $S(O)_n-R^2$, except that X and Y are not both hydrogen, or one of X and Y is $-S-$alkyl$-SH$ and the other is hydrogen;

Z is 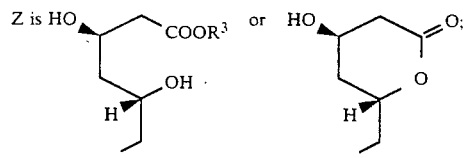

and the remaining symbols are as defined in the specification.

16 Claims, No Drawings

SULFUR-SUBSTITUTED MEVINIC ACID DERIVATIVES

CROSS-REFERENCE TO RELATED APPLICATION

This is a continuation-in-part of U.S. patent application Ser. No. 549,024, filed Jul. 6, 1990 now abandoned.

FIELD OF THE INVENTION

The present invention relates to sulfur-substituted mevinic acid derivatives, which are HMG-CoA reductase inhibitors useful as antihypercholesterolemic agents, and to methods of use for such compounds.

BRIEF DESCRIPTION OF THE INVENTION

In accordance with the present invention, compounds of the formula

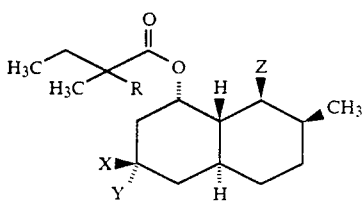

and pharmaceutically acceptable salts thereof possess activity as HMG-CoA reductase inhibitors, thus making them useful as antihypercholesterolemic agents. In formula I and throughout this specification, the above symbols are defined as follows:

X is hydrogen or $-S(O)_m-R^1$ and Y is hydrogen or $S(O)_n-R^2$, except that X and Y are not both hydrogen, or one of X and Y is $-S-$alkylene$-SH$ and the other is hydrogen;

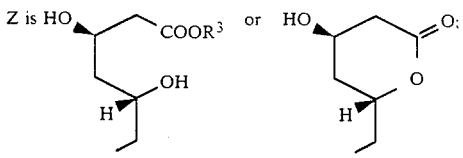

R is hydrogen, alkyl, cycloalkyl, aryl, or aralkyl;
$R^1$ and $R^2$ are each independently hydrogen, acyl, alkyl, alkenyl, alkynyl, aryl, aralkyl, alkaryl, cycloalkyl,

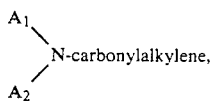

alkoxycarbonylalkylene, any of which is optionally substituted with 1, 2 or 3 hydroxy or halo groups (e.g., wherein $R^1$ and/or $R^2$ is trifluoromethyl) or $R^1$ and $R^2$ together are alkylene (i.e., forming a ring comprising the $S(O)_n$ and $S(O)_m$ groups and the carbon atom to which they are attached) of 1 to 6 carbon atoms;
$R^3$ is hydrogen, alkyl, ammonium, alkyl-ammonium, or alkali metal (such as Na, Li, or K);
$A_1$ and $A_2$ are each independently hydrogen, alkyl, aryl, aralkyl, or alkaryl;
m is 0, 1, or 2; and
n is 0, 1, or 2.

DETAILED DESCRIPTION OF THE INVENTION

Definition of Terms

Listed below are definitions of various terms used to describe this invention. These definitions apply to the terms as they are used throughout this specification (unless otherwise limited in specific instances) either individually or as part of a larger group.

The terms "alkyl", "alk" and "alkylene" include both straight and branched chain radicals of up to 12 carbons, preferably 1 to 8 carbons. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Exemplary alkylene groups are those derived from the foregoing exemplary alkyl groups (e.g., $-CH_2-$, $-CH_2CH_2-$). The terms "alkyl", "alk" and "alkylene" also include such groups having halo (such as F, Br, Cl or I or $CF_3$), alkoxy, hydroxy, thio, thioalkyl, aryl, alkyl-aryl, haloaryl, cycloalkyl, or alkylcycloalkyl substituents.

The term "alkenyl" by itself or as part of another group refers to both straight and branched chain groups having at least one double bond. Those groups having 2 to 10 carbon atoms are preferred. The term "alkenyl" further includes groups having halo, alkoxy, aryl, alkylaryl, haloaryl, cycloalkyl, or alkylcycloalkyl substituents.

The term "alkinyl" by itself or as part of another group refers to both straight and branched chain groups having at least one triple bond. Those groups having 2 to 10 carbon atoms are preferred. The term "alkinyl" further includes groups having halo, alkoxy, aryl, alkylaryl, haloaryl, cycloalkyl, or alkylcycloalkyl substituents.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, wherein such groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl, wherein the substituent on either the phenyl or naphthyl may be 1 or 2 lower alkyl groups, 1 to 5 halogens such as Cl, Br or F (1 to 7 halogens in the case of naphthyl), and/or 1 or 2 lower alkoxy groups.

The term "halogen" or "halo" refers to fluorine, chlorine, bromine and iodine, as well as trifluoromethyl.

The term "acyl" refers to all organic moieties that may be derived from an organic acid (i.e., a carboxylic acid) by exchange of the hydroxyl group; i.e., compounds of the partial formula $$O-\overset{O}{\underset{\|}{C}}-R^5$$

wherein $R^5$ is alkyl, aryl, aralkyl, amino, dialkylamino, alkylarylamino, diarylamino, alkoxy, cycloalkyl, aryloxy, alkenyl, cycloalkenyl, cyclohexadienyl, or alkyl, alkenyl, or aryl substituted with one or more halogen, cyano, nitro, mercapto, alkylthio or cyanomethylthio groups.

The compounds of this invention form basic salts with inorganic and organic bases. These salts are included within the language "pharmaceutically acceptable salts" and are within the scope of this invention. Such salts include ammonium salts, alkali metal salts, alkaline earth metal salts, and salts with organic bases such as dicyclohexylamine, benzathine, N-methyl-D-gluccamine, hydroamine and the like.

Some compounds of this invention are pictured as acids. They can also exist, however, as zwitterions (internal or inner salts), and these are also included within the language "pharmaceutically acceptable salts" and the scope of this invention.

Preferred Moieties

Preferred compounds of formula I are those wherein:
R is hydrogen or alkyl (methyl most preferred);

Z is 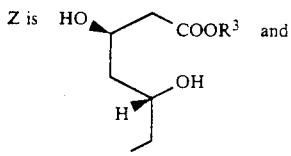 and $R^3$ is hydrogen or alkali metal (lithium most preferred).

Also preferred are those compounds of formula I wherein at least one of $S(O)_m-R^1$ and $S(O)_n-R^2$ are $C_{1-4}$ alkylthio, $C_{1-4}$ alkylsulfinyl, $C_{1-4}$ alkylsulfonyl, phenylthio, phenylsulfinyl, phenylsulfonyl, or mercapto. In another preferred compound of formula I, $S(O)_m-R^1$ and $S(O)_n-R^2$ are, together with the carbon atom to which they are attached,

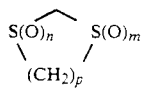

wherein p is 2, 3, or 4.

Use and Utility

The compounds of formula I will be formulated with a pharmaceutical vehicle or diluent. The pharmaceutical composition can be formulated in a classical manner with solid or liquid vehicles or diluents and pharmaceutical additives appropriate to the desired mode of administration. The compounds can be administered by an oral route (e.g., tablets, capsules, granules or powders) or a parenteral route (e.g., injectable preparations).

A typical capsule for oral administration contains active ingredients (25 mg), lactose (75 mg) and magnesium stearate (15 mg). The mixture is passed through a 60-mesh sieve and packed into a No. 1 gelatin capsule.

A typical injectable preparation is produced by aseptically placing 25 mg of a water-soluble salt of sterile active ingredient into a vial, asceptically freeze-drying and sealing. For use, the contents of the vial are mixed with 2 ml of physiological saline, to produce an injectable preparation.

The compounds of the invention are inhibitors of 3-hydroxy-3-methylglutaryl coenzyme A (HMG-CoA) reductase and inhibit cholesterol biosynthesis. An important property of the compounds of the present invention is that they act more selectively in the cells of the target organ (liver) than in the cells of other organs or tissues.

Such compounds are useful in treating atherosclerosis to inhibit progression of disease, in treating hyperlipidemia to inhibit development of atherosclerosis, and in treating nephrotic hyperlipidemia. In addition, the compounds of the invention increase plasma high density lipoprotein cholesterol levels. As HMG-CoA reductase inhibitors, the compounds of the invention may also be useful in inhibiting formation of gallstones and in treating tumors.

The compounds of the present invention may also be useful as anti-cancer agents by inhibiting the growth of tumors.

The compounds of the present invention may also be employed in combination with antihyperlipoproteinemic agents, such as probucol, and/or with one or more serum cholesterol lowering agents such as Lopid ® (gemfibrozil), bile acid sequestrants such as cholestyramine, colestipol, DEAE-Sephadex ® as well as clofibrate, nicotinic acid and its derivatives, neomycin, p-aminosalicylic acid, lovastatin, pravastatin, visinolin (velostatin, symvastatin or sinvinolin) and the like, and/or one or more squalene synthetase inhibitors.

The above compounds to be employed in combination with the HMG-CoA reductase inhibitor of the invention will be used in amounts as indicated in the Physicians' Desk Reference (PDR).

The dose to be administered depends on the unitary dose, the symptoms, and the age and the body weight of the patient. A dose for adults is preferably between 20 and 2,000 mg per day, which can be administered in a single dose or in the form of individual divided doses from 1-4 times per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis.* For those utilities they are admixed with suitable formulating agents, powders, emulsifying agents or solvents (such as aqueous ethanol) and sprayed or dusted on the plants to be protected.

In addition, the compounds of the invention may also be useful in elevating HDL-cholesterol levels while lowering levels of LDL-cholesterol and serum triglycerides.

Process of Preparation

Compounds of formula I can be prepared by the following exemplary process.
Preparation of the compound

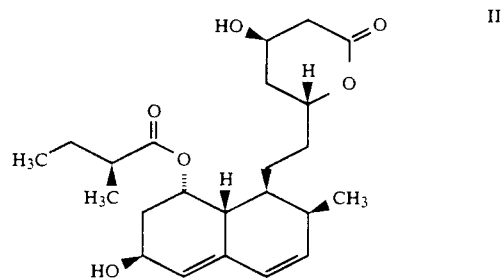

is described in U.S. Pat. Nos. 3,983,140 and 4,346,227. In the process of forming compound I, compound II is placed in an inert solvent (e.g., tetrahydrofuran or dichloromethane) under an inert atmosphere (e.g., argon or nitrogen) at a temperature of about 15° to 250° C. and treated with an appropriate silyl protecting agent (e.g., t-butyldimethylsilyl chloride, triethylsilyl chloride, or phenyldimethylsilyl chloride) in the presence of an appropriate amine base (e.g., imidazole) to form

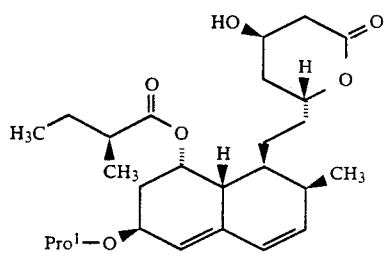

III wherein Pro¹ is a silyl oxygen-protecting group such as

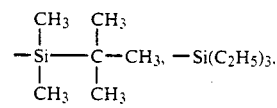

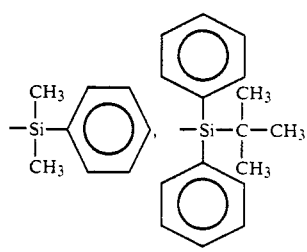

and the like.

Compound III is hydrogenated (e.g., with hydrogen gas) in an organic solvent (e.g., ethyl acetate) in the presence of a catalyst (e.g., platinum on carbon) to form a compound of the formula

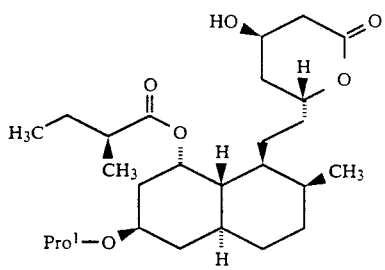

IV

Compound IV is treated with a base (e.g., potassium hydroxide) in a mixture of water and an organic solvent such as toluene (optionally containing some methanol) to form the potassium salt

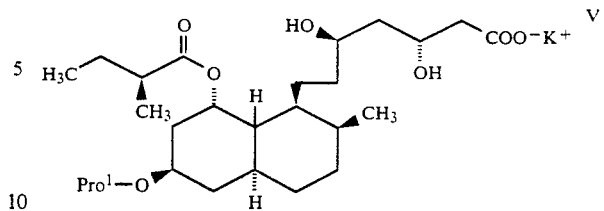

V

The potassium salt V is reacted in an organic solvent such as tetrahydrofuran with an organic base (e.g., pyrrolidine or piperidine) and n-butyllithium and an alkylating agent (e.g., iodomethane) in an inert atmosphere (e.g., argon) at about −60° to −20° C. (See European Patent Application 137,444). The resulting product is acidified, isolated and heated to about 100°-110° C. in an organic solvent (e.g., toluene) to form

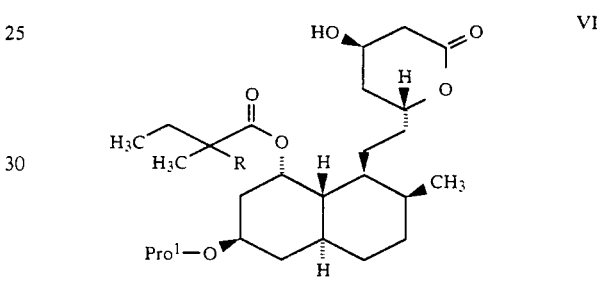

VI in which R is alkyl.

Compound VI is oxygen-protected by, for example, reaction with a protecting agent (e.g., benzyl bromomethyl ether), in the presence of an amine base (e.g., N,N-dimethylaniline) in an organic solvent (e.g., methylene chloride) to form

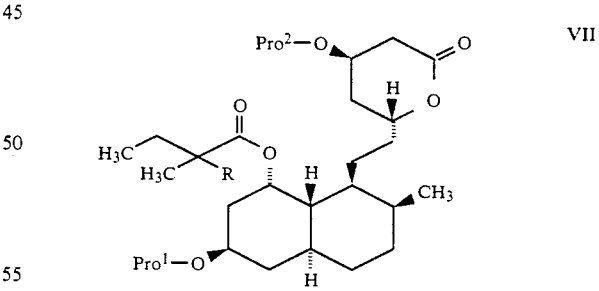

VII wherein Pro² is a different protecting group from Pro¹ and may be selected from benzyloxymethyl (which is preferred), p-methoxybenzyloxymethyl, tetrahydrylpyranyloxy, lower acyl and the like.

Pro¹ can then be removed by, for example, reaction with a deprotecting agent (e.g., hydrogen fluoride-pyridine) at about −10° to 10° C. under an inert atmosphere (e.g., nitrogen) in an inert solvent (e.g., acetonitrile) to form

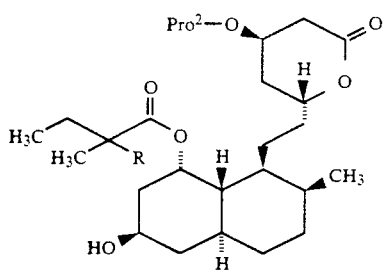

VIII

Compound VIII is reacted with an oxidizing agent (Dess-Martin periodinane preferred) in an organic solvent (e.g., methylene chloride, tert-butyl alcohol) at about 0° to 25° C. to form the ketone

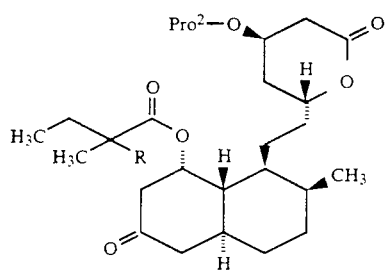

IX

Ketone IX is reacted with a monothiol or dithiol in the presence of an acid (e.g., acetic acid) and a Lewis acid catalyst (e.g., borontrifluoride etherate) in an organic solvent (e.g., methylene chloride) at about 20° to 30° C. to form the hydroxy-protected thioketals

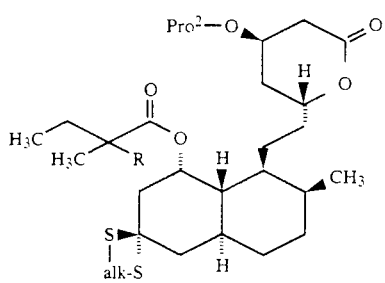

X in which "alk" is alkylene, and

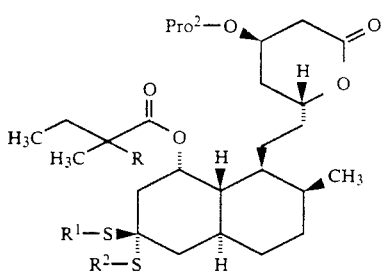

XI

Alternatively, ketone IX is first deprotected (e.g., by hydrogen gas treatment) in an organic solvent (e.g., ethyl acetate) in the presence of a catalyst (e.g., palladium hydroxide on carbon) at about 20° to 30° to form

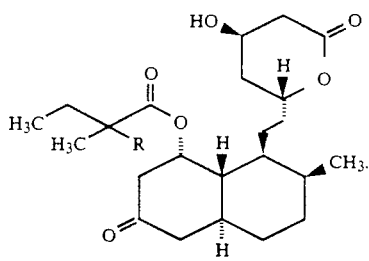

XII

Compound XII is reacted with a monothiol or dithiol as described above (compound IX→compounds X or XI) to form the formula I compounds having the more specific formulas

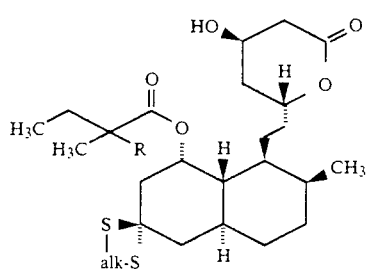

I(A)

and

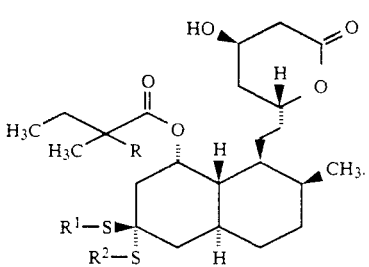

I(B)

Compounds I(A) and I(B) may be oxidized with, for example, 1.0, 2.0, or 4.0 molar amounts of a peroxide or peracid (e.g., m-chloroperoxybenzoic acid for consistancy) in an organic solvent (e.g., methylene chloride) or solvent mixture (e.g., methylene chloride-methanol) at about −78° to 0° C. to form either the monosulfoxides

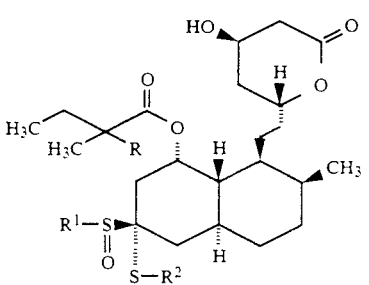

I(C)

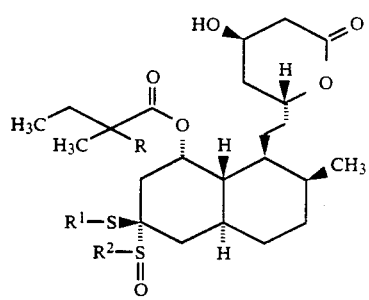

or a disulfoxide

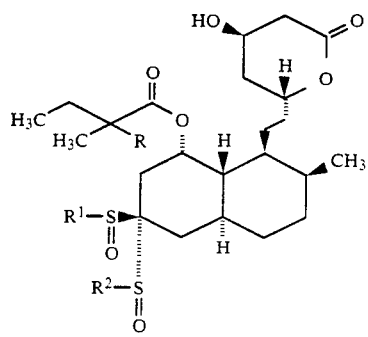

or a disulfone

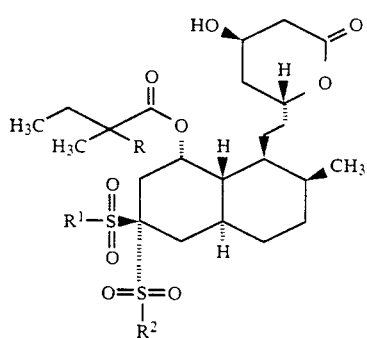

Compound I(B) may be reduced under free-radical reduction conditions to form

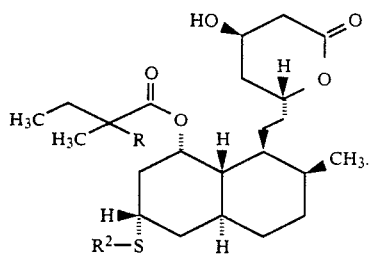

The preferred reduction reaction uses tri-n-butyltin hydride in the presence of a free radical initiator (e.g., azabisisobutyronitrile) in refluxing benzene.

When compound I(A) is treated under these free-radical reduction conditions, it forms the compound

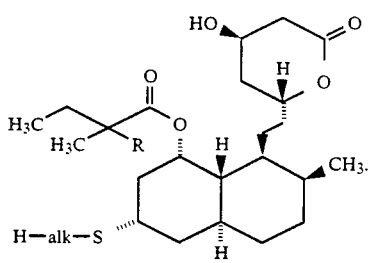

Compound I(G) may be oxidized by, for example, one or two molar equivalents of a peroxide or peracid (e.g., m-chloroperoxybenzoic acid) in an organic solvent (e.g., methylene chloride) or solvent mixture (methylene chloride-methanol) at about −78° to 0° C. to form a monosulfoxide

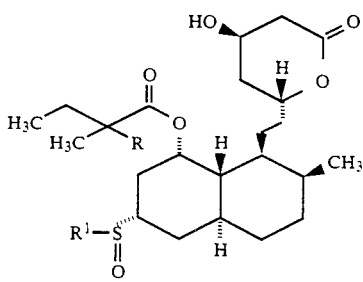

or a monosulfone

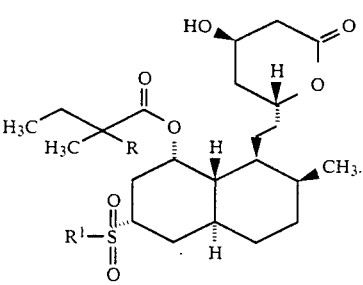

The following alternative exemplary process is useful in preparing compounds wherein $R^1$ and/or $R^2$ is hydrogen or acyl.

Compound III may be hydrogenated in an organic solvent (e.g., ethyl acetate) in the presence of a catalyst (e.g., platinum on activated carbon) to yield a compound of the formula

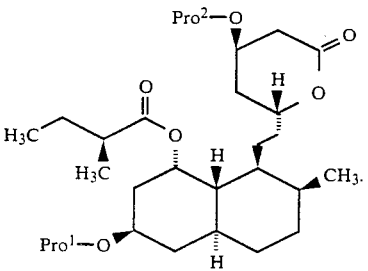

Compound XIII may be treated with a hydride reducing agent, such as diisobutylaluminum hydride (DIBAL), under an inert atmosphere (e.g., argon) at about −78° C. in an organic solvent (e.g., tetrahydrofuran) to yield a compound of the formula

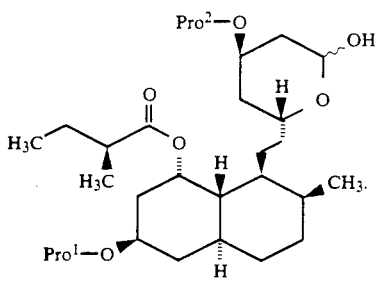

XIV

An appropriate vinyl ether (e.g., 2-methoxypropene) may be added to a solution of compound XIV, followed by treatment with an acid catalyst such as pyridinium p-toluene sulfonate (PPTS) in an organic solvent (e.g., methylene chloride) at about 0° C. under an inert atmosphere (e.g., argon). The result is a compound of the formula

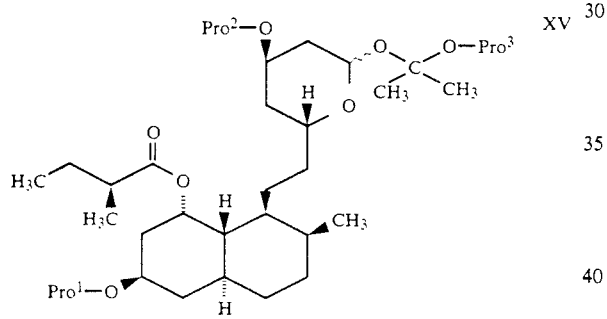

XV wherein $Pro^3$ is an alkyl group, such as methyl.

Compound XI is treated with an aqueous alkali metal hydroxide (e.g., LiOH) in an organic solvent (e.g., dioxane) to form

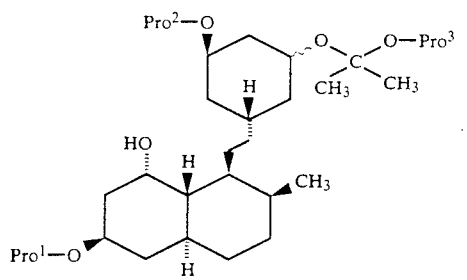

XVI

Compound XVI is then reacted with an oxidizing agent (Dess-Martin periodinane preferred) in an organic solvent (e.g., methylene chloride, tert-butyl alcohol) at about ambient temperature to form

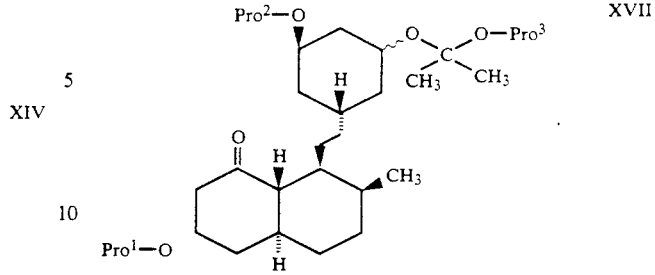

XVII

Compound XVII, in turn, is treated with a catalyst such as 1,8-diazabicyclo-[5,4,0]undec-7-ene (DBU) in an organic solvent (e.g., tetrahydrofuran) at about 70° to 90° C. and heated to about 80° to 135° C. to form

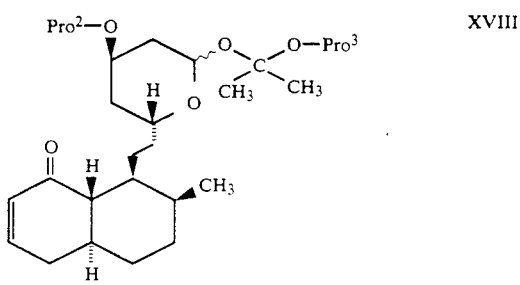

XVIII

The enone XVIII is reacted with a base (e.g., triethylamine) and a thiol acid (e.g., thiolacetic acid, thiobenzoic acid) in an organic solvent (e.g., trichloromethane) at about −10° to 35° C. to form

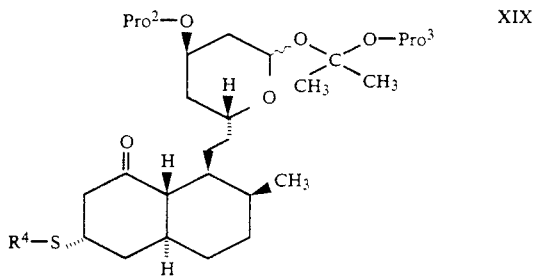

XIX wherein $R^4$ is acyl.

Compound XIX is treated with a hydrogenating agent such as lithium tri-t-butoxyaluminum hydride $(Li(O-t-Bu)_3AlH)$ in an organic solvent (e.g., tetrahydrofuran) under an inert atmosphere (e.g., argon) to form

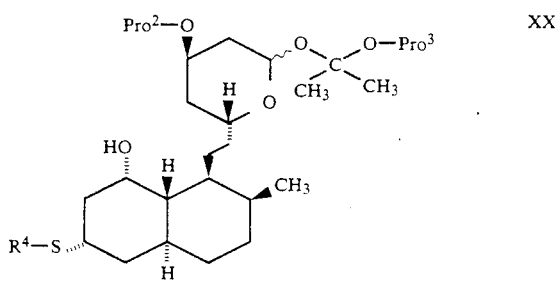

XX

Compound XX, in turn, is reacted with an organic acid (e.g., acetic acid) in an aqueous and organic solvent mixture (e.g., water-tetrahydrofuran) at about 0° to 35° C. to form

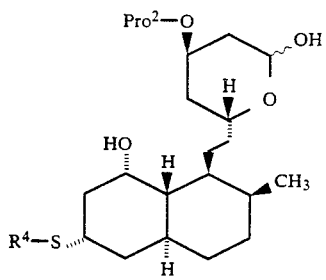

Compound XXI is treated with a Grignard reagent (e.g., phenylmagnesium bromide) in an organic solvent (e.g., tetrahydrofuran) at about −30° to 0° C. in an inert atmosphere (e.g., argon), followed by treatment with an oxidizing agent such as 1,1'-(azodicarbonyl)dipiperidine to form

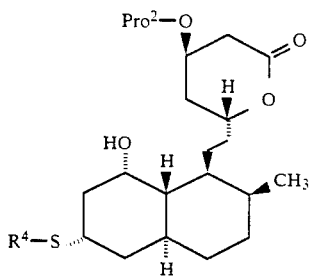

Compound XXII is then acylated with, for example, 2,2-dimethylbutyryl chloride in an organic solvent (e.g., pyridine) in the presence of a catalytic base such as dimethylaminopyridine (DMAP) at about 60° to 90° C. to form

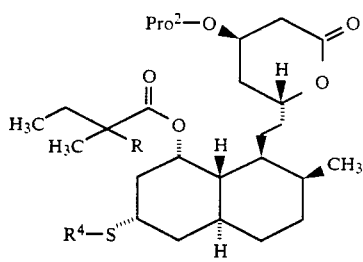

Compound XXIII is oxygen-deprotected with, for example, hydrogen fluoride-pyridine in an organic solvent (e.g., acetonitrile) at about −10° to 10° C. to form the compounds of formula I having the more specific formula

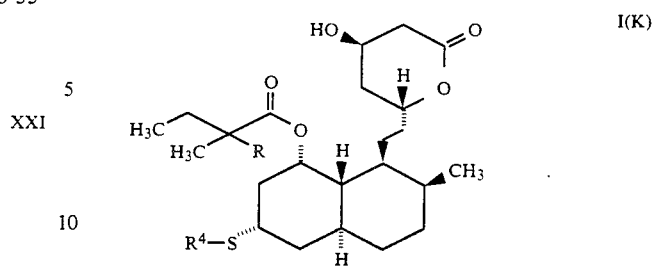

Alternatively, compound VIII is treated with an acylating agent (e.g., diisopropylazadicarboxylate), a thio acid (e.g., thiolacetic acid), and triphenylphosphine in an organic solvent (e.g., tetrahydrofuran) at about 0° to 25° C., followed by deprotection (e.g., by $H_2$ balloon) to form compound I(K).

When compound I(K) is treated with a base (e.g., NaOH) at about −10° to 10° C. in an inert solvent (e.g., dioxane), compound I having the specific formula

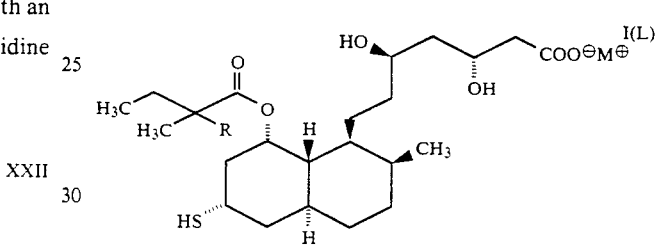

is formed, wherein M⊕ is alkali metal or ammonium.

Compound I wherein Z is the lactone, such as compounds I(A-K) above, may be converted to the open-chain form by hydrolysis with an aqueous ammonium or alkali metal base (e.g., lithium hydroxide) at about 20° to 30° C. in an inert solvent (e.g., tetrahydrofuran). $R^3$ can be converted to hydrogen by treatment with a mild aqueous acid (e.g., potassium bisulfate). Compound I may be conventionally esterified to form compounds wherein $R^3$ is alkyl.

Conversely, compound I wherein Z is the open chain acid such as compound I(L) above wherein M⊕ is hydrogen, may be converted to the lactone by, for example, either heating in toluene to about 100° to 135° C. or treating with a catalytic amount of trifluoroacetic acid at about ambient temperature in an organic solvent (e.g., tetrahydrofuran).

The following working examples represent preferred embodiments of the invention and are illustrative rather than limiting. Unless otherwise specified, all temperatures are in degrees Celsius (° C.). The preparation of each compound appears below its name. As a shorthand reference, the compound prepared in part 1-A will be called ¢Compound 1-A" or "intermediate 1-A" and so forth for all compounds hereafter.

EXAMPLE 1

[1S-[1α,4aα,7β,8β(2S*,4S*),8aβ]]-2,2-Dimethyl-butanoic acid, 3,3-bis(methylthio)decahydro-7-methyl-8-[2-(tetrahydro-4-hydroxy-6-oxo-2H-pyran-2-yl)ethyl]-1-naphthalenyl ester 1-A. [1S-[1α(R*),3β,4β,7β,8β(2S*,4S*),8aβ]]-2-Methylbutanoic acid, 3-[[(1, 1-dimethylethyl)dimethylsilyl]oxy]-1,2,3,7,8,8a-hexahydro-7-methyl-8-[2-(tetrahydro-4-hydroxy-6-oxo-2H-pyran-2-yl)ethyl]-1-naphthalenyl ester The starting material for preparation of intermediate A was [1S-[1α(R*),3β,4β,7β,8β(2S*, 4S*),8aβ]]-2-methylbutanoic acid, 3-hydroxy-1,2, 3,7,8,8a-hexahydro-7-methyl-8-[2-(tetrahydro-4-hydroxy-6-oxo-2H-pyran-2-yl)ethyl]-1-naphthalenyl ester. Preparation of this starting material has been described in U.S. Pat. Nos. 3,983,140 and 4,346,227.

A solution of 8.43 g (20.7 mmol, 1.00 eq.) of the starting material in 80 ml of dry tetrahydrofuran under argon at ambient temperature was treated with 1.76 g (25.9 mmol, 1.25 eq.) of imidazole, followed by 3.44 g (22.8 mmol, 1.10 eq.) of t-butyldimethylsilyl chloride. A white precipitate formed almost immediately (5–10 sec). After stirring for 26 hours, the reaction mixture was diluted with 80 ml of ether, filtered and concentrated in vacuo. Purification of the residue by flash chromatography (with Merck silica gel; 40% ethyl acetate in hexanes) gave 7.41 g (a 69% yield) of the mono-silylated product (intermediate 1-A) as a white solid, with a melting point of 111° to 115° C. More typical yields for this conversion are in the range of 80 to 85%. Lowering the temperature of the reaction or slowly adding a solution of t-butyldimethyl silyl chloride in tetrahydrofuran improves the yield somewhat.

1-B. [1S-[1α(R*),3β,4aα,7β,8β(2S*,4S*),8aβ]]-2-Methylbutanoic acid,3-[[(1,1-dimethylethyl)dimethylsilyl]oxy]decahydro-7-methyl-8-[2-(tetrahydro-4-hydroxy-6-oxo-2H-pyran-2-yl)ethyl]-1-naphthalenyl ester To a degassed, argon-purged-solution of 9.38 g (18.0 mmol) of Compound 1-A in 200 ml of ethyl acetate was added 1.4 g of 10% platinum on carbon. This suspension was subjected to 50 psi of H$_2$ in a consumption of starting material with generation of the desired product and some desilylated product. The filtered reaction mixture was concentrated and the products were isolated by flash chromatography. Elution with 45% hexanes in ethyl acetate gave 7.73 g (82%) of compound 1-B as a clear glass and elution with 30% hexanes in ethyl acetate gave 0.98 g (13%) of desilylated product.

1C. [1S-[1α(R*),3β,4aα,7β,8β(2S*,4S*),8aβ]]-2,2-Dimethylbutanoic acid,3-[[(1,1-dimethylethyl)dimethylsilyl]oxy]decahydro-7-methyl-8-[2-(tetrahydro-4-hydroxy-6-oxo-2H-pyran-2-yl)ethyl]-1-naphthalenyl ester A solution of compound 1-B (10.5 g, 20.04 mmol) in a mixture of toluene (200 mL) and methanol (42 mL) was treated with 1.0 N potassium hydroxide (20 mL) at room temperature under an atmosphere of nitrogen for 45 minutes. The solvent was evaporated in vacuo to give a gum. This gum was azeotroped with benzene (250 mL) and then dried in vacuo at 45° (oil bath temperature) overnight to give a foamy solid.

To a chilled (−55°, acetonitrile-dry ice bath) and stirred solution of the above solid in dry tetrahydrofuran (150 mL) under an atmosphere of nitrogen was added dry pyrrolidine (6.48 mL, 77.63 mmol), followed by U-butyllithium (2.5M in hexane, 27.84 mL, 69.6 mmol). The mixture was gradually warmed up to −25° (carbon tetrachloride-dry ice bath) and stirred for 2.5 hours. Iodomethane (3.12 mL, 50.12 mmol) was added dropwise. After 1.0 hour, a small aliquot was worked up. $^1$H-NMR spectrum indicated there was 15–20% non-methylated starting material present. Therefore, the mixture was recooled to −55°, more dry pyrrolidine (3.24 mL) and n-butyllithium (2.5M in hexane, 13.92 mL) were added, and the mixture was warmed up to −25+. After 2.5 hours, iodomethane (1.56 mL) was added and the mixture was stirred for another hour. The resulting mixture was quenched with 10% potassium bisulfate solution (100 mL) at −25°, warmed up to room temperature, saturated with sodium chloride and extracted with ethyl acetate (3×100 mL). The combined ethyl acetate extracts were washed with a small amount of 5% sodium bicarbonate and brine, dried over anhydrous sodium sulfate and evaporated in vacuo to give a gummy residue (11.0 g).

The above gum was refluxed in dry toluene (200 mL) under an atmosphere of nitrogen for 4.0 hours. The solvent was then evaporated in vacuo to give a gummy material. This gum was chromatographed on a column of silica gel (LPS-1, 450 g), eluting with ethyl acetate-hexane (1:3) to give 7.3 g (67.5%) of Compound 1-C as a gum with consistent $^1$H-NMR and $^{13}$C-NMR spectra.

1-D. [1S-[1α(R*),3β,4aα,7β,8β(2S*,4S*),8aβ]]-2,2-Dimethylbutanoic acid,3-[[(1,1-dimethylethyl)dimethylsilyl]oxy]decahydro-7-methyl-8-[2-[tetrahydro-4-[(phenylmethoxy)methoxy]-6-oxo-2H-pyran-2-yl]-ethyl]-1-naphthalenyl ester To a chilled (0°, ice bath) and stirred solution of Compound 1-C (7.3 g, 13.52 mmol) in dry dichloromethane (80 mL) under an atmosphere of nitrogen was added dry N,N-dimethylaniline (3.7 g, 30.53 mmol). After 15 minutes, benzyl bromomethyl ether (5.62 g, 26.13 mmol) was added. The resulting solution was gradually warmed up to room temperature and stirred for 20 hours. The solvent was partially removed in vacuo. Ethyl acetate (300 mL) was added. The ethyl acetate solution was washed with a 10% potassium bisulfate solution, a saturated sodium bicarbonate solution and brine, dried over anhydrous sodium sulfate and evaporated in vacuo to give an oil. This oil was chromatographed on a column of silica gel (LPS-1, 300 g), eluting with ethyl acetate-hexane (1:9) to give 8.5 g (95.4%) of Compound 1-D as an oil with consistent $^1$H-NMR and $^{13}$C-NMR spectra.

1-E. [1S-[1α(R*),3β,4aα,7β,8β(2S*,4S*),8aβ]]-2,2-Dimethylbutanoic acid, 3-hydroxydecahydro-7-methyl-8-[2-[tetrahydro-4-[(phenylmethoxy)methoxy]-6-oxo-2H-pyran-2-yl]-ethyl]-1-naphthalenyl ester A solution of Compound 1-D (8.5 g, 12.9 mmol) in dry acetonitrile (100 mL) was cooled to 0° (ice bath) under an atmosphere of nitrogen and treated with two 4 mL portions of hydrogen fluoride-pyridine over 1.5 hours. The reaction mixture was diluted with ethyl acetate (200 mL), washed with a 10% potassium hydrogen sulfate solution, brine and a dilute sodium bicarbonate solution, dried over anhydrous sodium sulfate and evaporated in vacuo to give a gum. This gum was chromatographed on a column of silica gel (Baker 60–200 mesh, 300 g), eluting with ethyl acetate-hexane (35:65 and 1:1) to give 6.0 g (85.4%) of Compound 1-E as a solid (m.p. 73°–77°) with consistent $^1$H-NMR and $^{13}$C-NMR spectra.

1-F.
[1S-[1α(R*),3β,4aα,7β,8β(2S*,4S*),8aβ]]-2,2-Dimethylbutanoic acid,
3-oxodecahydro-7-methyl-8-[2-[tetrahydro-4-[(phenylmethoxy)methoxy]-6-oxo-2H-pyran-2-yl]-ethyl]-1-naphthalenyl ester To a stirred suspension of Dess-Martin periodinane (514 mg, 1.212 mmol) in dichloromethane (5 ml) at room temperature under an atmosphere of nitrogen was added dropwise a solution of Compound 1-E (600 mg, 1.102 mmol) in dichloromethane (10 ml) followed by t-butyl alcohol (114 µl, 1.212 mmol). After 1.5 hours, the mixture was poured into a stirred mixture of sodium bicarbonate (500 mg) in 0.5M sodium thiosulfate (10 ml) and dichloromethane (75 ml). The mixture was stirred vigorously until the two layers were clear. The dichloromethane layer was separated, washed with brine, dried over anhydrous sodium sulfate and evaporated in vacuo to give a gum. This gum was flash-chromatographed on a column of silica gel (LPS-1, 40 g), eluting with ethyl acetate-hexane (3:7) to give 455 mg (76.1%) of compound 1-F as a gum with consistent $^1$H-NMR and $^{13}$C-NMR spectra.

1-G.
[1S-[1α(R*),3β,4aα,7β,8β(2S*,4S*),8aβ]]-2,2-Dimethylbutanoic acid,
3-oxodecahydro-7-methyl-8-[2-(tetrahydro-4-hydroxy-6-oxo-2H-pyran-2-yl)ethyl]-1-naphthalenyl ester A slow stream of hydrogen was bubbled through a solution of Compound 1-F (60 mg, 0.111 mmol) in ethyl acetate (6 ml) containing 20% palladium hydroxide on carbon (60 mg) and glacial acetic acid (1 drop). After 2 hours, the mixture was filtered through a bed of Celite® and was washed with small amounts of ethyl acetate. The filtrate and washings were combined and evaporated in vacuo to give a gum. This gum was chromatographed on a column of silica gel (Baker 60-200 mesh, 15 g), eluting with ethyl acetate-dichloromethane (20:80 and 30:70) to give 35 mg (77.2%) of Compound 1-G with consistent $^1$H-NMR spectra. Another run using Compound 1-F (340 mg) gave 225 mg more of Compound 1-G.

1-H. [1S-[1α,4aα,7β,8β(2S*,4S*),8aβ]]-2,2-Dimethylbutanoic acid, 3,3-bis(methylthio)-decahydro-7-methyl-8-[2-(tetrahydro-4-hydroxy-6-oxo-2H-pyran-2-yl)ethyl]-1-naphthalenyl ester To a chilled (ice bath) and stirred solution of Compound 1-G (102 mg, 0.25 mmol) in a mixture of dichloromethane (1.0 ml) and glacial acetic acid (1.0 ml) under an atmosphere of nitrogen was added a solution of methyl mercaptan (48 mg, 1.0 mmol) in methylene chloride (0.5 ml) followed by boron trifluoride etherate (31 µl, 0.25 mmol). After 2 hours at 0° C., water (10 ml) was added and the mixture was extracted with ethyl acetate (3×10 ml). The combined ethyl acetate extracts were washed with brine, dried over anhydrous sodium sulfate and evaporated in vacuo to give a gum. This gum was chromatographed on a column of silica gel (Baker 60-200 mesh, 20 g), eluting with ethyl acetate (4:6) to give 65 mg (53.4%)[1] of Compound 1-H with consistent $^1$H-NMR and $^{13}$C-NMR spectra. Another run using Compound 1-G (150 mg) gave 85 mg more of Compound 1-H (Example 1). Melting point: 150°-151° C.

EXAMPLE 2

[1S-[1α(βS*,ΔS*),2α,4aβ,8β,8aβ]]-8-(2,2-dimethyl-1-oxobutoxy)decahydro-β,α-dihydroxy-2-methyl-6,6-bis(methylthio)-1-naphthaleneheptanoic acid, monolithium salt A stirred solution of Example 1 (125 mg, 0.257 mmol) in tetrahydrofuran (3 ml) at room temperature under an atmosphere of nitrogen was treated with 1.0 N lithium hydroxide (514 µl, 0.514 mmol). After 30 minutes, the solvent was mostly evaporated by a stream of nitrogen to leave a gummy residue. This residue was dissolved in 10% methanol-water and chromatographed on a column of HP-20 (1.5"×1" column bed), eluting with deionized, distilled water (300 ml) and 75% methanol-water (300 ml) to give in the later eluate thin layer chromatography (TLC)-homogeneous Example 2. This eluate was evaporated in vacuo and lyophilized overnight to give 65 mg (48.2%) of a hydrated analytical specimen of Example 2 (as a white solid with consistent IR, Mass and $^1$H-NMR spectral data.

Analysis for $C_{26}H_{45}O_6S_2 \cdot Li \cdot 0.3\ H_2O$ (MW=530.11): Calc'd: C,58.91; H,8.67; S,12.10; Found: C,58.88; H,8.94; S,11.80.

IR (KBr): 3435 cm$^{-1}$ (OH), 1717, 1702 cm$^{-1}$ (c=O, ester), 1576 cm$^{-1}$ (c=O, acid salt).

Mass Spectrum: $(M-H)^- = 517$, $(M+Li)^+ = 525$, $(M+Li-2H)^- = 523$, $(M+2Li-H)^+ = 531$, $(M+3Li-2H)^+ = 537$.

$^1$H-NMR Spectrum (D$_2$O, 270 MHz): δ0.81 (t+d,6H,C$\underline{H}_3$+CH$_2$C$\underline{H}_3$) 1.16 (s,3H,C$\underline{H}_3$) 1.17 (s,3H,C$\underline{H}_3$) 1.93 (s,3$\underline{H}$,SCH$_3$) 2.01 (s,3H,SC$\underline{H}_3$) 2.35 (m,2H,C$\underline{H}_2$C=O) 3.60 (m,1H,C$\underline{H}$OH) 4.05 (m,1H,C$\underline{H}$OH) 5.06 (s,1H,C$\underline{H}$-O)ppm.

EXAMPLE 3

[1S-[1α,4aα,7β,8β(2S*,4S*),8aβ]-2,2-Dimethylbutanoic acid,
3-spiro(1,3-dithiolanyl)-decahydro-7-methyl-8-[2-(tetrahydro-4-hydroxy-6-oxo-2H-pyran-2-yl)ethyl]-1-naphthalenyl ester To a chilled (ice bath) and stirred solution of compound 1-F (1.05 mg, 0.25 mmol) in a mixture of dichloromethane (0.5 ml) and glacial acetic acid (0.5 ml) under an atmosphere of argon was added 1,2-ethanedithiol (84 µl, 1.0 mmol), followed by borontrifluoride etherate (31 µl, 0.25 mmol). After 2 hours at 0°, brine (15 ml) was added and the mixture was extracted with ethyl acetate (3×15 ml). The combined ethyl acetate extracts were washed with brine, dried over anhydrous sodium sulfate and evaporated in vacuo to give a gum. This gum was chromatographed on a column of silica gel (Baker 60-200 mesh, 30 g), eluting with ethyl acetate-hexane (3:7) to give 100 mg (82.5%) of Example 3 with consistent H$^1$-NMR and C$^{13}$-NMR spectra. Another run using Compound 1-F (75 mg) gave more of Example 3.

EXAMPLE 4

[1'S-[1'α(βS*,ΔS*),2'α,4a'β,8'β,8a'α]]-8'-(2,2-Dimethyl-1-oxobutoxy)octahydro-β,Δ-dihydroxy-2'-methylspiro[1,3-dithiolane-2,6'(2'H)-naphthalene]-1'-heptanoic acid, monolithium salt A stirred solution of Example 3 (150 mg, 0.307 mmol) in tetrahydrofuran (4 ml) at room temperature under an atmosphere of argon was treated with 1.0 N lithium hydroxide (614 µl, 0.614 mmol). After 45 minutes, the solvent was mostly evaporated by a stream of nitrogen to leave a gummy residue. This residue was dissolved in 10% methanol-water and chromatographed on a column of HP-20 (1.5"×1.0" column bed), eluting with deionized, distilled water (300 ml) and 75% methanol-water (300 ml) to give in the later eluate TLC-homogeneous Example 4. This eluate was evaporated in vacuo and lyophilized overnight to give 95 mg (58.8%) of a hydrated analytical specimen of Example 4 as a white solid with consistent IR, mass and $H^1$-NMR spectral data.

Analysis for $C_{26}H_{43}O_6S_2.Li.0.6H_2O$ (M.W.=533.50): Calc'd: C,58.54; H,8.35; S,12.02; Found: C,58.68; H,8.36; S,11.73.

IR(KBr): 3454 cm$^{-1}$(OH), 1716 cm$^{-1}$(C=O,ester), 1587 cm$^{-1}$ (C=O, acid salt). Mass: $(M+Li)^+=523$, $(M+2Li-H)^++Li=529$, $(M-H)^-=515$, $(M-2H+Na)^-=521$.

$H^1$-NMR Spectrum ($D_2O$, 270 MHz): δ0.78 (d,3H,CH$_3$) 0.81 (5,3H,CH$_3$) 1.21 (d,6H,CH$_3$) 3.23 and 3.33 (m,4H,—SCH$_2$CH$_2$S—) 3.51 (s broad,1H,C$\underline{H}$-OH) 4.05 (s broad,1H,C$\underline{H}$-OH) 5.13 (s,1H,C$\underline{H}$-O)ppm.

EXAMPLE 5

[1S-[1α,4aα,7β,8β(2S*,4S*),8aβ]]-2,2-Dimethyl-butanoic acid, 3,3-bis(propylthio)decahydro-7-methyl-8-[2-(tetrahydro-4-hydroxy-6-oxo-2H-pyran-2-yl)ethyl]-1-naphthalenyl ester To a chilled (−20°, dry ice-carbon tetrachloride bath) and stirred solution of Compound 1-F (53 mg, 0.125 mmol) in a mixture of dichloromethane (0.5 ml) and glacial acetic acid (0.5 ml) under an atmosphere of argon was added 1-propanethiol (45 µl, 0.5 mmol), followed by borontrifluoride etherate (15.3 µl, 0.125 mmol). A TLC examination after 1.5 hours at −20° showed the absence of compound 1-F and the presence of only one product. After 2 hours, the brine (15 ml) was added and the mixture was extracted with ethyl acetate (3×15 ml). The combined ethyl acetate extracts were washed with brine, dried over anhydrous sodium sulfate and evaporated in vacuo to give a gum. This gum was chromatographed on a column of silica gel (Baker 60-200 mesh, 30 g), eluting with ethyl acetate-hexane (3:7) to give 50 mg (71.8%) of Example 5 with consistent $H^1$-NMR and $C^{13}$-NMR spectra. Another run using compound 1-F (100 mg) gave 100 mg more of Example 5.

EXAMPLE 6

[1S-[1α(βS*,ΔS*),2α,4aβ,8β(R*),8aα]]-8-(2,2-Dimethyl-1-oxobutoxy)decahydro-β,Δ-dihydroxy-2-methyl-6,6-bis(propylthio)-1-naphthaleneheptanoic acid, monolithium salt A stirred solution of Example 5 (150 mg, 0.269 mmol) in tetrahydrofuran (4 ml) at room temperature under an atmosphere of argon was treated with 1.0 N lithium hydroxide (539 µl, 0.539 mmol). After 1.0 hour, the solvent was mostly evaporated by a stream of nitrogen to leave a gummy residue. This residue was dissolved in 10% methanol-water and chromatographed on a column of HP-20 (1.5"×1.0" column bed), eluting with deionized, distilled water (300 ml) and 75% methanol-water (300 ml) to give in the later eluate TLC-homogeneous Example 6. This eluate was evaporated in vacuo and lyophilized overnight to give 95 mg (60.8%) of a hydrated analytical specimen of Example 6 as a white solid with consistent IR, mass and $H^1$-NMR spectral data.

Analysis for $C_{30}H_{53}O_6S_2.Li.0.75H_2O$ (M.W.=594.32). Calc'd: C,60.64; H,9.24; S,10.79; Found: C,60.74; H,9.27; S,11.08.

IR(KBr): 3428 cm$^{-1}$(OH), 1713 cm$^{-1}$(C=O,ester), 1586 cm$^{-1}$ (C=O,acid salt). Mass Spectrum: $(M+Li)^+=581$, $(M+2Li)^+=587$ $(M-H)^-=573$, $(M-H)^-+Li=579$ $H^1$-NMR Spectrum ($D_2O$,270 MHz): δ0.80 (d,broad,3H,CH$_3$) 0.82 (t,broad,3H,CH$_3$) 0.95 (m,6H,SCH$_2$C$\underline{H}_2$CH$_3$) 1.19 (s,6H,CH$_3$) 3.59 (s,broad,1H,C$\underline{H}$—O$\underline{H}$) 4.07 (s,broad,1H,C$\underline{H}$—OH) 5.03 (s,broad,1H,C$\underline{H}$—O)ppm.

EXAMPLE 7

[1S-[1α,4aα,7β,8β(2S*,4S*),8aβ]]-2,2-Dimethyl-butanoic acid, 7-methyldecahydro-3-(methylsulfinyl)-3-(methylthio)-8-[2-(tetrahydro-4-hydroxy-6-oxo-2H-pyran-2-yl)ethyl]1-naphthalenyl ester A solution of Example 1 (1.50 mg, 0.30 mmol) in dichloromethane (5.0 ml) containing methanol (1.0 ml) was cooled and stirred in a dry ice-acetone bath at −78° and a solution of 90% m-chloroperoxybenzoic acid (56.8 mg, 0.3 mmol) in dichloromethane was added dropwise. The solution was then allowed to warm gradually to room temperature in the course of 3.0 hours. A TLC examination (silica gel, ethyl acetate) showed the complete absence of starting material, suggesting that sulfone formation did not occur. A slight excess of ethereal diazomethene was then added (in order to convert the acid into the methyl ester to facilitate purification), and after a few minutes, the mixture was concentrated in vacuo. The residual gum was subjected to chromatography on a column of Baker 60-200 mesh silica gel (15 g), eluting the column with dichloromethane, dichloromethane-ethyl acetate (1:1) and ethyl acetate-methanol (95:5) to afford Example 7 as a white foamy solid (139.3 mg, 90%). The $H^1$-NMR spectrum in CDCl$_3$ was consistent with the structure and showed that it was a mixture of two sulfoxide isomers in the approximate ratio 75:25. These were not readily separable by TLC. Attempts made to crystallize it from ethyl acetate-hexane and ether-hexane were unsuccessful.

EXAMPLE 8

[1S-[1α(βS*,ΔS*),2α,4aβ,8β,8aβ]]-8-(2,2-Dimethyl-1-oxobutoxy)decahydro-β,Δ-dihydroxy-2-methyl-6-(methylsulfinyl)-6-(methylthio)-1-naphthaleneheptanoic acid, monolithium salt A solution of Example 7 (140 mg, 0.271 mmol) in tetrahydrofuran (4.0 ml) was stirred under an atmosphere of nitrogen with 1.0 N LiOH (0.64 ml) at room temperature for 20 minutes. The mixture was then concentrated in vacuo to remove the tetrahydrofuran and was applied on a column of HP-20 (1.5"×1.0" column bed). The column was eluted with deionized distilled water (200 ml), followed by methanol-deionized distilled water (1:1, 320 ml). The latter eluate was concentrated in vacuo and lyophilized to afford a hydrated analytical specimen of Example 8 as a white electrostatic solid (128 mg, 85.3%) with consistent IR, mass and $H^1$-NMR spectral data.

Analysis for $C_{26}H_{45}O_7S_2Li.0.71H_2O$ (M.W. 553.50): Calc'd: C,55.66; H,8.30; S,11.89, Li,1.29%; Found: C,55.70; H,8.47; S,11.84; N,0.09%.

IR Spectrum (KBr): μmax 3430 (strong,OH),1719 (strong c=O), 1588 (strong,COOLi), 1150 (strong,S=O?), ~1040 (strong,S=O)cm$^{-1}$ etc.

H-NMR Spectrum (D$_2$O,270 MHz):
δ0.80 (m,6H,H$_9$,CH$_3$) 1.15 (s,6H,CH$_3$) 2.01 (s,~0.25H,C$\underline{H}_3$S=O) 2.04 (s,~0.75H,C$\underline{H}_3$S=O) 2.62 (s,3H,SCH$_3$) 3.63 (m,1H,C$\underline{H}$—OH) 4.03 (m,1H,C$\underline{H}$—OH) 5.23 (s,1H,H$_8$,C$\underline{H}$—O)ppm.

EXAMPLE 9

[1S-[1α,4aα,7β,8β(2S*,4S*),8aβ]]-2,2-Dimethylbutanoic acid, 3,3-bis(methylsulfonyl)decahydro-7-methyl-8-[2-(tetrahydro-4-hydroxy-6-oxo-2H-pyran-2-yl)ethyl]-1-naphthalenyl ester A solution of Example 1 (110 mg, 0.22 mmol) in dichloromethane (8.0 ml) was mixed with a solution of 90% m-chloroperoxybenzoic acid (0.97 mmol, 186.7 mg) in dichloromethane (5.0 ml) and was stirred at room temperature. Monitoring by TLC showed the formation of a number of more polar spots due to intermediates, but after 18 hours only a single more polar spot resulting from Example 9 was noted. An excess of the peracid was present at this stage, as indicated by a starch-KI paper test. This excess was destroyed by the addition of a small amount of cyclohexene and stirring for a few minutes. A slight excess of diazomethane in ether was then added to convert all the acid into ester. After a few minutes, the mixture was evaporated in vacuo and the residual oil was chromatographed on a column of silica gel (Baker 60-200 mesh, 12.0 g), eluting the column with dichloromethane, dichloromethane-ethyl acetate mixtures, ethyl acetate and ethyl acetate-reethanol (95%) to afford homogeneous (TLC) Example 9 as a solid (90 mg, 72.5%) with a consistent H$^1$-NMR spectrum. The mass spectrum showed peaks at 582 (M+H+NH$_3$)$^+$, 565 (M+H)$^+$, 547 (M-H$_2$O)$^+$ etc. consistent with the assigned structure.

Example 10

[1S-[1α(βS*,ΔS*),2α,4aβ,8β,8aα]]-8-(2,2-Dimethyl-1-oxobutoxy)decahydro-β,Δ-dihydroxy-2-methyl-6,6-bis(methylsulfonyl)-1-naphthaleneheptanoic acid, monolithium salt A solution of Example 9 (75 mg, 0;133 mmol) in tetrahydrofuran (4.0 ml) was stirred under an atmosphere of nitrogen with 1.0 N lithium hydroxide (0.26 ml) for 20 minutes. The solution was then concentrated in vacuo to remove the tetrahydrofuran, diluted with a small amount of deionized water and applied on a column of HP-20 (1.5"×1.0" column bed). The column was eluted successively with deionized distilled water (150.0 ml) and deionized distilled water-methanol (1:1, 175.0 ml). The later eluate was concentrated in vacuo and the concentrate was lyophilized to afford a hydrated analytical specimen of Example 10 as a white light solid (77.0 mg, 95.7%) with consistent mass, IR, and H$^1$-NMR spectra.

Analysis for C$_{26}$H$_{45}$O$_{10}$S$_2$.Li.0.89H$_2$O: Calc'd: C,51.64; H,7.80; S,10.89; Li,1.15; Found: C,51.64; H,7.77; S,10.63; Li,NA; N,0.67.

IR Spectrum (KBr): μmax 3430 cm$^{-1}$ (strong,OH), 1716 CM$^{-1}$ (strong, C=O,ester), 1589 Cm$^{-1}$ (strong, C=O,salt), 1309 cm$^{-1}$ (strong,sulfone), 1142 or 1129 cm$^{-1}$ (strong,sulfone)

$^1$H-NMR Spectrum (CD$_3$CN, 270 MHz): δ0.85 (t,6.0H,J=7.0 and ~7.0,C$\underline{H}$-CH$_3$) 1.20 (s,6.0H,CH$_3$) 2.72 (s,1.5H, unassigned) 3.13 and 3.14 (two s,3H each SO$_2$CH$_3$) 3.63 (broad s,1.0 H,C$\underline{H}$OH) 4.07 (broad s,1.0 H,C$\underline{H}$) 5.23 (s,1.0OH,C$\underline{H}$—O) 4.50 and 5.85 (broad peaks,OH?)ppm.

EXAMPLE 11

[1S-[1α,3α,4aα,7β,8β(2S*,4S*),8aβ]]-2,2-Dimethylbutanoic acid, 7-methyldecahydro-3-(methylthio)-8-[2-(tetrahydro-4-hydroxy-6-oxo-2H-pyran-2-yl)-ethyl]-1-naphthalenyl ester A solution of 170 mg (0.35 mmol) of Example 1 (melting point 150°-151°) in dry benzene (5.0 ml) containing azabisisobutyronitrile (5.0 mg) and tri-n-butyltinhydride (204 mg, 0.7 mmol) was refluxed under an atmosphere of nitrogen for about 20 minutes. A TLC examination (silica gel, ethyl acetate) showed complete conversion into a slightly more polar compound. The mixture was absorbed on a column of silica gel (Baker 60-200 mesh, 15 g) and the column was successively eluted with dichloromethane and dichloromethane-ethyl acetate mixtures to afford Example 11 as a homogeneous (R$_f$=0.31, silica gel, ethyl acetate) solid (156 mg, 100%) with consistent H$^1$ and C$^{13}$ NMR spectral data. A specimen crystallized as prisms.

Melting point: 169°-170° (from ethyl acetate-hexane).

The H$^1$-NMR and C$^{13}$-NMR spectra showed the presence of a single SCH$_3$ isomer. The αSCH$_3$ stereochemistry was established by X-ray crystallography.

EXAMPLE 12

[1S-[1α(βS*,ΔS*),2α,4aβ,6β,8β,8aβ]]-8-(2,2-Dimethyl-1-oxobutoxy)decahydro-β,Δ-dihydroxy-2-methyl-6-(methylthio)-1-naphthaleneheptanoic acid, monolithium salt A solution of Example 11 (100 mg, 0.228 mmol) in tetrahydrofuran (1.5 ml) was stirred with 1.0 N lithium hydroxide (0.46 ml) under an atmosphere of nitrogen for 30 minutes. The mixture was then concentrated in vacuo and was applied on a column of HP-20 (1"×1.5" column bed), using distilled water. The column was diluted successively with deionized distilled water (220 ml) and deionized distilled water-methanol (1:1, 300 ml). The later eluate was evaporated and lyophilized to afford a hydrated analytical specimen of Example 12 as a light electrostatic solid (95 mg, 84%) with consistent mass, IR and H$^1$-NMR spectral data.

Analysis for C$_{25}$H$_{43}$LiO$_6$S.0.82H$_2$O (M.W.=493.38): Calc'd: C,60.85; H,9.12; S,6.50%; Found: C,60.86; H,9.13; S,6.73%.

IR Spectrum (KBr): 3434 cm$^{-1}$ (strong,OH), 1709,1699 cm$^{-1}$ (medium,C=O), 1587 cm$^{-1}$ (strong,COOLi) etc. H$^1$NMR Spectrum (D$_2$O,270 MHz): δ0.87 (ill-defined doublet+triplet, 6H, ———CH$_3$) 1.23 (s, 6H, ———CH$_3$) 2.09 (s,3H, ———,CH$_3$) 2.30 (m,2H, ———,CH$_2$—C=O) 3.04 (broad s,1H,———,CHSCH$_3$) 3.67 (broad s,1H,———,-CHOH) 4.13 (broad s,1H,———,CH—OH) 5.14 (broad s,1H,———,CH—O)ppm.

EXAMPLE 13

[1S-[1α,3α,4aα,7β,8β(2S*,4S*),8aβ]]-2,2-Dimethyl-
butanoic acid,
7-methyldecahydro-3-(methylsulfinyl)-8-[2-(tetrahy-
dro-4-hydroxy-6-oxo-2H-pyran-2-yl)ethyl]-1-naph-
thalenyl ester A solution of Example 11 (114.8 mg, 0.252 mmol) in a mixture of dichloromethane (4.0 ml) and methanol (1.0 ml) was cooled and stirred in a dry ice-acetone bath at −78° and a solution of 95% m-chloroperoxybenzoic acid (45.67 mg, 0.252 mmol) in dichloromethane (1.0 ml) was added dropwise. The mixture was then gradually allowed to warm to 0° in the course of 3.0 hours, resulting in complete disappearance of Example 11 (TLC). A moderate excess of ethereal diazomethane was then added (in order to convert the acid into the less polar ester to facilitate purification by chromatography) and, after a few minutes, the mixture was concentrated in vacuo. The residue was subjected to column chromatography on Baker 60–200 mesh silica gel (10 g), eluting the column with dichloromethane, dichloromethane-ethyl acetate (1:1), ethyl acetate and ethyl acetate-reethanol (95:5) to afford Example 13 as a homogeneous (TLC, $R_f$=0.3, silica gel, 95:5 ethyl acetate-reethanol colorless powder (109 mg, 91.7%). Both $H^1$ and $C^{13}$-NMR spectra of this were consistent with the structure and showed the presence of two sulfoxide diastereomers in the approximate-ratio 65:35. These diastereomers were riot readily separable by TLC.

EXAMPLE 14

[1S-[1α(βS*,ΔS*),2α,4aβ,8β,8aα]]-8-(2,2-Dimethyl-1-
oxobutoxy)decahydro-β,
Δ-dihydroxy-2-methyl-6-(methylsulfinyl)-1-naph-
thaleneheptanoic acid, monolithium salt A solution of Example 13 (108 mg, 0.229 mmol) in tetrahydrofuran (4.0 ml) was stirred under an atmosphere of nitrogen with 1.0 N lithium hydroxide (0.5 ml) for 30 minutes and then concentrated in vacuo to remove the tetrahydrofuran. The concentrate was dissolved in distilled water and applied on a column of HP-20 (1″×1.5″ column bed), eluting the column successively with deionized distilled water (200 ml) and deionized distilled water-methanol (1:1, 300 ml). The later eluate was concentrated in vacuo and lyophilized to afford a hydrated analytical specimen of Example 14 as an electrostatic, white solid (84 mg, 72%) with consistent mass, IR and $H^1$-NMR spectral data.

Analysis for $C_{25}H_{43}LiSO_7.0.96H_2O$ (M.W.=511.88): Calc'd: C,58.65; H,8.84; S,6.26; Li,1.36%; Found: C,58.39; H,8.86; S,6.53; Li, not done; N,0.19%.

IR Spectrum (KBr): μmax 3429 cm−1 (strong,OH), 1719 cm−1 (strong,C=O), 1587 cm−1 (strong, COOLi), 1045 cm−1 (strong,S=O) etc.

$H^1$-NMR Spectrum (D$_2$O, 270 MHz): δ0.85 (5,6H,CH$_3$) 1.13,1.17 (s,3H each,CH$_3$) 2.48 (d,1H,J=17.0,CH) 2.56 (s,~0.35H,CH$_3$S=O) 2.62 (s,~0.65H,CH$_3$S=O) 3.02 (broad s,1H,CH(S=O)CH$_3$) 3.62 (m,1H,CH-OH) 4.02 (m,1H,CH-OH) 5.12,5.14 (s,1H,CH-O of two diastereomers)ppm.

EXAMPLE 15

[1S-[1α,3α,4aα,7β,8β(2S*,4S*),8aβ]]-2,2-Dimethyl-
butanoic acid,
7-methyldecahydro-3-(methylsulfonyl)-8-[2-(tetrahy-
dro-4-hydroxy-6-oxo-2H-pyran-2-yl)ethyl]-1-naph-
thalenyl ester A solution of Example 11 (150 mg, 0.3 mmol) in dichloromethane (5.0 ml) was stirred at ambient temperature and a solution of 90% m-chloroperoxybenzoic acid (125 mg, 0.66 mmol) in dichloromethane (1.0 ml) was added. Sulfoxide formation was almost immediate, but it took 3.0 hours for completion of sulfone formation from the sulfoxide (TLC). The excess peracid was destroyed by the addition of the minimum amount of dimethylsulfide. A moderate excess of ethereal diazomethane was then added (in order to convert the acid into the less polar ester to facilitate purification by chromatography), and after a few minutes, the mixture was concentrated in vacuo. The residue was subjected to column chromatography on Baker 60-200 mesh silica gel (10 g), eluting with dichloromethane and dichloromethane-ethyl acetate (1:1) to afford Example 15 as a homogeneous (TLC, $R_f$=0.33, silica gel, ethyl acetate), colorless powder (137 mg, 86%). Both $H^1$ and $C^{13}$-NMR spectra of this were consistent with the structure.

EXAMPLE 16

[1S-[1α(βS*,ΔS*),2α,4aβ,6β,8β,
8aβ]]-8-(2,2-Dimethyl-1-oxobutoxy)decahydro-β,Δ-
dihydroxy-2-methyl-6-(methylsulfonyl)-1-naph-
thaleneheptanoic acid, monolithium salt A solution of Example 15 (100 mg, 0.188 mmol) in tetrahydrofuran (4.0 ml) was stirred under an atmosphere of nitrogen with 1.0 N lithium hydroxide (0.38 ml) for 20 minutes and then concentrated in vacuo to remove the tetrahydrofuran. The concentrate was dissolved in distilled water and applied on a column of HP-20 (1″×1.5″ column bed), eluting the column successively with deionized distilled water (200 ml) and deionized distilled water-methanol (1:1, 300 ml). The later eluate was concentrated in vacuo and lyophilized to afford a hydrated analytical specimen of Example 16 as an electrostatic, white solid (93.2 mg, 89.2%) with consistent mass, IR and $H^1$-NMR spectral data.

Analysis for $C_{25}H_{43}O_8SLi.0.61H_2O$ (M.W.=521.29) Mass Spectrum: 503 (M-H)− of acid; 511 (M+H)+; 517 (M+H+Li)+, 509 (M-H+Li)+ of acid, etc. Calc'd: C,57.57; H,8.54; S,6.15; Li,1.33; N,0.00%; Found: C,57.35; H,8.52; S,6.55; Li,not done; N,0.19%.

IR Spectrum (KBr): μmax 3435 cm−1 (strong,OH), 1717 cm−1 (strong,C=0), 1587 cm−1 (strong, COOLi), 1122, 1161 cm−1 (strong, SO$_2$), 1315 to 1279 cm−1. (strong,SO$_2$) etc.

$H^1$-NMR Spectrum (D$_2$O,270 MHz): δ 0.75 (t,6H,CH$_3$) 1.11 (s,3H each,CH$_3$) 2.25 (m,2H,CH$_2$C=O) 2.55 (d,1H,J=17.0,CH) 2.95 (s,3H,SO$_2$CH$_3$) 3.50 (t,1H,CHSO$_2$CH$_3$) 3.60 (m,1H,CH-OH) 4.00 (t,1H,CH-OH) 5.00 (s,1H,CH-O)ppm.

EXAMPLE 17

[1S-[1α,4aα,7β, 8β(2S*,4S*),8aβ]]-2,2-Dimethyl-butanoic acid, 3,3-bis(phenylthio)decahydro-7-methyl-8-[2-(tetrahydro-4-hydroxy-6-oxo-2H-pyran-2-yl)ethyl]-1-naphthalenyl ester To a chilled (ice bath) and stirred solution of compound 1-F (105 mg, 0.25 mmol) in a mixture of dichloromethane (0.5 ml) and glacial acetic acid (0.5 ml) under an atmosphere of argon was added thiophenol (103 μl, 1.0 mmol) followed by borontrifluoride etherate (31 μl, 0.25 mmol). A TLC examination after 1.5 hours at 0° showed the absence of compound 1-F and the presence of only one product. After 2 hours, brine (15 ml) was added and the mixture was extracted with ethyl acetate (3×15 ml). The combined ethyl acetate extracts were washed with brine, dried over anhydrous $Na_2SO_4$ and evaporated in vacuo to give a gum. This gum was chromatographed on a column of silica gel (Baker 60–200 mesh, 30 g), eluting with ethyl acetate-hexane (3:7) to give 100 mg (65.5%) of Example 17 with consistent $H^1$-NMR and $C^{13}$-NMR spectra.

EXAMPLE 18

[1S-[1α(βS*,ΔS*),2α,4aβ,8β,8aα]]-8-(2,2-Dimethyl-1-oxobutoxy)decahydro-β, Δ-dihydroxy-2-methyl-6,6-bis(phenylthio)-1-naphthaleneheptanoic acid, monolithium salt A stirred solution of Example 17 (150 mg, 0.246 mmol) in tetrahydrofuran (5 ml) at room temperature under atmosphere of argon was treated with 1.0N lithium hydroxide (491 μl, 0.491 mmol). After 45 minutes, the solvent was mostly evaporated by a stream of nitrogen to leave a gummy residue. This residue was dissolved in 10% methanol-water and chromatographed on a column of HP-20 (1.51"×1.0" column bed), eluting with deionized, distilled water (300 ml) and 75% methanol-water (300 ml) to give in the later eluate TLC-homogeneous Example 18. This eluate was evaporated in vacuo and lyophilized overnight to give 85 mg (53.3%) of a hydrated analytical specimen of Example 18 as a white solid with consistent IR, mass and $H^1$-NMR spectral data. Analysis for $C_{36}H_{49}O_6S_2.Li1.8H_2O$ (M.W.=681.27): Calc'd: C,63.47; H,7.78; S,9.41. Found: C,63.51; H,7.74; S,9.36.

IR (KBr): 3427 cm$^{-1}$ (OH), 1716 cm$^{-1}$ (C=O,ester), 1583 cm$^{-1}$ (C=O,acid salt). Mass: $(M+Li)^+ = 649$, $(M+Li)^+ +Li=655$, $(M-H)^- =641$, $(M-H)^- +Li=647$ $H^1$-NMR Spectrum ($D_2O$,270 MHz): δ 0.48 (s Broad,3H,$CH_3$) 0.66 (t,3H,$CH_3$) 1.09 (d,6H,$CH_3$) 3.50 (s broad,1H,C$\underline{H}$-OH) 4.02 (s broad,1H,CH-O$\underline{H}$) 4.94 (s broad,1H,C$\underline{H}$-O) 6.96,7.10,7.18,7.27 and 7.56 (5H,broad,aromatic protons) ppm.

EXAMPLE 19

[1S-[1α, 3α,4aα,7β,8β(2S*,4S*),8aβ]]-2,2-Dimethyl-butanoic acid, 7-methyldecahydro-3-(phenylthio)-8-[2-(tetrahydro-4-hydroxy-6-oxo-2H-pyran-2-yl)-ethyl]-1-naphthalenyl ester A solution of Example 17 (100 mg, 0.164 mmol) and tri-n-butyltin hydride (88 μl, 0.327 mmol) in dry benzene (3 ml) was heated to reflux under an atmosphere of argon for 40 minutes. Azobisisobutyronitrile (12 mg) was added in 3 portions every 10 minutes during the refluxing. The resulting solution was cooled down to room temperature. The solvent was evaporated by a stream of nitrogen. The gummy residue was chromatographed on a column of silica gel (25 g, Baker 60-200 mesh), eluting successively with ethyl acetate-hexane (2:8 and 3:7) to give the TLC-homogeneous Example 19 (65 mg, 82.9%) as a solid with consistent $H^1$-NMR and $C^{13}$-NMR spectral data. Another run using Example 17 (170 mg) gave 120 mg more of Example 19.

EXAMPLE 20

[1S-[1α(βS*,ΔS*),2α,4aβ,6β,8βαα]]-8-(2,2-Dimethyl-1-oxobutoxy)decahydro-β,Δ-dihydroxy-2-methyl-6-(phenylthio)-1-naphthaleneheptanoic acid, monolithium salt A stirred solution of Example 19 (60 mg, is 0.116 mmol) in tetrahydrofuran (1.0 ml) at room temperature under an atmosphere of argon was treated with 1.0N lithium hydroxide (232 pl, 0.232 mmol). After 1.0 hour, the solvent was mostly evaporated by a stream of nitrogen to leave a gummy residue. This residue was dissolved in 75% methanol-water and chromatographed on a column of HP-20 (0.5"×1.0" column bed), eluting with deionized, distilled water (200 ml) and 75% methanol-water (200 ml) to give in the later eluate TLC-homogeneous Example 20. This eluate was evaporated in vacuo and lyophilized overnight to give 52 mg (80.9%) of a hydrated analytical specimen of Example 20 as a white solid with consistent IR, mass and $H^1$-NMR spectral data.

Analysis for $C_{30}H_{45}O_6S.Li.0.75H_2O$ (M.W.=554.20): Calc'd.: C,65.01; H,8.46; S,5.78. Found: D,65.18; H,8.24; S,5.46.

IR (KBr) Spectrum: 3437 cm$^{-1}$ (OH), 1716 cm$^{-1}$ (C=O,ester), 1583 cm$^{-1}$ (C=O,acid salt).

Mass Spectrum: $(M+Li)^+ = 541$, $(M+2Li-H)^+ = 547$ $H^1$-NMR Spectrum ($D_2O$,270 MHz): δ 0.73 (d,3H,$CH_3$) 0.80 (t,3H,$CH_3$) 1.07 (d,6H,$CH_3$) 3.35 (s broad,1$\overline{H}$,CH-S) 3.56 (s broad,1H,CH-O$\overline{H}$) 4.04 (s broad,1H,C$\overline{H}$-OH) 5.04 (s broad,1H,C$\overline{H}$-O) 6.87,6.98 and 7.10 (5$\overline{H}$,broad,aromatic protons)ppm.

EXAMPLE 21

[1S-[1α,3α,4aα,7β,8β(2S*,4S*),8aβ]]-2,2-Dimethyl-butanoic acid, 7-methyldecahydro-3-(phenylsulfinyl)-8-[2-(tetrahydro-4-hydroxy-6-oxo-2H-pyran-2-yl)ethyl]-1-naphthalenyl ester To a chilled (−68°, acetone-dry ice bath) and stirred solution of Example 19 (60 mg, 0.116 mmol) in a mixture of dichloromethane (1.0 ml) and methanol (5 drops) under an atmosphere of argon was added dropwise a solution of m-chloroperoxybenzoic acid (80–85%, 23.6 mg, 0.116 mmol) in dichloromethane (0.5 ml). After the addition was complete, the solution was gradually warmed to 0° (ice bath) and stirred for 1.5 hours. The excess m-chloroperoxybenzoic acid was destroyed with one drop of cyclohexene. After a few minutes, the solvent was evaporated by a stream of nitrogen. The gummy residue was dissolved in tetrahydrofuran-ethyl ether (1:2, 2 ml), treated with a slight excess of diazomethane in ethyl ether (to convert the acid into ester) and stirred for a few minutes. The excess diazomethane was destroyed by one drop of glacial acetic acid. The solvent was evaporated by a stream of nitrogen. The gummy residue was chromatographed on two precoated silica gel TLC plates. (E. Merck, 20 cm×20 cm×0.5 mm, ethyl acetate development) to give TLC-homogeneous Example 21 (54 mg, 84.9%) as a solid with consistent H$^1$-NMR and C$^{13}$-NMR spectral data.

EXAMPLE 22

[1S-[1α(βS*,ΔS*),2α,4aβ,6β, 8β, 8aα]]-8-(2,2-Dimethyl-1-oxobutoxy)decahydro-β,Δ-dihydroxy-2-methyl-6-(phenylsulfinyl)-1-naphthaleneheptanoic acid, monolithium salt A stirred solution of Example 21 (52 mg, 0.094 mmol) in tetrahydrofuran (1.0 ml) at room temperature under an atmosphere of argon was treated with 1.0N lithium hydroxide (188 ml, 0.188 mmol). After 1.0 hour, the solvent was mostly evaporated by a stream of nitrogen to leave a gummy residue. This residue was dissolved in 5% methanol-water and chromatographed on a column of HP-20 (0.5"×1.0" column bed), eluting with deionized, distilled water (200 ml) and 70% methanol-water (200 ml) to give in the later eluate TLC-homogeneous Example 22. This eluate was evaporated in vacuo and lyophilized overnight to give 50 mg (92.6%) of a hydrated analytical specimen of Example 22 as a white solid with consistent IR, Mass and H$^1$-NMR spectral data.

Analysis for $C_{30}H_{45}O_7S \cdot Li \cdot 1.0H_2O$ (M.W.=574.70): Calc'd: C,62.69; H,8.24; S,5.58; Found: C,62.59; H,8.31; S,5.64.

IR (KBr) Spectrum: 3441 cm$^{-1}$ (OH), 1718 cm$^{-1}$ (C=O,ester), 1632 cm$^{-1}$ (aromatic c=c), 1586 cm$^{-1}$ (C=O,acid salt). Mass Spectrum: (M+H)$^+$=551, (M+H)$^+$+Li=557, (M+H)$^+$2Li=563, (M-H)$^-$=549, (M+H)$^+$+Na=573, (M+H)$^+$+Na+Li=579, (M+H)$^+$+Na+2Li=585, etc.

H$^1$-NMR Spectrum (D$_2$O, 270 MHz): δ 0.74 (d,3H,J=8.0 ppm,CH$_3$) 0.80 (5,3H,J=8.0 ppm,CH$_3$) 1.19 (d,6H,CH$_3$) 2.27 (m,1H) 2.62 (d,1H,J=16.0 ppm,-CH) 3.10 (s,2H,CH$_2$C=O) 3.63 (narrow m,1H,CH-OH) 4.03 (narrow m,1H,CH-OH) 5.22 (s,1H,CH-O) 7.61 (m,5H,aromatic protons)ppm.

EXAMPLE 23

[1S-[1α,3α,4aα,7β,8β(2S*,4S*),8aβ]]-2,2-Dimethylbutanoic acid, 7-methyldecahydro-3-(phenyl-sulfonyl)-8-[2-(tetrahydro-4-hydroxy-6-oxo-2H-pyran-2-yl)ethyl]-1-naphthalenyl ester A stirred solution of Example 19 (60 mg, 0.116 mmol) in a mixture of dichloromethane (1.0 ml) and methanol (5 drops) at room temperature under an atmosphere of argon was treated with m-chloroperoxybenzoic acid (80-85%, 59 mg, 0.29 mmol). After 2 hours, the excess m-chloroperoxybenzoic acid was destroyed with two drops of cyclohexane. After a few minutes, the solvent was evaporated by a stream of nitrogen. The gummy residue was dissolved in tetrahydrofuran-ethyl ether (3:1, 2 ml), treated with a slight excess of diazomethane in ethyl ether (to convert the acid into ester) and stirred for 1.0 hour. The excess diazomethane was destroyed by two drops of glacial acetic acid. The solvent was evaporated by a stream of nitrogen. The gummy residue was chromatographed on a column of silica gel (15 g, Baker 60-200 mesh), eluting successively with ethyl acetate-hexane (3:7 and 4:6) to give TLC-homogeneous Example 23 (52 mg, 81.6%) as a solid with consistent H$^1$-NMR and C$^{13}$-NMR spectral data.

EXAMPLE 24

[1S-[1α(βS*,ΔS*),2α,4aβ,6β,8β,8aα]-8-(2,2-Dimethyl-1-oxobutoxy)decahydro-β,Δ-dihydroxy-2-methyl-6-(phenylsulfonyl)-1-naphthaleneheptanoic acid, monolithium salt A stirred solution of Example 23 (52 mg, 0.095 mmol) in tetrahydrofuran (1.0 ml) at room temperature under an atmosphere of argon was treated with 1.0N lithium hydroxide (189 μl, 0.189 mmol)- After 1.0 hour, the solvent was mostly evaporated by a stream of nitrogen to leave a gummy residue. This residue was dissolved in 5% methanol-water and chromatographed on a column of HP-20 (0.5"×1.0" column bed), eluting with deionized, distilled water (200 ml) and 75% methanol-water (200 ml) to give in the later eluate TLC-homogeneous Example 24. This eluate was evaporated in vacuo and lyophilized overnight to give 50 mg (93.1%) of a hydrated analytical specimen of Example 24 as a white solid with consistent IR, mass and H$^1$-NMR spectral data.

Analysis for $C_{30}H_{45}O_8S \cdot Li \cdot 1.25H_2O$ (M.W.=595.16): Calc'd: C,60.55; H,8.04; S,5.39; Found: C,60.88; H,7.89; S,5.02.

IR (KBr) spectrum: 3433 cm$^{-1}$ (OH), 1714 cm$^{-1}$ (C=O,ester), 1626 cm$^{-1}$, 1587 cm$^{-1}$ (C=O,acid salt). Mass Spectrum: (f4-H+2Li)+=573, (M-H+2Li)+Li=579, (M-H)$^-$=565, (M-H)$^-$+Li=571, (M-H+2Li)$^+$+Na=595. H$^1$-NMR Spectrum (D$_2$O,270 MHz): δ0.73 (d,3H,J=8.0 ppm,CH$_3$) 0.77 (t,3H,J=8.0 ppm,CH$_3$). 1.15 (d,6H,CH$_3$) 2.27 (m,1H,CH$_2$C=O) 2.68 (sharp d,1H,J=16.0 ppm,CH) 3.51 (s,broad,1H,CH-SO$_2$-) 3.63 (s,braod,1H,CH-OH) 4.03 (s,broad,1H,CH-OH) 5.04 (s,sharp,1H,CH-O) 7.59,7.69 and 7.80 (5H,broad-,aromatic protons)ppm.

EXAMPLE 25

[1S-[1α,3α,4aα,7β,8β(2S*,4S*),8aβ]-2,2-Dimethylbutanoic acid, 3-(acetylthio)decahydro-7-methyl-8-[2-(tetrahydro-4-hydroxy-6-oxo-2H-pyran-2-yl)-ethyl]-1-naphthalenyl ester

Method I

25-A.

[1S-[1α(R*),3β,4β,7β,8β(2S*,4S*),8aβ]]-2-Methylbutanoic acid, 1,2,3,7,8,8a-hexahydro-3-[[(1,1-dimethylethyl)dimethyl-silyl]oxy]-7-methyl-8-[2-(tetrahydro-4-[[(1,1-dimethylethyl)dimethylsilyl]oxy]-6-oxo-2H-pyran-2-yl)ethyl]-1-naphthalenyl ester The starting material for preparation of intermediate A was [1S-[1α(R*),3β,4β,7β,8β(2S*, 4S*),8aβ]]-2-methylbutanoic acid, 1,2,3,7,8,8a-hexahydro-3-hydroxy-7-methyl-8-[2-(tetrahydro-4-hydroxy-6-oxo-2H-pyran-2-yl]-1-naphthalenyl ester. Preparation of this starting material has been described in U.S. Pat. Nos. 3,983,140 and 4,346,227.

A slurry of 21.7 g (0.0535 mol) of the starting material in 50 mL of dry methylene chloride was treated with 5.5 g (0.374 mol, 7.0 eq) of imidazole, followed by 26.6 g (0.176 mol, 3.3 eq) of t-butyl-dimethylsilylchloride. After stirring for 15 hours at ambient temperature under argon, the reaction mixture was filtered and concentrated. The residue was dissolved in ethyl acetate, filtered again, and concentrated. The purified product was isolated by filtration through silica gel, eluting with 25% hexanes in ethyl acetate followed by 10% hexanes in ethyl acetate, to yield 30.3 g (89%) of compound 25-A as a colorless, viscous oil with consistent spectral data. Thin layer chromatography: $R_f$=0.23 (silica gel, 20% ethyl acetate in hexanes).

25-B.
[1S-[1α(R*),3β,4aα,7β,8β(2S*,4S*),8aβ]-2-Methyl-butanoic acid, decahydro-3-[[(1,1-dimethylethyl)dimethylsilyl]oxy]-7-methyl-8-[2-(tetrahydro-4-[[(1,1-dimethylethyl)-dimethylsilyl]oxy]-6-oxo-2H-pyran-2-yl)-ethyl]-1-naphthalenyl ester A solution of 30.3 g (0.0477 mol) of intermediate 25-A in about 250 mL of ethyl acetate was thoroughly degassed and purged with argon. Platinum on carbon (Pt-C) catalyst (1.5 g) was added, and the mixture was subjected to 50 psi of $H_2$ pressure under agitation in a parr apparatus overnight (18 hours). An aliquot of the reaction mixture was treated with HF, and analysis of this by thin layer chromatography indicated that the reaction was incomplete. The reaction mixture was filtered through Celite ®, mixed with more catalyst (1.5 g) and resubjected to $H_2$ (50 psi) on the parr apparatus for an additional 20 hours. At this time, analysis by thin layer chromatography indicated complete reaction with generation of the desired product and some desilylated products. The mixture was filtered through Celite ®, and the filtrate was concentrated in vacuo. The residue was dissolved in about 150 mL of methylene chloride and treated with 4.87 g (0.0716 mol, 1.5 eq) of imidazole and 9.34 g (0.0620 mol, 1.3 eq) of t-butyldimethylsilylchloride. After stirring for 3 hours, the reaction mixture was concentrated, diluted with ethyl acetate, filtered, and concentrated. The crude product was purified by chromatography on silica gel, eluting with 25% ethyl acetate in hexanes to give 30.2 g (99%) of intermediate 25-B as a colorless, viscous oil with consistent $H^1$ and $C^{13}$-NMR spectra. Thin layer chromatography: $R_f$=0.25 (silica gel, 20% ethyl acetate in hexanes).

5-C.
[1S-[1α(R*),30β,4aα,7β,8β(2S*,4S*),8aβ]-2-Methyl-butanoic acid, decahydro-3-[[(1,1-dimethylethyl)dimethylsilyl]oxy]-7-methyl-8-[2-(tetrahydro-4-[[(1,1-dimethylethyl)-dimethylsilyl]oxy]-6-hydroxy-2H-pyran-2-yl)ethyl]-1-naphthalenyl ester A solution of 983 mg (1.54 mmol) of intermediate 25-B in 25 mL tetrahydrofuran was treated with diisobutylaluminum hydride (1.69 mmol, 1.13 mL of a 1.5M solution in toluene) dropwise under argon at −78° C. After stirring for 2 hours at −78° C., methanol (0.27 mL) was added, and the solution was stirred for 10 minutes. The cooling bath was removed, and then water (1.1 mL), Celite ® (1.1 g), and sodium sulfate (5.5 g) were added. This mixture was stirred for 1 hour and then filtered. The filtrate was concentrated in vacuo to give 0.983 g (100%) of a colorless oil which was used directly in the subsequent reaction without further purification. A portion of the crude material was chromatographed on silica gel, eluting with 1% isopropyl alcohol in hexanes. The $^1$H-NMR spectrum showed lactol isomers and trace amounts of starting material.
Thin layer chromatography: $R_f$=0.22-0.39 (silica gel, 20% ethyl acetate in hexanes).

25-D.
[1S-[1α(R*),3β,4aα,7β,8β(2S*,4S*),8aβ]-2-Methyl-butanoic acid, decahydro-3-[[(1,1-dimethylethyl)dimethylsilyl]oxy]-7-methyl-8-[2-(tetrahydro-4-[[(1,1-dimethylethyl)-dimethylsilyloxy]-6-(1-methoxy-1-methyl-ethoxy)-2H-pyran-2-yl)ethyl]-1-naphthalenyl ester To a solution of 881 mg (1.37 mmol) of crude intermediate in 25-C in 15 mL methylene chloride at 0° C. under argon was added 1.97 mL (20.6 mmol, 15 eq) of 2-methoxypropene, followed by a solution of 21 mg (0.0825 mmol, 0.06 eq) of pyridinium p-toluene sulfonate (PPTS) in 2 mL methylene chloride. After stirring the mixture for 3 hours,. the homogeneous reaction mixture was poured into aqueous sodium hydrogen carbonate and diluted with ethyl acetate. The aqueous layer was extracted with ethyl acetate (twice), and the combined organic layers were dried (magnesium sulfate), concentrated, and chromatographed on silica gel, eluting with 5% ethyl acetate in hexanes followed by 25% ethyl acetate in hexanes.

A higher $R_f$ impurity was present in some of the fractions containing intermediate 25-D. These fractions were combined, concentrated, and rechromatographed on silica gel, eluting first with hexanes and then with 5% ethyl acetate in hexanes. The other fractions, from the first column containing intermediate 25-D, were slightly impure with a lower $R_f$ impurity. These fractions were combined, concentrated, and rechromatographed on silica gel, eluting with 10% ethyl acetate in hexanes. All the fractions containing intermediate 25-D were combined, concentrated, and dried in vacuo to give 624 mg (64%) of intermediate 25-D as a colorless, viscous oil with a consistent $H^1$-NMR spectrum. Thin layer chromatography: $R_f$=0.56 (silica gel, 20% ethyl acetate in hexanes).

25-E.
[1S-[1α,3β,4aα,7β,8β(2S*,4S*),8aβ]-Decahydro-3-[[(1,1-dimethylethyl)dimethyl-silyl]oxy]-7-methyl-8-[2-(tetrahydro-4-[[(1,1-dimethylethyl)dimethylsilyl]oxy]-6-(1-methoxy-1-methylethoxy)-2H-pyran-2-yl)ethyl]-1-naphthalenol A solution of 591 mg (0.829 mmol) of intermediate 25-D in 12 mL of diethyl ether was added to a suspension of 230 mg (6.07 mmol, 7.3 eq) of lithium aluminum hydride in 15 mL diethyl ether (2×2 mL ethyl ether rinses were used for complete transfer of intermediate 25-D). After stirring for 1.25 hours at ambient temperature under argon, the reaction mixture was treated successively with water (0.230 mi), aqueous 20% sodium hydroxide (0.230 mi), and water (0.690 mL). After vigorously stirring for 1 hour, the mixture was filtered, washing with ethyl acetate. The filtrate was concentrated, and the crude product was chromatographed on silica gel, eluting with 7% ethyl acetate in hexanes. The purified product was isolated as a colorless, viscous oil in a yield of 489 mg (96%) and showed a consistent $H^1$-NMR spectrum. Thin layer chromatography: $R_f$=0.42 (silica gel, 20% ethyl acetate in hexanes).

25-F.
[1S-[1α,3β,4aα,7β,8β(2S*,4S*),8aβ]-Octahydro-3-[[(1,1-dimethylethyl)dimethyl-silyl]oxy]-7-methyl-8-[2-[tetrahydro-4-[[(1,1-dimethylethyl)dimethylsilyl]oxy]-6-(1-methoxy-1-methylethoxy)-2H-pyran-2-yl]-ethyl]1-(2H)-naphthalenone A solution of 450 mg (0.734 mmol) of intermediate 25-E in 3 mL of methylene chloride was added to a solution of Dess-Martin periodinane in 4 mL methylene chloride via a cannula and 2×1 mL methylene chloride rinses were used for complete transfer of intermediate 25-E. After 30 minutes, the homogeneous reaction mixture was diluted with 60 mL of diethyl ether and poured-into a solution of 0.850 g sodium thiosulfate (5.38 mmol, 7.3 eq) in 10 mL of aqueous sodium hydrogen carbonate. The mixture was stirred for 15 minutes, transferred to a separatory funnel, and the layers separated. The ethyl ether layer was washed with 5 mL aqueous sodium hydrogen carbonate and 5 mL water, dried with magnesium sulfate, and concentrated. The product was purified by silica gel chromatography, eluting with hexanes (250 mL) and then 5% ethyl acetate in hexanes (250 mL) to yield 377 mg (82%) of compound 25-F as a colorless, viscous oil with a consistent H$^1$-NMR spectrum. Thin layer chromatography: R$_f$=0.53 (silica gel, 20% ethyl acetate in hexanes).

25-G.
[1S-[1α,3β,4aα,7β,8β(2S*,4S*),8aβ]-Octahydro-7-methyl-8-[2-[tetrahydro-4-[[(1,1-dimethylethyl)dimethylsilyloxyl-6-(1-methoxy-1-methylethoxy)-2H-pyran-2-yl]-ethyl]-1-(2H)-naphthalenone A solution of 360 mg (0.574 mmol) of ketone 25-F in 5 ml of dimethylformamide was treated with 215 μl (1.44 mmol) of 1,8-diazabicyclo[5,4,0]-undec-7-ene and the resultant mixture was heated to 80° C. for 2 hours, 125° C. for 0.75 hour, and 100° C. for 12 hours. The reaction mixture was then diluted with 30 ml of ethyl acetate and washed with water (1×10 ml), followed by brine (2×10 ml). The organic layer was dried (magnesium sulfate), filtered, and concentrated. The residue was chromatographed on Merck silica gel, eluting with a stepwise gradient of 5 to 10% ethyl acetate in hexanes. Fractions containing enone 25-G were combined and concentrated in vacuo to give 196 mg (60%) of a yellow oil with a consistent H$^1$-NMR spectrum.

TLC: R$_f$=0.33 (Silica gel; 20% ethyl acetate in hexanes)

25-H.
[1S-[1α,3β,4aα,7β,8β(2S*,4S*),8aβ]-Octahydro-3-acetylthio-7-methyl-8-[2-[tetrahydro-4-[[(1,1-dimethylethyl)dimethyl-silyl]oxy]-6-(1-methoxy-1-methylethoxy)-2H-pyran-2-yl]ethyl]-1-(2H)-naphthalenone To a 0° C. solution of 550 mg (1.11 mmol) of compound 25-G in 1.5 ml of dichloromethane was added, 1.70 ml (12.2 mmol) of triethylamine followed by 0.790 ml (11.1 mmol) of thiolacetic acid. The mixture was immediately allowed to warm to ambient temperature. After stirring for 15 hours at ambient temperature, the mixture was concentrated in vacuo. The crude product was loaded onto a hexanes-packed silica gel column. Elution with a stepwise gradient of ethyl acetate in hexanes from 1% to 5% to 10% afforded 420 mg (66%) of compound 25-H as a pale yellow oil with a consistent H$^1$-NMR spectrum.

TLC: R$_f$=0.30 (Silica gel; 20% ethyl acetate in hexanes).

25-I.
[1S-[1α,3β,4aα,7β,8β(2S*,4S*),8aβ]-Octahydro-3-acetylthio-7-methyl-8-[2-[tetrahydro-4-[[(1,1-dimethylethyl)dimethyl-silyl]oxy]-6-(1-methoxy-1-methylethoxy)-2H-pyran-2-yl]ethyl]-1-naphthalenol A solution of 3.0 g (5.25 mmol) of thiolacetate-ketone 25-H in 75 ml of dry tetrahydrofuran at 0° C. under argon was treated with 5.25 ml (5.25 mmol) of 1M lithium tri-t-butoxyaluminum hydride in tetrahydrofuran. After 30 minutes, the mixture was allowed to warm to ambient temperature and then stirred for 16 hours. By TLC analysis, 5–10% of compound 25-H remained; therefore, 750 μl (0.14 mmol) of 1M lithium tri-t-butoxyaluminum hydride in tetrahydrofuran was added. After stirring for an additional 1.5 hour, the reaction mixture was diluted with 100 ml of ethyl ether, quenched with 30 ml of pH 4 buffer, and transferred into a separatory funnel. After thoroughly mixing, the two layers were separated. The organic layer was washed with brine, dried (magnesium sulfate), filtered and concentrated. The crude product was chromatographed on Merck silica gel, eluting with a stepwise gradient system of ethyl acetate in hexanes (50 ml portions of 5%, 6.5%, 8.5%, and finally 10%). Compound 25-I was obtained in a yield of 1.81 g (60%) and showed a consistent H$^1$-NMR spectrum.

TLC: R$_f$=0.18 (silica gel; 20% ethyl acetate in hexanes).

25-J.
[1S-[1α,3β,4aα,7β,8β(2S*,4S*),8aβ]-Octahydro-3-acetylthio-7-methyl-8-[2-[tetrahydro-4-[[(1,1-dimethylethyl)dimethyl-silyl]oxy]-6-hydroxy-2H-pyran-2-yl]ethyl]-1-naphthalenol To a 0° C. solution of 1.75 g (3.05 mmol) of methoxymethylethyl mixed acetal 25-I in 8 ml of tetrahydrofuran and 3 ml of water was added 4 ml of acetic acid, and the resultant mixture was allowed to warm to ambient temperature. After stirring for 4 hours, the mixture was diluted with ethyl acetate and washed with brine (three times). The organic layer was dried (magnesium sulfate), filtered, diluted with about 30 ml of toluene and then concentrated in vacuo. The crude product was loaded onto a column of silica gel, packed with 10% ethyl acetate in hexanes. Elution with 25% ethyl acetate in hexanes afforded compound 25-J in a yield of 1.37 g (90%) as a colorless oil with a consistent H$^1$-NMR spectrum.

TLC: R$_f$=0.19–0.27 (silica gel; 40% ethyl acetate in hexanes)

25-K.
[1S-[1α,3β,4aα,7β,8β(2S*,4S*),8aβ]-Octahydro-3-acetylthio-7-methyl-8-[2-[tetrahydro-4-[[(1,1-dimethylethyl)dimethylsilyl]oxy]-6-oxo-2H-pyran-2-yl]ethyl]-1-naphthalenol A −20° C. solution of 204 mg (0.407 mmol) of lactol 25-J in 7 ml of dry tetrahydrofuran under argon was treated dropwise with 1.43 pl (0.427 mmol) of 3M phenylmagnesium bromide. After stirring for 15 minutes, the cooling bath was removed and stirring was continued for an additional 5 minutes. At this time, 115 mg (0.448 mmol) of 1,1'-(azodicarbonyl)dipiperidine was added. After stirring for 5 hours, the reaction mixture was diluted with ethyl ether and filtered. The filtrate was washed with brine, saturated aqueous sodium hydrogen carbonate, and brine again. The aqueous layers were extracted with ethyl ether (twice). The organic layers were combined, dried (magnesium sulfate), filtered and concentrated. The crude product was purified by silica gel chromatography, eluting with 15% ethyl acetate (150 ml) followed by 20% ethyl acetate in hexanes (400 ml). Compound 25-K was isolated in a yield of 161 mg (79%) as a pale yellow oil with a consistent $H^1$-NMR spectrum. TLC: $R_f=0.28$ (silica gel, 40% ethyl acetate in hexanes).

25-L.
[1S-[1α,3α,4aα,7β,8β(2S*,4S*),8aβ]]-2,2-Dimethylbutanoic acid,
3-(acetylthio)decahydro-7-methyl-8-[2-(tetrahydro-4-[[(1,1-dimethylethyl)silyl]oxy]-6-oxo-2H-pyran-2-yl)ethyl]-1-naphthalenyl ester A solution of 518 mg (1.04 mmol) of alcohol 25-K in 5 ml of dry pyridine was treated with 2.13 ml (15.6 mmol) of 2,2-dimethylbutyryl chloride and 132 mg (1.04 mmol) of 4-dimethylaminopyridine, and the resultant mixture was heated to 75° C. for 10 hours. The mixture was then diluted with ethyl acetate and washed with water, followed by brine. The organic layer was dried (magnesium sulfate), filtered, and concentrated. The residue was chromatographed on silica gel, eluting with 10% ethyl acetate in hexanes to give 489 mg (79%) of compound 25-L as a very pale yellow oil with a consistent $H^1$-NMR spectrum. TLC: $R_f=0.44$ (silica gel; 40% ethyl acetate in hexanes).

25-M.
[1S-[1α,3α,4aα,7β,8β(2S*,4S*),8aβ]]-2,2-Dimethylbutanoic acid,
3-(acetylthio)decahydro-7-methyl-8-[2-(tetrahydro-4-hydroxy-6-oxo-2H-pyran-2-yl)ethyl]-1-naphthalenyl ester A 0° C. solution of 397 mg (0.665 mmol) of bis-silyl ether 25-L in 6 ml of acetonitrile was treated dropwise with 0.5 ml of HF-pyridine and then 1 ml of HF-pyridine. The reaction was complete, as analyzed by TLC, after the addition of the second portion of HF-pyridine. The mixture was diluted with ethyl acetate and washed with a saturated aqueous sodium hydrogen carbonate solution until basic and then with brine (twice). The aqueous layers were combined and extracted with ethyl acetate. The organic layers were combined, dried (magnesium sulfate), filtered, and concentrated. The crude product was purified by silica gel chromatography, eluting with 45% ethyl acetate in hexanes. Hydroxylactone Example 25 was isolated in a yield of 316 mg (98%) and showed a consistent $H^1$-NMR spectrum.

TLC: $R_f=0.25$ (silica gel, 80% ethyl acetate in hexanes).

Method II
25-N.
[1S-[1α,3α,4aα,7β,8β(2S*,4S*),8aβ]]-2,2-Dimethylbutanoic acid,
3-(acetylthio)-decahydro-7-methyl-8-[2-[tetrahydro-4-[(phenylmethoxy)methoxy]-6-oxo-2H-pyran-2-yl]ethyl]-1-naphthalenyl ester To a stirred solution of triphenylphosphine (2 parts) in tetrahydrofuran in an ice bath was added a solution of diisopropylazadicarboxylate (2 parts), resulting in the formation of a solid. After 30 minutes, a solution of compound 1-E (1 part) and thiolacetic acid (2 parts) in tetrahydrofuran was added. After 1.0 hour, the mixture was warmed to ambient temperature. After 2.0 hours, the mixture was evaporated and chromatographed on a column of silica gel to isolate compound 25-N with consistent spectral data.

Compound 25-N is then hydrogenated ($H_2$, balloon) to yield Example 25.

EXAMPLE 26

[1S-[1α(βS*,ΔS*),2α,4aβ,6β,8β,8aβ]]-8-(2,2-Dimethyl-1-oxobutoxy)decahydro-β,Δdihydroxy-6-mercapto-2-methyl-1-naphthaleneheptanoic acid, monosodium salt A 0° C. solution of 146 mg (0.302 mmol) of hydroxylactone Example 25 in 10 ml of methanol was treated with 0.302 ml (0.302 mmol) of 1N sodium hydroxide, and then the cooling bath was removed. By TLC analysis, complete consumption of starting material and the generation of two products, presumably the desired product and its methyl ester, was observed. A precipitate was also observed. Another 10 ml of methanol was added to dissolve the precipitate. After stirring for 3 hours, TLC showed that the methyl ester side product was still present, so 45 ml (0.15 mmol) of 1N sodium hydroxide was added. After an additional 2 hours of stirring, trace amounts of the methyl ester side product remained. The mixture was concentrated in vacuo. The residue was dissolved in a minimum amount of water and chromatographed on CHP-20P, eluting with 200 ml of water, followed by a stepwise gradient system of acetonitrile in water (100 ml of 5%, 200 ml of 10%, 200 ml of 12.5%, 200 ml of 15%, 200 ml of 20%, and 200 ml of 25%). Product fractions were combined and concentrated in vacuo. The residue was dissolved in water, a aqueous solution was filtered (Millipore, cellulose, nitrate), concentrated to about 2 ml and lyophilized to give 120 mg (83%) of Example 26 as a white solid. This was a hydrated specimen and showed an $H^1$-NMR spectrum and elemented analysis data consistent with the structure.

TLC: $R_f=0.43$ (silica gel, 20:1;1 methylene chloride:methanol:acetic acid, anisaldehyde stain. $[\alpha]^{25}_D = +66.40°$ (c=0.25,methanol).

EXAMPLE 27

[1S-[1α,4aα,7β,8β(2S*,4S*),8aβ]]-2,2-Dimethylbutanoic acid,
3,3-bis(ethylthio)decahydro-7-methyl-8-[2-(tetrahydro-4-hydroxy-6-oxo-2H-pyran-2-yl)ethyl]-1-naphthalenyl ester To a chilled (−20°, dry ice-carbon tetrachloride bath) and stirred solution of compound 1-G (300 mg, 0.71 mmol) in a mixture of dichloromethane (1.5 ml) and glacial acetic acid (1.5 ml) under an atmosphere of argon was added ethanethiol (210 μl, 2.83 mmol) followed by borontrifluoride etherate. (88 μl, 0.71 mmol). A TLC examination after 1.0 hour at −20° showed the absence of compound and the presence of only one product. After 1.5 hours, brine (15 ml) was added and the mixture was extracted with ethyl acetate (4×15 ml). The combined ethyl acetate extracts were washed with brine, dried over anhydrous sodium sulfate and evaporated in vacuo to give a gum. This gum was chromatographed on a column of silica gel (Baker 60–200 mesh, 20 g), eluting with ethyl acetate-hexane (3:7) to give 300 mg (79.9%) of Example 27 with consistent $H^1$-NMR and $C^{13}$-NMR spectra.

EXAMPLE 28

[1S-[1α,3α,4aα,7β,8β(2S*,4S*),8aβ]]-2,2-Dimethylbutanoic acid,
3-(ethylthio)decahydro-7-methyl-8-[2-(tetrahydro-4-hydroxy-6-oxo-2H-pyran-2-yl)-ethyl]-1-naphthalenyl ester A solution of Example 27 (300 mg, 0.567 mmol) and tri-n-butyltin hydride (305 ml, 1.135 mmol) in dry benzene (8 ml) was heated to reflux under an atmosphere of argon for 40 minutes. Azobisisobutyronitrile (30 mg) was added in 3 portions every 10 minutes during the refluxing. The resulting solution was cooled down to room temperature. The solvent was evaporated by a stream of nitrogen. The gummy residue was chromatographed on a column of silica gel (25 g, Baker 60–200 mesh), eluting successively with ethyl acetate-hexane (2:8, 3:7 and 1:1) to give the TLC-homogeneous Example 28 (255 mg, 96.0%) as a solid with consistent $H^1$-NMR and $C^{13}$-NMR spectral data.

EXAMPLE 29

[1S-[1α(βS*,ΔS*),2α,4aα,6β,8β,8aα)]-8-(2,2-Dimethyl-1-oxobutoxy)-6-(ethylthio)decahydro-β,Δ-dihydroxy-2-methyl-1-naphthaleneheptanoic acid, monolithium salt A stirred solution of Example 28 (70 mg, 0.15 mmol) in tetrahydrofuran (1.5 ml) at room temperature under an atmosphere of argon was treated with 1.0N lithium hydroxide (300 ml, 0.3 mmol). After 1.0 hour, the solvent was mostly evaporated by a stream of nitrogen to leave a gummy residue. This was dissolved in water and chromatographed on a column of HP-20 (0.5"×1.0" column bed), eluting with deionized, distilled water (200 ml) and 70% methanol-water (200 ml) to give in the later eluate TLC-homogeneous Example 29. This eluate was evaporated in vacuo and lyophilized overnight to give 60 mg (79.7%) of a hydrated analytical specimen of Example 29 as a white solid with consistent IR, mass and $H^1$-NMR spectral data.

Analysis for $C_{26}H_{45}O_6S.Li.0.5H_2O$ (M.W.=501.65): Calc'd: C,62.25; H,9.24; S,6.39; Found: C,62.06; H,9.35; S,6.78.

IR(KBR) Spectrum: 3434 cm$^{-1}$ (OH);-1717 cm$^{31\ 1}$ (C=O,ester), 1582 cm$^1$ (C=O,acid salt). Mass Spectrum: (M-H)$^-$=485, (M-2H+Li)$^-$=491, (M+Li)$^+$=493, (M+2Li-H)$^+$=499, etc. $H^1$-NMR Spectrum (D$_2$,270 MHz): δ0.67 (d,3H,C$\underline{H}_3$) 0.69 (t,3H,C$\underline{H}_3$) 1.06 (s,6H,C$\underline{H}$-$_3$) 2.39 (m,2H,C$\underline{H}_2$S-) 3.03 (s,broad,1H,C$\underline{H}$S) 3.52 (s,broad,1H,C$\underline{H}$-O$\underline{H}$) 3.94 (s,broad,1H,C$\underline{H}$-OH) 4.95 (s,broad,1H,C$\underline{H}$-O)ppm.

EXAMPLE 30

[1S-[1α,4aα,7β,8β(2S*,4S*),8aβ]]-2,2-Dimethylbutanoic acid,
3,3-[1,2-ethanediylbis(sulfonyl)]-decahydro-7-methyl-8-[2-(tetrahydro-4-hydroxy-6-oxo-2H-pyran-2-yl)ethyl]-1-naphthalenyl ester To a stirred solution of Example 3 (79 mg, 0.159 mmol) in dichloromethane (5.0 ml) a solution of 90% m-chloroperoxybenzoic acid (182 mg, 0.95 mmol) in dichloromethane (6.0 ml) was added, resulting within a few minutes in the formation of a number of products (TLC, silica gel, ethyl acetate, methanol, 97:3). It took about 36 hours for completion of the conversion of all these compounds into Example 30. A small amount of cyclohexene was then added to decompose the excess peracid. After 30 minutes, a slight excess of ethereal diazomethane was added to convert all the m-chlorobenzoic acid into the ester. After 10 minutes, the mixture was evaporated and the residual solid was purified by column chromatography on silica gel (Baker 60–200 mesh, 15 g), eluting the column with dichloromethane and dichloromethane-ethyl acetate (2:8 and 3:7) to afford homogeneous (TLC, silica gel, ethyl acetate, R$_f$=0.5) Example 30 as a relatively insoluble colorless solid (88 mg, 98.4%). One crystallization of a specimen from ethyl acetate gave micro-crystals with melting point 250°–251° (no decomp.) with a consistent $H^1$-NMR spectrum.

EXAMPLE 31

[1S-[1α(βS*,Δ&S*),2α,4aβ,8β,8aβ]]-8-(2,2-Dimethyl-1-oxobutoxy)-6,6-[1,2-ethanediylbis-(sulfonyl)]-decahydro-β, Δ-dihydroxy-2-methyl-1-naphthaleneheptanoic acid, monolithium salt A solution of Example 30 (77 mg, 0.137 mmol) in tetrahydrofuran was stirred for 15 minutes, under an atmosphere of nitrogen with 1.0N lithium hydroxide (0.27 ml). The mixture was then concentrated, dissolved in deionized distilled water (5.0 ml) and applied on a column of HP-20 (1"×1.5" column bed). The column was eluted successively with deionized distilled water (150 ml) and deionized distilled water-methanol (1:1, 200 ml). The later eluate was evaporated in vacuo and the concentrate was lyophilized to give a hydrated analytical specimen of Example 31 as a homogeneous (TLC) light white solid (68 mg, 82.7%) with consistent mass, IR, and $H^1$-NMR spectral data.

Analysis for $C_{26}H_{43}O_{10}O_{12}S_2Li.2.4H_2O$ (M.W.628,09): Calc'd: C,49.57; H,7.26; S,10.17%; Found: C,49.31; H,7.30; S,9.95%.

Mass Spectrum: (M+H)$^+$=587, (M+H+Li)$^+$=593, (M+H+Li+Na)$^+$=609 (M-H)$^-$=579, (M-2H+Li)$^-$=585, (M-2H+Na)$^-$=601, (M-H-SO2)$^-$=515, (M-H-SO2+Li)$^-$=521, (M-H-SO2+Na)$^-$=537, etc. IR Spectrum (KBr): μmax 3423 cm$^{-1}$ (strong, 1717 cm$^{-1}$ (mediumester C=O), 1586 cm$^{-1}$ (strong, salt C=O), 1335 cm$^{-1}$ (strong, SO2), 1124 cm$^{-1}$ (strong,SO2 etc.).

$H^1$-NMR Spectrum (DMSO-d$_6$,270 MHz): δ 0.75 (t,3H,J=%8.0,CH$_3$) 0.78 (t,3H,J=%8.0,CH$_3$) 1.10 (s,6H,CH$_3$) 3.45 (broad s,1H,CHOH) 3.72 (broad s,1H,C$\underline{H}$-OH) 3.85,4.13 m,4H,C$\underline{H}_2$$\overline{S}$O$_2$) 5.08 (s,1H,C$\underline{H}$-O)PPM.

EXAMPLE 32

A.

[1S-[1α,3α,4aα,7β,8β(2S*,4S*),8aβ]]-2,2-Dimethylbutanoic acid,
3-(ethylsulfinyl)decahydro-7-methyl-8-[2-[tetrahydro-4-hydroxy-6-oxo-2H-pyran-2-yl)ethyl]-1-naphthalenyl ester , (R)-sulfur; and B.  [1S-[1α,3α,4aα,7β,8β(2S*,4S*),8aβ]]-2,2-Dimethylbutanoic acid, 3-(ethylsulfinyl)decahydro-7-methyl-8-[2-[tetrahydro-4-hydroxy-6-oxo-2H-pyran-2-yl)ethyl]-1-naphthalenyl ester, (S)-sulfur A chilled (0°, ice bath) and stirred solution of Example 28 (100 mg, 0.213 mmol) in a mixture of dichloromethane (1.0 ml) and methanol (0.5 ml) under an atmosphere of argon was added dropwise to a solution of m-chloroperoxybenzoic acid (80–85%, 44 mg, 0.213 mmol) in dichloromethane (0.5 ml). After the addition was complete, the solution was gradually warmed to room temperature and stirred for 1 hour. The excess m-chloroperoxybenzoic acid was destroyed with one drop of cyclohexene. After a few minutes, the solvent was evaporated by a stream of nitrogen. The gummy residue was dissolved in tetrahydrofuran-ethyl ether (1:1, 2 ml), treated with a slight excess of diazomethane in ethyl ether (to convert the acid into ester), and stirred for a few minutes. The excess diazomethane was destroyed by one drop of glacial acetic acid. The solvent was evaporated by a stream of nitrogen. The gummy residue was chromatographed on silica gel (50 g, LPS-1), eluting with ethyl acetate-dichloromethane (8:2) to give TLC-homogeneous (silica gel, dichloromethane methanol 95:5) Example 32-A as a solid (36 mg, 36.8%, less polar isomer, R-configuration at sulfur, melting point 214-2150) and Example 32-B as a solid (60 mg, 58.1%, more polar isomer, S-configuration at sulfur, melting point 214°-216°) with consistent $H^1$-NMR and $C^{13}$-NMR spectral data. Another run using 70 mg of Example 28 gave 29 mg more of compound 32-A and 40 mg more of Example 32-B.

EXAMPLE 33

[1S-[1α(βS*,ΔS*),2α,4aβ,6β,8β,8aβ]]-8-(2,2-Dimethyl-1-oxobutoxy)-6-(ethylsulfinyl)-decahydro-β,Δ-dihydroxy-2-methyl-1-naphthaleneheptanoic acid, (R)-sulfur, monolithium salt A stirred solution of Example 32-A (65 mg, 0.134 mmol) in tetrahydrofuran (10 ml) at room temperature under an atmosphere of argon was treated with 1.0N lithium hydroxide (268 μl 0.268 mmol). After 2.5 hours, the solvent was mostly evaporated by a stream of nitrogen to leave a gummy residue. This residue was dissolved in water and chromatographed on a column of HP-20 (1.0″×1.0″ column bed), eluting with deionized, distilled water (250 ml) and 70% methanol-water (250 ml) to give in the later eluate TLC-homogeneous Example 33. This eluate was evaporated in and lyophilized overnight to give 65 mg (92.1%) of a hydrated analytical specimen of Example 33 as a white solid with consistent IR, mass and $H^1$-NM spectral data.

Analysis for $C_{24}H_{45}O_7S\cdot Li\cdot 1.0H_2O$ (M.W.=526.66). Calc'd: C,59.29; H,9.00; S,6.09; Found: C,59.32; H,9.15; S,6.45.

IR (KBr) Spectrum: 3426 $cm^{-1}$ (OH), 1717 $cm^{-1}$ (C=O,ester), 1576 $cm^{-1}$ (C=O,acid salt).

Mass Spectrum $(M+Li)^+ =509$, $(M-H+2Li)^+ =515$, $(M-H)^- =501$, $(M-2H+Li)^- =507$, etc. $H^1$-NMR Spectrum: ($D_2O$, 400 MHz): δ 0.77 (d,3H,J=8.0 ppm, $CH_3$) 0.78 (t,3H,J=8.0 ppm,$CH_3$) 1.13 (s,6H,$CH_3$) 1.24 (t,3H,$CH_3$-) 2.29 (m,1H,$CH$-$OH$) 2.56 (M,1H,J=8.0ppm,$CH_2S$=O) 2.87 (m,1H,J=8.0ppm,$CH_2S$=O) 3.10 (s,1H,CHS=O) 3.63 (m,1H,$CH$-OH) 4.03 (m,1H,$CH$-OH) 5.12 (S,1H,$CH$-O)ppm.

EXAMPLE 34

[1S-[1α(βS*,ΔS*),2α,4aβ,6β,8β,8aα]]-8-(2,2-Dimethyl-1-oxobutoxy)-6-(ethylsulfinyl)-decahydro-β,Δ-dihydroxy-2-methyl-1-naphthaleneheptane acid, (S)-sulfur, monolithium salt A stirred solution of Example 32-B (100 mg, 0.206 mmol, S-configuration at sulfur) in tetrahydrofuran (25 ml) at room temperature under an atmosphere or argon was treated with 1.0N lithium hydroxide (412 pl, 0.412 mmol). After 2.5 hours, the solvent was mostly evaporated by a stream of nitrogen to leave a gummy residue. This residue was dissolved in water and chromatographed on a column of HP-20 (1.5″×1.0″ column bed), eluting with deionized, distilled water (250 ml) and 70% methanol-water (250 ml) to give in the later eluate TLC-homogeneous Example 34. This eluate was evaporated In vacuo and lyophilized overnight to give 100 mg (92.9%) of a hydrated analytical specimen of Example 34 as a white solid with consistent IR, mass and $H^1$-NMR spectral data.

Analysis for $C_{26}H_{45}O_7S\cdot Li\cdot 0.75H_2O$ (M.W.=522.15): Calc'd: C,59.80; H,8.98; S,6.14; Found: C,59.62; H,9.09; S,6.38.

IR(KBr)Spectrum: 3427 $cm^{-1}$ (OH), 1718 $cm^{-1}$ (C=O,ester),1587 $cm^{-1}$ (C=O,acid salt). Mass Spectrum: $(M+Li)^+ =509$, $(M-H+2Li)^+ =515$, $(M-H)^- =501$, $(M-2H+Li)^- =507$, etc.

$H^1$-NMR Spectrum ($D_2O$,400 MHz): δ 0.76 (d,3H,J=8.0 ppm,$CH_3$) 0.79 (t,3H,J=8.0 ppm,$CH_3$) 1.13 (s,3H,$CH_3$) 1.16 (s,3H,$CH_3$) 1.25 (t,3H,$CH_3$) 2.28 (M,2H,$CH_2C$=O) 2.45 (d,1H,J=16.0 ppm,$CH$) 2.57 (m,1H,J=8.0 ppm,$CH_2S$=O) 3.06 (m,1H,J=8.0 ppm,$CH_2S$=O) 3.08 (m,1H,$CH$-S=O) 3.65 (m,1H,$CH$-OH) 4.02 (M,1H,$CH$-OH) 5.14 (s,1H,$CH$-O)ppm.

EXAMPLE 35

[1S-[1α,3α,4aα,7β,8β(2S*,4S*),8aβ]]-2,2-Dimethylbutanoic acid, 3-(ethylsulfonyl)dechydro-7-methyl-8-[2-(tetrahydro-4-hydroxy-6-oxo-2H-pyran-2-yl)ethyl]-1-naphthalenyl ester A stirred solution of Example 28 (75 mg, 0.16 mmol) in a mixture of dichloromethane (2.0 ml) and methanol (0.4 ml) at room temperature under an atmosphere of argon was treated with m-chloroperoxybenzoic acid (80-85%, 82 mg, 0.40 mmol). After 2 hours, the excess m-chloroperoxybenzoic acid was destroyed with two drops of cyclohexane. After a few minutes, the solvent was evaporated by a stream of nitrogen. The residue was redissolved in tetrahydrofuran-ethyl ether (3:1, 3 ml), treated with a slight excess diazomethane in ethyl ether (to convert the acid into ester) and stirred for 0.5 hours. The excess diazomethane was destroyed by two drops of glacial acetic acid. The solvent was evaporated by a stream of nitrogen. The gummy residue was chromatographed on a column of silica gel (20 g, Baker 60-200 mesh), eluting successively with ethyl acetate-hexane (4:6, 5:5 and 6:4) to give TLC-homogeneous Example 28 (70 mg, 87.4%) as a gum with consistent $H^1$-NMR and $C^{13}$-NMR spectral data.

EXAMPLE 36

[1S-[1α(βS*,ΔS*),2α,4aβ,6β,8β,8aα]]-8-(2,2-Dimethyl-1-oxobutoxy)-6-(ethylsulfonyl)decahydro-β,Δ-dihydroxy-2-methyl-1-naphthaleneheptanoic acid, monolithium salt A stirred solution of Example 35 (70 mg, 0.14 mmol) in tetrahydrofuran (1.5 ml) at room temperature under an atmosphere of argon was treated with 1.0N lithium hydroxide (280 μl, 0.28 mmol). After 1.0 hour, the solvent was mostly evaporated by a stream of nitrogen to leave a gummy residue. This residue was dissolved in water and chromatographed on a column of HP-20 (1.0″×1.0″ column bed), eluting with deionized, distilled water (250 ml) and 70% methanol-water (250 ml) to give in the later eluate TLC-homogeneous Example 36. This eluate was evaporated in vacuo and lyophilized overnight to give 65 mg (87.2%) of a hydrated analytical specimen of Example 36 as a white solid with consistent IR, mass and H[1]-NMR spectral data.

Analysis for $C_{26}H_{45}O_8S.Li.0.5H_2O$ (M.W.=533.65): Calc'd: C,58.51; H,8.69; S,6.0; Found: C,58.21; H,8.36; S,6.05.

IR (KBr) Spectrum: 3434 cm$^{-1}$ (strong,OH), 1714 cm$^{-1}$ (strong,C=O,ester), 1584 cm$^{-1}$ (strong,C=O,acid salt), 1311 cm$^{-1}$ (strong, SO$_2$), 1120 cm$^{-1}$ (strong, SO$_2$), etc.

Mass Spectrum: (M-H)$^-$=517, (M-2H+Li)$^+$=523, (M+Li)$^+$=525, (M+2LI-H)$^+$=531, (M+3Li-2H)$^+$=537, (M+Li+Na-H)$^+$=547, etc.

EXAMPLES 37 to 49

These examples may be prepared by following the procedures described in Example 1, but substituting the reagent shown below for methyl mercaptan in step 1-H.

| Reagent | | Compound Name |
|---|---|---|
| 37. | allyl-SH | [1S-[1α, 4aα, 7β,8β(2S*,4S*), 8aβ]]-2,2-Dimethylbutanoic acid, 3,3-bis(2-propenylthio)decahydro-7-methyl-8-[2-(tetrahydro-4-hydroxy-6-oxo-2H-pyran-2-yl)ethyl]-1-naphthalenyl ester |
| 38. | Ph-CH$_2$-SH | [1S-[1α, 4aα, 7β,8β(2S*,4S*), 8aβ]]-2,2-Dimethylbutanoic acid, 3,3-bis(benzylthio)decahydro-7-methyl-8-[2-(tetrahydro-4-hydroxy-6-oxo-2H-pyran-2-yl)ethyl]-1-naphthalenyl ester |
| 39. | cyclohexyl-SH | [1S-[1α, 4aα, 7β,8β(2S*,4S*), 8aβ]]-2,2-Dimethylbutanoic acid, 3,3-bis(cyclohexylthio)decahydro-7-methyl-8-[2-(tetrahydro-4-hydroxy-6-oxo-2H-pyran-2-yl)ethyl]-1-naphthalenyl ester |
| 40. | cyclopentyl-SH | [1S-[1α, 4aα, 7β,8β(2S*,4S*), 8aβ]]-2,2-Dimethylbutanoic acid, 3,3-bis(cyclopentylthio)decahydro-7-methyl-8-[2-(tetrahydro-4-hydroxy-6-oxo-2H-pyran-2-yl)ethyl]-1-naphthalenyl ester |
| 41. | pentafluorophenyl-SH | [1S-[1α, 4aα, 7β,8β(2S*,4S*), 8aβ]]-2,2-Dimethylbutanoic acid, 3,3-bis(pentafluorophenylthio)decahydro-7-methyl-8-[2-(tetrahydro-4-hydroxy-6-oxo-2H-pyran-2-yl)ethyl]-1-naphthalenyl ester |
| 42. | 2,3,5,6-tetrafluorophenyl-SH | [1S-[1α, 4aα, 7β,8β(2S*,4S*), 8aβ]]-2,2-Dimethylbutanoic acid, 3,3-bis(2,3,5,6-tetrafluorophenylthio)decahydro-7-methyl-8-[2-(tetrahydro-4-hydroxy-6-oxo-2H-pyran-2-yl)ethyl]-1-naphthalenyl ester |
| 43. | isopropyl-SH | [1S-[1α, 4aα, 7β,8β(2S*,4S*), 8aβ]]-2,2-Dimethylbutanoic acid, 3,3-bis(1-methyl-ethylthio)decahydro-7-methyl-8-[2-(tetrahydro-4-hydroxy-6-oxo-2H-pyran-2-yl)ethyl]-1-naphthalenyl ester |
| 44. | Cl-CH$_2$CH$_2$CH$_2$-SH | [1S-[1α, 4aα, 7β,8β(2S*,4S*), 8aβ]]-2,2-Dimethylbutanoic acid, 3,3-bis(3-chloropropylthio)decahydro-7-methyl-8-[2-(tetrahydro-4-hydroxy-6-oxo-2H-pyran-2-yl)ethyl]-1-naphthalenyl ester |
| 45. | hexyl-SH | [1S-[1α, 4aα, 7β,8β(2S*,4S*), 8aβ]]-2,2-Dimethylbutanoic acid, 3,3-bis(hexylthio)decahydro-7-methyl-8-[2-(tetrahydro-4-hydroxy-6-oxo-2H-pyran-2-yl)ethyl]-1-naphthalenyl ester |
| 46. | 2-methylbutyl-SH | [1S-[1α, 4aα, 7β,8β(2S*,4S*), 8aβ]]-2,2-Dimethylbutanoic acid, 3,3-bis(2-methylbutylthio)decahydro-7-methyl-8-[2-(tetrahydro-4-hydroxy-6-oxo-2H-pyran-2-yl)ethyl]-1-naphthalenyl ester |
| 47. | 3-methylbutyl-SH | [1S-[1α, 4aα, 7β,8β(2S*,4S*), 8aβ]]-2,2-Dimethylbutanoic acid, 3,3-bis(3-methylbutylthio)decahydro-7-methyl-8-[2-(tetrahydro-4-hydroxy-6-oxo-2H-pyran-2-yl)ethyl]-1-naphthalenyl ester |

| Reagent | | Compound Name |
|---|---|---|
| 48. | MeO₂C‿SH | [1S-[1α, 4aα, 7β,8β(2S*,4S*), 8aβ]]-2,2-Dimethylbutanoic acid, 3,3-bis[(2-methoxy-2-oxoethyl)thio]decahydro-7-methyl-8-[2-(tetrahydro-4-hydroxy-6-oxo-2H-pyran-2-yl)ethyl]-1-naphthalenyl ester |
| 49. | EtO₂C‿SH | [1S-[1α, 4aα, 7β,8β(2S*,4S*), 8aβ]]-2,2-Dimethylbutanoic acid, 3,3-bis[(2-ethoxy-2-oxoethyl)thio]decahydro-7-methyl-8-[2-(tetrahydro-4-hydroxy-6-oxo-2H-pyran-2-yl)ethyl]-1-naphthalenyl ester |

EXAMPLE 50 to 62

These examples may be prepared by following the procedures of Example 11, but substituting Example compounds 37 to 49, respectively, for Example 1.

50. [1S-[1α,4aα,7β,8β(2S*,4S*),8aβ]]-2,2-Dimethylbutanoic acid, 3-(2-propenylthio) decahydro-7-methyl-8-[2-(tetrahydro-4-hydroxy-6-oxo-2H-pyran2-yl)ethyl]-1-naphthalenyl ester.

51. [1S-[1α,4aα,7β,8β(2S*,4S*),8aβ]]-2,2-Dimethylbutanoic acid, 3-(benzylthio) decahydro-7-methyl-8-[2-(tetrahydro-4-hydroxy-6-oxo-2H-pyran-2-yl)ethyl]-1-naphthalenyl ester.

52. [1S-[1α,4aα,7β,8β(2S*,4S*),8aβ]]-2,2-Dimethylbutanoic acid, 3-(cyclohexylthio)decahydro7-methyl-8-[2-(tetrahydro-4-hydroxy-6-oxo-2H-pyran2-yl)ethyl]-1-naphthalenyl ester.

Note: "Ph" refers to phenyl, "Me" to methyl, and "Et" to ethyl.

53. [1S-[1α,4aα,7β,8β(2S*,4S*),8aβ]]-2,2-Dimethylbutanoic acid, 3-(cyclopentylthio)decahydro-7-methyl-8-[2-(tetrahydro-4-hydroxy-6-oxo-2H-pyran-2-yl)ethyl]-1-naphthalenyl ester.

Melting point: about 152° C., $[\alpha]_D^{22} = +87.1°$ (c=0.58, methanol)

TLC: $R_f$=0.45 (silica gel; 80% methylene chloride/10% acetic acid/10% methanol); developed using phosphomolybdate Microanalysis calculated for $C_{29}H_{49}LiO_6S.1H_2O$ (MW 550.70): required: C, 63.26; H, 9.33; S, 5.82; found: C, 63.00; H, 9.27; S, 6.21.

Mass spectroscopy: m/z 539 (M-H-2Li)⁺, 533 (M+Li)⁺ and 525 (M-H)⁻

54. [1S-[1α,4aα,7β,8β(2S*,4S*),8aβ]]-2,2-Dimethylbutanoic acid, 3-(pentafluorophenylthio) decahydro-7-methyl-8-[2-(tetrahidro-4-hydroxy-6-oxo-2H-pyran-2-yl)ethyl]-1-naphthalenyl ester.

55. [1S-[1α,4aα,7β,8β(2S*,4S*),8aβ]]-2,2-Dimethylbutanoic acid, 3-(2,3,5,6-tetrafluorophenylthio)decahydro-7-methyl-8-[2-(tetrahydro-4-hydroxy6-oxo-2H-pyran-2-yl)ethyl]-1-naphthalenyl ester.

56. [1S-[1α,4aα,7β,8β(2S*,4S*),8aβ]]-2,2-Dimethylbutanoic acid, 3-(1-methylethylthio)decahydro7-methyl-8-[2-(tetrahydro-4-hydroxy-6-oxo-2H-pyran2-yl)ethyl]-1-naphthalenyl ester.

57. [1S-[1α,4aα,7β,8β(2S*,4S*),8aβ]]-2,2-Dimethylbutanoic acid, 3-(3-chloropropylthio)decahydro7-methyl-8-[2-(tetrahydro-4-hydroxy-6-oxo-2H-pyran2-yl)ethyl]-1-naphthalenyl ester.

58. [1S-[1α,4aα,7β,8β(2S*,4S*),8aβ]]-2,2-Dimethylbutanoic acid, 3-(hexylthio)decahydro-7-methyl-8-[2-(tetrahydro-4-hydroxy-6-oxo-2H-pyran-2-yl)ethyl]-1-naphthalenyl ester.

59. [1S-[1α,4aα,7β,8β(2S*,4S*),8aβ]]-2,2-Dibutanoic acid, 3-(2-methylbutylthio)decahydro-7-methyl-8-[2-(tetrahydro-4-hydroxy-6-oxo-2H-pyran-2-yl)ethyl]-1-naphthalenyl ester.

60. [1S-[1α,4aα,7β,8β(2S*,4S*),8aβ]]-2,2-Dibutanoic acid, 3-(3-methylbutylthio)decahydro-7-methyl-8-[2-(tetrahydro-4-hydroxy-6-oxo-2H-pyran2-yl) ethyl]-1-naphthalenyl ester.

61. [1S-[1α,4aα,7β,8β(2S*,4S*),8aβ]]-2,2-Dibutanoic acid, 3-[(2-methoxy-2-oxoethyl)thio]decahydro-7-methyl-8-[2-(tetrahydro-4-hydroxy-6-oxo-2H-pyran-2-yl)ethyl]-1-naphthalenyl ester.

62. [1S-[1α,4aα,7β,8β(2S*,4S*),8aβ]]-2,2-Dibutanoic acid, 3-[(2-ethoxy-2-oxoethyl)thio]decahydro-7-methyl-8-[2-(tetrahydro-4-hydroxy-6-oxo-2H-pyran-2-yl) ethyl]-1-naphthalenyl ester.

EXAMPLES 63 to 75

These examples may be prepared by following the procedures of Example 13, but substituting Example compounds 50 to 62 for Example 11.

63. [1S-[1α,4aα,7β,8β(2S*,4S*),8aβ]]-2,2-Dimethylbutanoic acid, 3-(2-propenylsulfinyl)decahydro-7-methyl-8-[2-(tetrahydro-4-hydroxy-6-oxo-2H-pyran-2-yl)ethyl]-1-naphthalenyl ester.

64. [1S-[1α,4aα,7β,8β(2S*,4S*),8aβ]]-2,2-Dimethylbutanoic acid, 3-(benzylsulfinyl)decahydro7-methyl-8-[2-(tetrahydro-4-hydroxy-6-oxo-2H-pyran2-yl)ethyl]-1-naphthalenyl ester.

65. [1S-[1α,4aα,7β,8β(2S*,4S*),8aβ]]-2,2-Dimethylbutanoic acid, 3-(cyclohexylsulfinyl)decahydro7-methyl-8-[2-(tetrahydro-4-hydroxy-6-oxo-2H-pyran2-yl)ethyl]-1-naphthalenyl ester.

66. [1S-[1α,4aα,7β,8β(2S*,4S*),8aβ]]-2,2-Dimethylbutanoic acid, 3-(cyclopentylsulfinyl)decahydro-7-methyl-8-[2-(tetrahydro-4-hydroxy-6-oxo-2H-pyran-2-yl)ethyl]-1-naphthalenyl ester.

67. [1S-[1α,4aα,7β,8β(2S*,4S*),8aβ]]-2,2-Dimethylbutanoic acid, 3-(pentafluorophenylsulfinyl) decahydro-7-methyl-8-[2-(tetrahydro-4-hydroxy-6-oxo-2H-pyran-2-yl)ethyl]-1-naphthalenyl ester.

68. [1S-[1α,4aα,7β,8β(2S*,4S*),8aβ]]-2,2-Dimethylbutanoic acid, 3-(2,3,5,6-tetrafluorophenylsulfinyl)-decahydro-7-methyl-8-[2-(tetrahydro-4-hydroxy-6-oxo-2H-pyran-2-yl)ethyl]-1-naphthalenyl ester.

69. [1S-[1α,4aα,7β,8β(2S*,4S*),8aβ]]-2,2-Dimethylbutanoic acid, 3-(1-methylethylsulfinyl)decahydro-7-methyl-8-[2-(tetrahydro-4-hydroxy-6-oxo-2H-pyran-2-yl)ethyl]-1-naphthalenyl ester.

70. [1S-[1α,4aα,7β,8β(2S*,4S*),8aβ]]-2,2-Dimethylbutanoic acid, 3-(3-chloropropylsulfinyl)decahydro-7-methyl-8-[2-(tetrahydro-4-hydroxy-6-oxo-2H-pyran-2-yl)ethyl)-1-naphthalenyl ester.

71. [1S-[1α,4aα,7β,8β(2S*,4S*),8aβ]]-2,2-Dimethylbutanoic acid, 3-(hexylsulfinyl)decahydro-7-methyl-8-[2-(tetrahydro-4-hydroxy-6-oxo-2H-pyran2-yl)ethyl)-1-naphthalenyl ester.

72. [1S-[1α,4aα,7β,8β(2S*,4S*),8aβ]]-2,2-Dibutanoic acid, 3-(2-methylbutylsulfinyl)decahydro-7-methyl-8-

[2-(tetrahydro-4-hydroxy-6-oxo-2H-pyran2-yl)ethyl]-1-naphthalenyl ester.

73. [1S-[1α,4aα,7β,8β(2S*,4S*),8aβ]]-2,2-Dibutanoic acid, 3-(3-methylbutylsulfinyl)decahydro-7-methyl-8-[2-(tetrahydro-4-hydroxy-6-oxo-2H-pyran2-yl) ethyl]-1-naphthalenyl ester.

74. [1S-[1α,4aα,7β,8β(2S*,4S*),8aβ]]-2,2-Dibutanoic acid, 3-[(2-methoxy-2-oxoethyl)sulfinyl]decahydro-7-methyl-8-[2-(tetrahydro-4-hydroxy-6-oxo-2H-pyran-2-yl)ethyl]-1-naphthalenyl ester.

75. [1S-[1α,4aα,7β,8β(2S*,4S*),8aβ]]-2,2-Dibutanoic acid, 3-[(2-ethoxy-2-oxoethyl)sulfinyl]decahydro-7-methyl-8-[2-(tetrahydro-4-hydroxy-6-oxo-2H-pyran-2-yl) ethyl]-1-naphthalenyl ester.

EXAMPLES 76 TO 88

These examples may be prepared following the procedures of Example 15, but substituting Example compounds 50 to 62 for Example 11.

76. [1S-[1α,4aα,7β,8β(2S*,4S*),8aβ]]-2,2-Dimethylbutanoic acid, 3-(2-propenylsulfonyl)decahydro-7-methyl-8-[2-(tetrahydro-4-hydroxy-6-oxo-2H-pyran-2-yl)ethyl]-1-naphthalenyl ester.

77. [1S-[1α,4aα,7β,8β(2S*,4S*),8aβ]]-2,2-Dimethylbutanoic acid, 3-(benzylsulfonyl)decahydro7-methyl-8-[2-(tetrahydro-4-hydroxy-6-oxo-2H-pyran2-yl)ethyl]-1-naphthalenyl ester.

78. [1S-[1α,4aα,7β,8β(2S*,4S*),8aβ]]-2,2-Dimethylbutanoic acid, 3-(cyclohexylsulfonyl)decahydro7-methyl-8-[2-(tetrahydro-4-hydroxy-6-oxo-2H-pyran2-yl)ethyl]-1-naphthalenyl ester.

79. [1S-[1α,4aα,7β,8β(2S*,4S*),8aβ]]-2,2-Dimethylbutanoic acid, 3-(cyclopentylsulfonyl)decahydro-7-methyl-8-[2-(tetrahydro-4-hydroxy-6-oxo-2H-pyran-2-yl)ethyl]-1-naphthalenyl ester.

Melting point: about 156° C., $[\alpha]_D^{22} = +64.4°$ (c=0.72, methanol).

TLC: $R_f=0.41$ (silica gel; 80% methylene chloride/10% acetic acid/10% methanol); developed using phosphomolybdate Microanalysis calculated for $C_{29}H_{49}LiO_8S.1.49H2O$ (MW 591.50): required: C, 58.88; H, 8.86; S, 5.42; found: C, 58.58; H, 8.77; S, 5.85.

Mass spectroscopy: m/z 557 (M-H)⁻, 565 (M+Li)⁺ and 571 (M-H+2Li)⁺

80. [1S-[1α,4aα,7β,8β(2S*,4S*),8aβ]]-2,2-Dimethylbutanoic acid, 3-(pentafluorophenylsulfonyl) decahydro-7-methyl-8-[2-(tetrahydro-4-hydroxy-6-oxo2H-pyran-2-yl)ethyl]-1-naphthalenyl ester.

81. [1S-[1α,4aα,7β,8β(2S*,4S*),8aβ]]-2,2-Dimethylbutanoic acid, 3-(2,3,5,6-tetrafluorophenylsulfonyl)-decahydro-7-methyl-8-[2-(tetrahydro-4-hydroxy-6-oxo-2H-pyran-2-yl)ethyl]-1-naphthalenyl ester.

82. [1S-[1α,4aα,7β,8β(2S*,4S*),8aβ]]-2,2-Dimethylbutanoic acid, 3-(1-methylethylsulfonyl)decahydro-7-methyl-8-[2-(tetrahydro-4-hydroxy-6-oxo-2H-pyran-2-yl)ethyl]-1-naphthalenyl ester.

83. [1S-[1α,4aα,7β,8β(2S*,4S*),8aβ]]-2,2-Dimethylbutanoic acid, 3-(3-chloropropylsulfonyl)decahydro-7-methyl-8-[2-(tetrahydro-4-hydroxy-6-oxo-2H-pyran-2-yl)ethyl]-1-naphthalenyl ester.

84. [1S-[1α,4aα,7β,8β(2S*,4S*),8aβ]]-2,2-Dimethylbutanoic acid, 3-(hexylsulfonyl)decahydro-7-methyl-8-[2-(tetrahydro-4-hydroxy-6-oxo-2H-pyran2-yl)ethyl]-1-naphthalenyl ester.

85. [1S-[1α,4aα,7β,8β(2S*,4S*),8aβ]]-2,2-Dibutanoic acid, 3-(2-methylbutylsulfonyl)decahydro-7-methyl-8-[2-(tetrahydro-4-hydroxy-6-oxo-2H-pyran2-yl)ethyl]-1-naphthalenyl ester.

86. [1S-[1α,4aα,7β,8β(2S*,4S*),8aβ]]-2,2-Dibutanoic acid, 3-(3-methylbutylsulfonyl)decahydro-7-methyl-8-[2-(tetrahydro-4-hydroxy-6-oxo-2H-pyran-2-yl) ethyl]-1-naphthalenyl ester.

87. [1S-[1α,4aα,7β,8β(2S*,4S*),8aβ]]-2,2-Dibutanoic acid, 3-[(2-methoxy-2-oxoethyl)sulfonyl]decahydro-7-methyl-8-[2-(tetrahydro-4-hydroxy-6-oxo-2H-pyran-2-yl)ethyl]-1-naphthalenyl ester.

88. [1S-[1α,4aα,7β,8β(2S*,4S*),8aβ]]-2,2-Dibutanoic acid, 3-[(2-ethoxy-2-oxoethyl)sulfonyl]decahydro-7-methyl-8-[2-(tetrahydro-4-hydroxy-6-oxo-2H-pyran-2-yl) ethyl]-1-naphthalenyl ester.

EXAMPLES 89 TO 140

These examples may be prepared by following the procedures of Example 2, but substituting Example compounds 37 to 88 for Example 1.

89. [1S-[1α(βS*,ΔS*),2α,4aβ8β,8aα]]-8-(2,2-dimethyl-1-oxobutoxy)decahydro-β,Δ-dihydroxy-2-methyl-6,6-bis(2-propenylthio)-1-naphthaleneheptanoic acid, monolithium salt.

90. [1S-[1α(βS*,ΔS*),2α,4aβ8β,8aα]]-8-(2,2-dimethyl-1-oxobutoxy)decahydro-β,Δ-dihydroxy-2-methyl-6,6-bis(benzylthio)-1-naphthaleneheptanoic acid, monolithium salt.

91. [1S-[1α(βS*,ΔS*),2α,4aβ8β,8aα]]-8-(2,2-dimethyl-1-oxobutoxy)decahydro-β,Δ-dihydroxy-2-methyl-6,6-bis(cyclohexylthio)-1-naphthaleneheptanoic acid, monolithium salt.

92. [1S-[1α(βS*,ΔS*),2α,4aβ8β,8aα]]-8-(2,2-dimethyl-1-oxobutoxy)decahydro-β,Δ-dihydroxy-2-methyl-6,6-bis(cyclopentylthio)-1-naphthaleneheptanoic acid, monolithium salt.

93. [1S-[1α(βS*,ΔS*),2α,4aβ8β,8aα]]-8-(2,2-dimethyl-1-oxobutoxy)decahydro-β,Δ-dihydroxy-2-methyl-6,6-bis(pentafluorophenylthio)-1-naphthaleneheptanoic acid, monolithium salt.

94. [1S-[1α(βS*,ΔS*),2α,4aβ8β,8aα]]-8-(2,2-dimethyl-1-oxobutoxy)decahydro-β,Δ-dihydroxy-2-methyl-6,6-bis(2,3,5,6-tetrafluorophenylthio)-1-naphthaleneheptanoic acid, monolithium salt.

95. [1S-[1α(βS*,ΔS*),2α,4aβ8β,8aα]]-8-(2,2-dimethyl-1-oxobutoxy)decahydro-β,Δ-dihydroxy-2-methyl-6,6-bis(1-methylethylthio)-1-naphthaleneheptanoic acid, monolithium salt.

96. [1S-[1α(βS*,ΔS*),2α,4aβ8β,8aα]]-8-(2,2-dimethyl-1-oxobutoxy)decahydro-β,Δ-dihydroxy-2-methyl-6,6-bis(3-chloropropylthio)-1-naphthaleneheptanoic acid, monolithium salt.

97. [1S-[1α(βS*,ΔS*),2α,4aβ8β,8aα]]-8-(2,2-dimethyl-1-oxobutoxy)decahydro-β,Δ-dihydroxy-2-methyl-6,6-bis(hexylthio)-1-naphthaleneheptanoic acid, monolithium salt.

98. [1S-[1α(βS*,ΔS*),2α,4aβ8β,8aα]]-8-(2,2-dimethyl-1-oxobutoxy)decahydro-β,Δ-dihydroxy-2-methyl-6,6-bis(2-methylbutylthio)-1-naphthaleneheptanoic acid, monolithium salt.

99. [1S-[1α(βS*,ΔS*),2α,4aβ8β,8aα]]-8-(2,2-dimethyl-1-oxobutoxy)decahydro-β,Δ-dihydroxy-2-methyl-6,6-bis(3-methylbutylthio)-1-naphthaleneheptanoic acid, monolithium salt.

100. [1S-[1α(βS*,ΔS*),2α,4aβ8β,8aα]]-8-(2,2-dimethyl-1-oxobutoxy)decahydro-β,Δ-dihydroxy-2-methyl-6,6-bis[(2-methoxy-2-oxoethyl)thio]-1-naphthaleneheptanoic acid, monolithium salt.

101. [1S-[1α(βS*,ΔS*),2α,4aβ8β,8aα]]-8-(2,2-dimethyl-1-oxobutoxy)decahydro-β,Δ-dihydroxy-2-methyl-6,6-bis[(2-ethoxy-2-oxoethyl)thio]-1-naphthaleneheptanoic acid, monolithium salt.

102. [1S-[1α(βS*,ΔS*),2α,4aβ8β,8aα]]-8-(2,2-dimethyl-1-oxobutoxy)decahydro-β,Δ-dihydroxy-2-methyl-6-(2-propenylthio)-1-naphthaleneheptanoic acid, monolithium salt.

103. [1S-[1α(βS*,ΔS*),2α,4aβ8β,8aα]]-8-(2,2-dimethyl-1-oxobutoxy)decahydro-β,Δ-dihydroxy-2-methyl-6-(benzylthio)-1-naphthaleneheptanoic acid, monolithium salt.

104. [1S-[1α(βS*,ΔS*),2α,4aβ8β,8aα]]-8-(2,2dimethyl-1-oxobutoxy)decahydro-β,Δ-dihydroxy-2-methyl-6-(cyclohexylthio)-1-naphthaleneheptanoic acid, monolithium salt.

105. [1S-[1α(βS*,ΔS*),2α,4aβ8β,8aα]]-8-(2,2dimethyl-1-oxobutoxy)decahydro-β,Δ-dihydroxy-2-methyl-6-(Cyclopentylthio)-1-naphthaleneheptanoic acid, monolithium salt.

106. [1S-[1α(βS*,ΔS*),2α,4aβ8β,8aα]]-8-(2,2-dimethyl-1-oxobutoxy)decahydro-β,Δ-dihydroxy-2-methyl-6-(pentafluorophenylthio)-1-naphthaleneheptanoic acid, monolithium salt.

107. [1S-[1α(βS*,ΔS*),2α,4aβ8β,8aα]]-8-(2,2-dimethyl-1-oxobutoxy)decahydro-β,Δ-dihydroxy-2-methyl-6-(2,3,5,6-tetrafluorophenylthio)-1-naphthaleneheptanoic acid, monolithium salt.

108. [1S-[1α(βS*,ΔS*),2α,4aβ8β,8aα]]-8-(2,2-dimethyl-1-oxobutoxy)decahydro-βΔ-dihydroxy-2-methyl-6-(1-methylethylthio)-1-naphthaleneheptanoic acid, monolithium salt.

109. [1S-[1α(βS*,ΔS*),2α,4aβ8β,8aα]]-8-(2,2dimethyl-1-oxobutoxy)decahydro-β,Δ-dihydroxy-2-methyl-6-(3-chloropropylthio)-1-naphthaleneheptanoic acid, monolithium salt.

110. [1S-[1α(βS*, ΔS*), 2α,4aβ, 8β, 8aα]]-8-(2,2-dimethyl-1-oxobutoxy)decahydro-β,Δ-dihydroxy-2-methyl-6-(hexylthio)-1-naphthaleneheptanoic acid, monolithium salt.

111. [1S-[1α(βS*, ΔS*), 2α,4aβ, 8β, 8aα]]-8-(2,2-dimethyl-1-oxobutoxy)decahydro-β,Δ-dihydroxy-2-methyl-6-(2-methylbutylthio)-1-naphthaleneheptanoic acid, monolithium salt.

112. [1S-[1α(βS*, ΔS*), 2α,4aβ, 8β, 8aα]]-8-(2,2-dimethyl-1-oxobutoxy)decahydro-β,Δ-dihydroxy-2-methyl-6-(3-methylbutylthio)-1-naphthaleneheptanoic acid, monolithium salt.

113. [1S-[1α(βS*, ΔS*), 2α,4aβ, 8β, 8aα]]-8-(2,2-dimethyl-1-oxobutoxy)decahydro-β,Δ-dihydroxy-2-methyl-6-[(2-methoxy-2-oxoethyl)thio]-1-naphthaleneheptanoic acid, monolithium salt.

114. [1S-[1α(βS*, ΔS*), 2α,4aβ, 8β, 8aα]]-8-(2,2-dimethyl-1-oxobutoxy)decahydro-β,Δ-dihydroxy-2-methyl-6-[(2-ethoxy-2-oxoethyl)thio]-1-naphthaleneheptanoic acid, monolithium salt.

115. [1S-[1α(βS*, ΔS*), 2α,4aβ, 8β, 8aα]]-8-(2,2-dimethyl-1-oxobutoxy)decahydro-β,Δ-dihydroxy-2-methyl-6-(2-propenylsulfinyl)-1-naphthaleneheptanoic acid, monolithium salt.

116. [1S-[1α(βS*, ΔS*), 2α,4aβ, 8β, 8aα]]-8-(2,2-dimethyl-1-oxobutoxy)decahydro-β,Δ-dihydroxy-2-methyl-6-(benzylsulfinyl)-1-naphthaleneheptanoic acid, monolithium salt.

117. [1S-[1α(βS*, ΔS*), 2α,4aβ, 8β, 8aα]]-8-(2,2-dimethyl-1-oxobutoxy)decahydro-β,Δ-dihydroxy-2-methyl-6-(cyclohexylsulfinyl)-1-naphthaleneheptanoic acid, monolithium salt.

118. [1S-[1α(βS*, ΔS*), 2α,4aβ, 8β, 8aα]]-8-(2,2-dimethyl-1-oxobutoxy)decahydro-β,Δ-dihydroxy-2-methyl-6-(cyclopentylsulfinyl)-1-naphthaleneheptanoic acid, monolithium salt.

119. [1S-[1α(βS*, ΔS*), 2α,4aβ, 8β, 8aα]]-8-(2,2-dimethyl-1-oxobutoxy)decahydro-β,Δ-dihydroxy-2-methyl-6-(pentafluorophenylsulfinyl)-1-naphthaleneheptanoic acid, monolithium salt.

120. [1S-[1α(βS*, ΔS*), 2α,4aβ, 8β, 8aα]]-8-(2,2-dimethyl-1-oxobutoxy)decahydro-β,Δ-dihydroxy-2-methyl-6-(2,3,5,6-tetrafluorophenylsulfinyl)-1-naphthaleneheptanoic acid, monolithium salt.

121. [1S-[1α(βS*, ΔS*), 2α,4aβ, 8β, 8aα]]-8-(2,2-dimethyl-1-oxobutoxy)decahydro-β,Δ-dihydroxy-2-methyl-6-(1-methylethylsulfinyl)-1-naphthaleneheptanoic acid, monolithium salt.

122. [1S-[1α(βS*, ΔS*), 2α,4aβ, 8β, 8aα]]-8-(2,2-dimethyl-1-oxobutoxy)decahydro-β,Δ-dihydroxy-2-methyl-6-(3-chloropropylsulfinyl)-1-naphthaleneheptanoic acid, monolithium salt.

123. [1S-[1α(βS*, ΔS*), 2α,4aβ, 8β, 8aα]]-8-(2,2-dimethyl-1-oxobutoxy)decahydro-β,Δ-dihydroxy-2-methyl-6-(hexylsulfinyl)-1-naphthaleneheptanoic acid, monolithium salt.

124. [1S-[1α(βS*, ΔS*), 2α,4aβ, 8β, 8aα]]-8-(2,2-dimethyl-1-oxobutoxy)decahydro-β,Δ-dihydroxy-2-methyl-6-(2-methylbutylsulfinyl)-1-naphthaleneheptanoic acid, monolithium salt.

125. [1S-[1α(βS*, ΔS*), 2α,4aβ, 8β, 8aα]]-8-(2,2-dimethyl-1-oxobutoxy)decahydro-β,Δ-dihydroxy-2-methyl-6-(3-methylbutylsulfinyl)-1-naphthaleneheptanoic acid, monolithium salt.

126. [1S-[1α(βS*, ΔS*), 2α,4aβ, 8β, 8aα]]-8-(2,2-dimethyl-1-oxobutoxy)decahydro-β,Δ-dihydroxy-2-methyl-6-[(2-methoxy-2-oxoethyl)sulfinyl]-1-naphthaleneheptanoic acid, monolithium salt.

127. [1S-[1α(βS*, ΔS*), 2α,4aβ, 8β, 8aα]]-8-(2,2-dimethyl-1-oxobutoxy)decahydro-β,Δ-dihydroxy-2-methyl-6-[(2-ethoxy-2-oxoethyl)sulfinyl]-1-naphthaleneheptanoic acid, monolithium salt.

128. [1S-[1α(βS*, ΔS*), 2α,4aβ, 8β, 8aα]]-8-(2,2-dimethyl-1-oxobutoxy)decahydro-β,Δ-dihydroxy-2-methyl-6-(2-propenylsulfonyl)-1-naphthaleneheptanoic acid, monolithium salt.

129. [1S-[1α(βS*, ΔS*), 2α,4aβ, 8β, 8aα]]-8-(2,2-dimethyl-1-oxobutoxy)decahydro-β,Δ-dihydroxy-2-methyl-6-(benzylsulfonyl)-1-naphthaleneheptanoic acid, monolithium salt.

130. [1S-[1α(βS*, ΔS*), 2α,4aβ, 8β, 8aα]]-8-(2,2-dimethyl-1-oxobutoxy)decahydro-β,Δ-dihydroxy-2-methyl-6-(cyclohexylsulfonyl)-1-naphthaleneheptanoic acid, monolithium salt.

131. [1S-[1α(βS*, ΔS*), 2α,4aβ, 8β, 8aα]]-8-(2,2-dimethyl-1-oxobutoxy)decahydro-β,Δ-dihydroxy-2-methyl-6-(cyclopentylsulfonyl)-1-naphthaleneheptanoic acid, monolithium salt.

132. [1S-[1α(βS*, ΔS*), 2α,4aβ, 8β, 8aα]]-8-(2,2-dimethyl-1-oxobutoxy)decahydro-β,Δ-dihydroxy-2-methyl-6-(pentafluorophenylsulfonyl)-1-naphthaleneheptanoic acid, monolithium salt.

133. [1S-[1α(βS*, ΔS*), 2α,4aβ, 8β, 8aα]]-8-(2,2-dimethyl-1-oxobutoxy)decahydro-β,Δ-dihydroxy-2-methyl-6-(2,3,5,6-tetrafluorophenylsulfonyl)-1-naphthaleneheptanoic acid, monolithium salt.

134. [1S-[1α(βS*, ΔS*), 2α,4aβ, 8β, 8aα]]-8-(2,2-dimethyl-1-oxobutoxy)decahydro-β,Δ-dihydroxy-2-methyl-6-(1-methylethylsulfonyl)-1-naphthaleneheptanoic acid, monolithium salt.

135. [1S-[1α(βS*, ΔS*), 2α,4aβ, 8β, 8aα]]-8-(2,2-dimethyl-1-oxobutoxy)decahydro-β,Δ-dihydroxy-2-methyl-6-(3-chloropropylsulfonyl)-1-naphthaleneheptanoic acid, monolithium salt.

136. [1S-[1α(βS*, ΔS*), 2α,4aβ, 8β, 8aα]]-8-(2,2-dimethyl-1-oxobutoxy)decahydro-β,Δ-dihydroxy-2-methyl-6-(hexylsulfonyl)-1-naphthaleneheptanoic acid, monolithium salt.

137. [1S-[1α(βS*, ΔS*), 2α,4aβ, 8β, 8aα]]-8-(2,2-dimethyl-1-oxobutoxy)decahydro-β,Δ-dihydroxy-2-methyl-6-(2-methylbutylsulfonyl)-1-naphthaleneheptanoic acid, monolithium salt.

138. [1S-[1α(βS*, ΔS*), 2α,4aβ, 8β, 8aα]]-8-(2,2-dimethyl-1-oxobutoxy)decahydro-β,Δ-dihydroxy-2-methyl-6-(3-methylbutylsulfonyl)-1-naphthaleneheptanoic acid, monolithium salt.

139. [1S-[1α(βS*, ΔS*), 2α,4aβ, 8β, 8aα]]-8-(2,2-dimethyl-1-oxobutoxy)decahydro-β,Δ-dihydroxy-2-methyl-6-[(2-methoxy-2-oxoethyl)sulfonyl]-1-naphthaleneheptanoic acid, monolithium salt.

140. [1S-[1α(βS*, ΔS*), 2α,4aβ, 8β, 8aα]]-8-(2,2-dimethyl-1-oxobutoxy)decahydro-β,Δ-dihydroxy-2-methyl-6-[(2-ethoxy-2-oxoethyl)sulfonyl]-1-naphthaleneheptanoic acid, monolithium salt.

EXAMPLE 141

[1S-[1α(βS*, ΔS*), 2α,4aβ, 8β, 8aα]]-8-(2,2-Dimethyl-1-oxobutoxy)decahydro-β,Δ-dihydroxy-2-methyl-6-[(2-methylpropyl)thio]-1-naphthaleneheptanoic acid, monolithium salt.

This example was prepared following the procedures of Examples 1 and 11, but substituting 2-methylpropylthiol for methyl mercaptan in step 1-H.

Melting point: about 162° C., $[\alpha]_D^{22} = 100.3°$, (c=0.58, methanol)

TLC: $R_f = 0.56$ (silica gel; 80% methylene chloride/10% acetic acid/10% methanol); developed using phosphomolybdate.

Microanalysis calculated for $C_{28}H_{49}LiO_6S.0.5H_2O$ (MW 529.71) required: C, 63.50; H, 9.51; S, 6.05; found: C, 63.26; H, 9.62; S, 5.98. Mass spectroscopy: m/z 527 $(M-H+2Li)^+$, 521 $(M+Li)^+$, 519 $(M-2H+Li)^-$ and 513 $(M-H)^-$

EXAMPLE 142

1S-[1α(βS*, ΔS*), 2α,4aβ, 8β, 8aα]]-8-(2,2-Dimethyl-1-oxobutoxy)-6-[(fluoromethyl)sulfinyl]decahydro-β, Δ-dihydroxy-2-methyl-1-naphthaleneheptanoic acid, monolithium salt 142-A. [1S-[1α, 3α,4aα, 7β, 8β (2S*, 4S*), 8aβ]]-2,2-Dimethylbutanoic acid, 8-[2-[4-[[(1,1-dimethylethyl)-dimethylsilyl]oxy]tetrahydro-6-oxo-2H-pyran-2-yl]ethyl]decahydro-7-methyl-3-(methylthio)-1-naphthalenyl ester A solution of the sulphide Example 11 (800 mg, 1.76 mmol) and imidazole (264 mg, 3.87 mmol) in dimethylformamide (5 mL) was treated with t-butyldimethylsilyl chloride (318 mgs, 2.11 mmol) and stirred at room temperature for 12 hours. The reaction mixture was treated with water (10 mL)/ethyl acetate (60 mL) and shaken well. The organic layer was removed and the aqueous layer extracted with ethyl acetate (2×10 mL), the combined organic fractions were dried (magnesium sulfate) and the solvent removed by evaporation to give an oil, which was purified by column chromatography on silica gel using 20% ethyl acetate/80% hexane as the mobile phase to give compound 142-A (897 mg, 90%) as a white foam.

TLC: $R_f = 0.69$ (silica gel; 50% ethyl acetate/50% hexane); developed using phosphomolybdate.

142-B.[1S-[1α, 3α,4aα, 7β, 8β(2S*, 4S*), 8aβ]]-2,2-Dimethylbutanoic acid, 8-[2-[4-[[(1,1-dimethylethyl)-dimethylsilyl]oxy]tetrahydro-6-oxo-2H-pyran-2-yl]ethyl]decahydro-7-methyl-3-(methylsulfinyl)-1-naphthalenyl ester A solution of sulphide 142-A (890 mg, 1.56 mmol) in methylene chloride (10 mL) was treated with a solution of 85% m-chloroperoxybenzoic acid (318 mg, 1.56 mmol) in methylene chloride (20 mL) added dropwise, with stirring. The reaction was washed with saturated aqueous sodium hydrogen carbonate (10 mL) and brine (10 mL), dried (magnesium sulfate) and the solvent was removed by evaporation to give an oil/foam; which was purified by column chromatography on silica gel using 1) 80% ethyl acetate/20% hexane and 2) 100% ethyl acetate as the mobile phase to give the mixture of sulfoxides 142-B (889 mg, 97%) as a white foam/oil.

TLC: $R_f = 0.10$ (silica gel; 80% ethyl acetate/20% hexane); developed using phosphomolybdate.

Microanalysis calculated for $C_{31}H_{56}O_6SSi.0.42H_2O$ (MW 592.47): required: C, 62.84; H, 9.67; S, 5.41; found: C, 62.84; H, 9.66; S, 5.68.

IR (KBr pellet) 3465 cm$^{-1}$ (OH) and 1724 cm$^{-1}$ (C=O) Mass spectroscopy: M/z 585 $(M+H)^+$ and 583 $(M-H)^-$ 142-C. [1S-[1α, 3α,4aα, 7β, 8β(2S*, 4S*), 8aβ]]-2-Dimethylbutanoic acid, 3-[(fluoromethyl)thio]decahydro-7-methyl-8-[2-(tetrahydro-4-hydroxy-6-oxo-2H-pyran-2-yl)ethyl]-1-naphthalenyl ester A solution of the sulphoxides 142-B (880 mg, 1.50 mmol) and zinc iodide (5 mg) in methylene chloride (5 mL) was treated with diethylamino-sulfur trifluoride (298 μL, 2.26 mmol, see JACS 107, 1985, 735) and stirred at room temperature for 12 hours. The solvent was removed by evaporation to give an oil, which was purified by column chromatography on silica gel using 50% ethyl acetate/50% hexane as the mobile phase to give a fluoro compound (539 mg, 61%) as a pale yellow foam.

A solution of the fluoro compound (512 mg, 0.872 mmol) and acetic acid (207 μL, 3.490 mmol) in tetrahydrofuran (5 mL) was treated with a 1.0M solution of tetra-n-butylammonium fluoride in tetrahydrofuran (1.74 mL, 1.745 mmol) and stirred at room temperature for 24 hours. The reaction mixture was partioned between ethyl acetate (60 mL) and saturated aqueous sodium hydrogen carbonate (5 mL) and shaken well. The aqueous layer was removed and the organic solution was washed with brine (10 mL) and dried (sodium sulfate). The solvent was removed by evaporation to give an oil, which was purified by column chromatography on silica gel using 50% ethyl acetate/50% hexane as the mobile phase to give fluorosulphide 142-C (250 mg, 61%) as a clear colorless oil.

TLC: $R_f = 0.25$ (silica gel; 50% ethyl acetate/50% hexane); developed using phosphomolybdate.

142-D. [1S-[1α, 3α,4aα, 7β, 8β(2S*, 4S*), 8aβ]]-2,2-Dimethylbutanoic acid, 3-[(fluoromethyl)sulfinyl]-decahydro-7-methyl-8-[2-(tetrahydro-4-hydroxy-6-oxo-2H-pyran-2-yl)ethyl]-1-naphthalenyl ester A solution of the fluorosulphide 142-C (242 mg, 0.512 mmol) in methylene chloride (2 mL) was treated with a solution of 85% m-chloroperoxybenzoic acid (114 mgs, 0.563 mmol) in methylene chloride (10 mL) added dropwise, with stirring. The reaction mixture was diluted with methylene chloride (30 mL), washed with saturated aqueous sodium hydrogen carbonate (5 mL), dried (sodium sulfate) and the solvent removed by evaporation to give an oil. This oil was purified by column chromatography on silica gel using 1) 100% ethyl acetate 2) 4% isopropyl alcohol/96% ethyl acetate as the mobile phase to give the fluorosulphoxides 142-D (171 mg, 68%) as a white foam.

TLC: $R_f$=0.15 (silica gel; 81% ethyl acetate); developed using phosphomolybdate.

142-E. [1S-[1α(βS*, ΔS*),2α,4aβ,8β, 8aα]]-8-(2,2-Dimethyl-1-oxobutoxy)-6-[(fluoromethyl)sulfinyl]-decahydro-β, Δ-dihydroxy-2-methyl-1-naphthaleneheptanoic acid, monolithium salt A solution of the fluorosulphoxides 142-D (168 mg, 0.342 mmol) in tetrahydrofuran (5 mL), under argon, was treated with 1N aqueous lithium hydroxide (684 μL, 0.684 mmol) and stirred at room temperature for 0.5 hours. The solvent was removed by evaporation and the residue placed on a HP20/water column, using water. The column was eluted with 1) 100% water and 2) 10% acetonitrile/90% water. The fractions containing the product were concentrated by evaporation, dissolved in water (10 mL), filtered through a 3 μm cellulose nitrate membrane filter and the water was removed by freeze-drying to give Example 142 (141 mg, 78%) as a white lyophilate.

Melting point: about 145° C., $[α]_D^{22}$=+54.0° [c=0.52, methanol].

TLC: $R_f$=0.41 (silica gel; 80% methylene chloride/10% acetic acid/10% methanol); developed using phosphomolybdate. Microanalysis calculated for $C_{25}H_{42}FLiO_7S.1H_2O$ (MW 530.59) required: C, 56.59; H, 8.36; F, 3.58; S, 6.04; found: C, 56.96; H, 8.43; F, 3.31; S, 5.98.

IR (KBr pellet): 3427 cm$^{-1}$ (OH) and 1716 cm$^{-1}$ (C=O). Mass spectroscopy: m/z 519 (M−H+2Li)+, 513 (M+Li)+, 507 (M+H)+ and 505 (M−H)−

EXAMPLE 143

[1S-[1α,(βS*, ΔS*),2α,4aβ,6β(S*),8β, 8aα]-8-(2,2-Dimethyl-1-oxobutoxy)-6-[(fluoromethyl)-sulphinyl]-decahydro-β, Δ-dihydroxy-2-methyl-1-naphthalene-heptanoic acid, monolithium salt, minor isomer 143-A. [1S-[1α,3α(R*),4aα,7β,8β(2S*,4S*),8aβ]]-2,2-Dimethylbutanoic acid, 3-[(fluoromethyl)sulfinyl]-decahydro-7-methyl-8-[2-(tetrahydro-4-hydroxy-6-oxo-2H-pyran-2-yl)ethyl]-1-naphthalenyl ester; and 143-B. [1S-[1α,3α(S*),4aα,7β,8β(2S*,4S*),8aβ]]-2,2-Dimethylbutanoic acid, 3-[(fluoromethyl)sulfinyl]-decahydro-7-methyl-8-[2-(tetrahydro-4-hydroxy-6-oxo-2H-pyran-2-yl)ethyl]-1-naphthalenyl ester A solution of the silyl compound 142-B (214 mg, 0.355 mmol) in tetrahydrofuran (2 mL) and acetic acid (81 mL, 1.420 mmol) was treated with a 1.0M solution of tetra-n-butylammonium fluoride in tetrahydrofuran (710 μl, 0.710 mmol) and stirred at room temperature for 24 hours. The reaction mixture was treated with ethyl acetate (60 mL)/saturated sodium hydrogen carbonate (5 mL), shaken well and the aqueous layer was removed. The organic layer was washed with brine (10 mL) and the solvent was removed by evaporation to give an oil, which was dried (magnesium sulfate) and purified by column chromatography on silica gel using 1) 85% ethyl acetate/15% hexane 2) 95% ethyl acetate/5% hexane as the mobile phase.

|  | Minor Isomer Faster-Moving Spot (Compound 143-A) | Major Isomer, Slower-Moving Spot (Compound 143-B) |
|---|---|---|
| appearance | crystalline cubes | crystalline needles |
| yield | 50 mg | 75 mg, |
| % theoretical | 29% | 43%, single crystal x-ray analysis |
| NMR | 400 MHz | 400 MHz |
| Mass Spec. m/z | 489 (M + H)+ | 489 (M + H)+ |

143-C. [1S-[1α,(βS*,ΔS*),2α,4aβ,6β(S*),8β,8aα]-8-(2,2-Dimethyl-1-oxobutoxy)-6-[(fluoromethyl)sulphinyl]decahydro-β,Δ-dihydroxy-2-methyl-1-naphthaleneheptanoic acid, monolithium salt, minor isomer A solution of the lactone 143-A (48 mg, 0.10 mmol) in acetonitrile (2 mL) was treated with 1N aqueous lithium hydroxide (196 μL, 0.196 mmol) and stirred at room temperature for ½ hour. The solvent was removed by evaporation and the residue, in water, placed on a CHP-20P/water column. The column was eluted with 1) water to remove excess lithium hydroxide and 2) 15% acetonitrile/85% water.

The solvent was removed by evaporation, the residue dissolved in water and filtered through a 0.3 μm cellulose nitrate membrane filter, and the solvent removed by freeze-drying.

EXAMPLE 143 appearance—white/pale yellow solid
yield—44 mg
% theoretical—85%
NMR—400 MHz
Mass Spectroscopy—m/z 507 (M+H)+
Rotation—$[α]_D^{22}$ = +78.8° (c=0.60, methanol)
Microanalysis calculated for $C_{25}H_{42}FLiO_7S.0.80.H_2O$ (MW 526.99) required: C, 56.97; H, 8.34; F, 3.60; S, 6.08; found: C, 56.97; H, 8.41; F, 3.40; S, 5.84.

EXAMPLE 144

[1S-[1α, (βS*, ΔS*), 2α,4aβ, 6β(R*), 8β, 8aα]-8-(2,2-Dimethyl-1-oxobutoxy)-6-[(fluoromethyl)-sulphinyl]-decahydro-β, Δ-dihydroxy-2-methyl-1-naphthaleneheptanoic acid, monolithium salt A solution of compound 143-B (70 mg, 0.143 mmol) in tetrahydrofuran (1 mL)/acetonitrile (1 mL) was treated with 1N aqueous lithium hydroxide (287 mL, 0.287 mmol) and stirred at room temperature for 1 hour. The solvent was removed by evaporation and the residue dissolved in water and placed on a CHP-20P/water column. The column was eluted with 1) water to remove excess lithium hydroxide 2) 5% acetonitrile/95% water (no compound eluted) 3) 10% acetonitrile/90% water.

The solvent was removed by evaporation, the residue dissolved in water and filtered through a 0.3 μm cellulose nitrate membrane filter, and the solvent removed by freeze-drying.

EXAMPLE 144 appearance—white lyophilate
yield—47 mg
% theoretical—61%

NMR—400 MHz m. spec—m/z 507 $(M+H)^+ [\alpha]_D^{22} = +34.8°$ (C=0.29, methanol).

Microanalysis calculated for $C_{25}H_{42}FLiO_7S \cdot 1.43H_2O$ (MW 538.34) required: C, 55.77; H, 8.40; F, 3.53; S, 5.95; found: C, 55.77; H, 8.34; F, 3.44; S, 5.73.

EXAMPLE 145

[1S-[1α, (βS*, ΔS*), 2α,4aβ, 6β(R*), 8β, 8aα]-8-(2,2-Dimethyl-1-oxobutoxy)decahydro-β, Δ-dihydroxy-2-methyl-6-(methylsulfinyl)-1-naphthaleneheptanoic acid, monolithium salt 145-A. [1S-[1α,3α(R*),4aα,7β,8β(2S*,4S*),8aβ]]-2,2-Dimethylbutanoic acid, decahydro-7-methyl-3-(methylsulfinyl)-8-[2-(tetrahydro-4-hydroxy-6-oxo-2H-pyran-2-yl)ethyl]-1-naphthalenyl ester A mixture of the diastereomeric sulphoxides Example 14 (535 mg) was separated by reverse phase HPLC ($C_{18}$ Novapak) separation using 40% acetonitrile/60% water. The fractions containing compound 145-A were concentrated by evaporation to remove acetonitrile and extracted with ethyl acetate (3×50 mL). The combined organic fractions were washed with brine (50 mL), dried (magnesium sulphate) and the solvent was removed by evaporation to give compound 145-A (190 mg) as a white solid.

145-B. [1S-[1α(βS*,ΔS*,2α,4aβ,6β(R*),8β, 8aα]-8-(2,2-Dimethyl-1-oxobutoxy)decahydro-β, Δ-dihydroxy-2-methyl-6-(methylsulfinyl)-1-naphthaleneheptanoic acid, monolithium salt A solution of the sulfoxide 145A (190 mg, 0.404 mmol) in tetrahydrofuran (8 mL), under argon, was treated with 1N aqueous lithium hydroxide (807 mL, 0.807 mmol) and stirred at room temperature for 1 hour, 40 mLnutes. The solvent was removed by evaporation and the residue placed on a CHP-20P/water column, using water. The column was eluted with 1) 100% water and 2) 20% acetonitrile/80% water. The fractions containing the product were concentrated by evaporation, dissolved in water (10 mL), filtered through a 0.3 μm cellulose nitrate membrane filter and the water was removed by freeze-drying to give Example 145 (143 mg, 70%) as a white lyophilate, $[a]_D^{22} = 82.5°$ (c=0.71, methanol).

TLC: $R_f = 0.22$ (silica gel; 80% methylene chloride/10% acetic acid/10% methanol); developed using phosphomolybdate Microanalysis calculated for $C_{25}H_{43}LiO_7S \cdot 0.75H_2O$ (MW 508.12): required: C, 59.10; H, 8.83; S, 6.31; found: C, 59.19; H, 8.91; S, 6.69.

IR (KBr pellet): 3414 cm$^{-1}$ (OH) and 1716 cm$^{-1}$ (C=O).

Mass spectroscopy: m/z, 501 $(M+2Li-H)^+$, 495 $(M+Li)^+$, 493 $(M-2H-Li)^-$ and 487 $(M-H)^-$.

EXAMPLE 146

[1S-[1α(βS*,ΔS*),2α,4aβ,6β(S*),8β, 8aα]]-8-(2,2-Dimethyl-1-oxopropoxy)decahydro-β, Δ-dihydroxy-2-methyl-6-(methylsulfinyl)-1-naphthaleneheptanoic acid, monolithium salt The procedures of Example 145 were repeated, except that step A was used to isolate fractions containing [1S-[1α,3α(S*),4aα,7β, 8β(2S*, 4S*),8aβ]]-2,2-dimethylbutanoic acid, decahydro-7-methyl-3-(methylsulfinyl)-8-[2-(tetrahydro-4-hydroxy-6-oxo-2H-pyran-2-yl)ethyl]-1-naphthalenyl ester.

TLC for example compound 146: $R_f = 0.17$ (silica gel; 80% methylene chloride/10% acetic acid/10% methanol); developed using phosphomolybdate.

Microanalysis calculated for Example 146, $C_{25}H_{43}LiO_7S \cdot 0.75H_2O$ (MW 508.12) required: C, 59.10; H, 8.83; S, 6.31; found: C, 59.29; H, 8.73; S, 6.64.

IR (KBr pellet): 3420 cm$^{-1}$ 1 (OH) and 1716 cm$^{-1}$ 1 (C=O).

Mass spectroscopy: m/z, 501 $(M+2Li-H)^+$, 495 $(M+Li)^+$, 493 $(M-2H+Li)^-$ and 487 $(M-H)^-$

Example 147

[1S-[1α,4aα,7β, 8β(2S*,4S*),8aβ]]-2-Methylbutanoic acid, 3,3-bis(methylthio)decahydro-7-methyl-8-[2-(tetrahydro-4-hydroxy-6-oxo-2H-pyran-2-yl)ethyl]-1-naphthalenyl ester The procedures of Example 1 were followed, excluding the methylation step 1-C.

appearance: white, flat crystals
yield: 1.297 g, 3.143 mmol
% theoretical: 93% (starting from 23.04 g, 43.91 mmol of compound 1-A).

EXAMPLE 148

[1S-[1α(βS*,ΔS*),2α,3aβ, 8β, 8aβ,]]-8-(2,2-Dimethyl-1-oxobutoxy)decahydro-β, Δ-dihydroxy-2-methyl-6-(methylsulfinyl)-1-naphthaleneheptanoic acid, monolithium salt This example was prepared by following the procedures of Example 1, but substituting 2-mercaptoethanol for methyl mercaptan in step 1-H.

appearance: white lyophilate
yield: 246 mg
% theoretical: 78.6%
NMR—300 MHz ($CD_3OD$)
Mass Spectroscopy—m/z 577 $(M-H)^-$
Rotation—$[\alpha]_D^{22} = +42.8°$ (c=0.56, methanol) Microanalysis calculated for $C_{28}H_{49}O_8S_2Li \cdot O \cdot H_2O$ (MW 602.77) required: C, 55.79; H, 8.53; S, 10.64; found: C, 55.77; H, 8.59; S, 10.86.

EXAMPLE 149

1S-[1α(βS*,ΔS*),2α,4aβ,6β, 8β, 8aα]]-8-(2,2-Dimethyl-1-oxobutoxy)decahydro-β, Δ-dihydroxy-6-(2-hydroxyethyl)thio]-2-methyl-1-naphthaleneheptanoic acid, monolithium salt This example was prepared by following the procedures of Example 11, but substituting Example 148 for Example 1.

appearance: white lyophilate yield: 137 mg, 0.269 mmol 0% theoretical: 74% rotation: $[\alpha]_D^{22} = (0.253, 3.0$ mg) = 84.3° (0.366,4.3 mg) = 85.1°.

EXAMPLES 150 to 151

These examples were prepared by following the procedure of Example 13, but substituting Examples 147 and 149, respectively, for Example 11.

150. [1S-[1α(βS*,ΔS*),2α,4aβ,6β, 8β, (R*), 8aα]]-Decahydro-β, Δ-dihydroxy-2-methyl-8-(2-methyl-1-oxobutoxy)-6-(methylsulfinyl)-1-naphthaleneheptanoic acid, monolithium salt appearance: white lyophilate
theoretical: 63%
yield: 103 mg
NMR: 300 MHz ($CD_3OD$)

Mass Spectroscopy: m/z 475 (M+H)+ rotation: $[\alpha]_D^{22} = +64.2°$ (c=0.48, methanol) Microanalysis calculated for $C_{24}H_{41}O_7SLi.1.25H_2O$ (MW 503.11) required: C, 57.31; H, 8.71; S, 6.37; found: C, 57.18; H, 8.68; S, 6.72. % theoretical: 63%

151. [1S-[1α(βS*,ΔS*),2α,4aβ,6β, 8β, 8aα]]-8-(2,2-Dimethyl-1-oxobutoxy)decahydro-β, Δ-dihydroxy-6-[(2-hydroxyethyl)sulfinyl]-2-methyl-1-naphthaleneheptanoic acid, monolithium salt appearance: white lyophilate
yield: 238 mg, 0.454 mmol
% theoretical: 87.4%

NMR: 300 MHz (CD3OD) Mass Spectroscpy: m/z 517 (M−H)− rotation: $[\alpha]_D^{22} = +50.0°$ (c=0.46, methanol) Microanalysis calculated for $C_{24}H_{45}O_8SLi.0.96\text{-}H_2O$ required: C, 57.63; H, 8.73; S, 5.92; found: C, 57.63; H, 8.92; S, 5.98.

EXAMPLES 152 TO 155

These examples were prepared by following the procedures of Example 15, but substituting Examples 141, 142, 147 and 149, respectively, for Example 11.

152. [1S-[1α(βS*,ΔS*),2α,4aβ,6β, 8β, 8aα]]-8-(2,2-Dimethyl-1-oxobutoxy)decahydro-β, Δ-dihydroxy-2-(2-methylpropyl)sulfonyl]-1-naphthaleneheptanoic acid, monolithium salt 153. [1S-[1α(βS*,ΔS*),2α,4aβ,6β, 8β, 8aα]]-8-(2,2-Dimethyl-1-oxobutoxy)-6-[(fluoromethyl)sulfonyl]-decahydro-β, Δ-dihydroxy-2-methyl-1-naphthaleneheptanoic acid, monolithium salt 154. [1S-[1α(βS*,ΔS*),2α,4aβ,6β, 8β, (R*), 8aα]]-Decahydro-β, Δ-dihydroxy-2-methyl-8-(2-methyl-1-oxobutoxy)-6-methylsulfonyl)-1-naphthaleneheptanoic acid, monolithium salt 155. [1S-[1α(βS*,ΔS*),2α,4aβ,6β, 8β, 8aα]]-8-(2,2-Dimethyl-1-oxobutoxy)decahydro-β, Δ-dihydroxy-6-[(2-hydroxyethyl)sulfonyl]-2-methyl-1-naphthaleneheptanoic acid, monolithium salt

EXAMPLE 156

[1α,4aα, 7β, 8β(2S*, 4S*), 8aβ]]-2,2-Dimethylbutanoic acid, 3,3-bis(cyclopentylsulfinyl)decahydro-7-methyl-8-[2-(tetrahydro-4-hydroxy-6-oxo-2H-pyran-2-yl]ethyl]-1-naphthalenyl ester This example was prepared by following the procedures of Example 1, substituting cyclopentyl mercaptan for methyl mercaptan in step 1-H.

TLC: R$_f$=0.22 (silica gel; 50% ethyl acetate/50% hexane), developed using phosphomolybdate.

EXAMPLE 157

[1α,4aα, 7β, 8β(2S*, 4S*), 8aβ]]-2,2-Dimethylbutanoic acid, 3-(cyclopentylsulfinyl)decahydro-7-methyl-8-[2-(tetrahydro-4-hydroxy-6-oxo-2H-pyran-2-yl]ethyl]-1-naphthalenyl ester This example was prepared by following the procedures of Example 11, starting with Example 156 instead of Example 1.

TLC: R$_f$=0.29 (silica gel; 50% ethyl acetate/50% hexane, eluted twice); developed using phosphomolybdate.

EXAMPLES 158 TO 159

These examples were prepared by following the procedures of Examples 13 (oxidation) and 143 and 144 (chromatographic separation and salt formation, starting with Example 157 rather than Example 11.

158. [1S-[1α(βS*,ΔS*),2α,4aβ,6β, 8β, 8aα]]-6-(Cyclopentylsulfinyl)-8-(2,2-dimethyl-1-oxobutoxy)-decahydro-β, Δ-dihydroxy-2-methyl-1-naphthaleneheptanoic acid, major isomer, monolithium salt TLC: R$_f$=0.49 (silica gel; 80% methylene chloride/10% acetic acid/10% methanol; developed using phosphomolybdate.

Microanalysis calculated for $C_{29}H_{49}LiO_7S.1H_2O$ (MW 566.68): required: C, 61.47; H, 9.07; S, 5.66; found: C, 61.64; H, 9. 38; S, 5.44.

IR (KBr pellet): 3431 cm$^{-1}$ (OH), 1718 cm$^{-1}$ (C=O) Mass spectroscopy: m/z 549 (M+Li)+, 543 (M+H)+ and 541 (M−H)−

159. [1S-[1α(βS*,ΔS*),2α,4aβ,6β, 8β, 8aα]]-8-(2,2-Dimethyl-1-oxobutoxy)decahydro-β, Δ-dihydroxy-6-[(2-hydroxyethyl)sulfonyl]-2-methyl-1-naphthaleneheptanoic acid, minor isomer, monolithium salt TLC: R$_f$=0.43 (silica gel; 80% methylene chloride/10% acetic acid/10% methanol; developed using phosphomolybdate Microanalysis calculated for $C_{29}H_{49}LiO_7S$ 1.5H$_2$O (MW 575.68): required: C, 60.50; H, 9.10; S, 5.57 found: C, 60.67; H, 9.14; S, 5.41.

IR (KBr pellet): 3432 cm$^{-1}$ (OH), 1719 (C=O) Mass spectroscopy: m/z 555 (M−H+2Li)+, 549 (M+Li)+, 543 (M+H)+ and 541 (M−H)−

EXAMPLES 160 AND 161

These examples may be prepared by following the procedures of Examples 158 and 159, but starting with Example 141.

160. [1S-[1α(βS*, ΔS*), 2α,4aβ, 6β, 8β, 8aα]]-8-(2,2-Dimethyl-1-oxobutoxy)decahydro-βΔ-dihydroxy-2-methyl-6-[(2-methylpropyl)sulfinyl]-1-naphthaleneheptanoic acid, minor isomer, monolithium salt 161. [1S-[1α(βS*, ΔS*), 2α,4aβ, 6β, 8β, 8aα]]-8-(2,2-Dimethyl-1-oxobutoxy)decahydro-βΔ-dihydroxy-2-methyl-6-[(2-methylpropyl)sulfinyl]-1-naphthaleneheptanoic acid, major isomer, monolithium salt TLC: R$_f$=0.34 (silica gel; 80% methylene chloride/10% acetic acid/10% methanol; developed using phosphomolybdate Microanalysis calculated for Example 161: $C_{28}H_{49}LiO_8S.2.1H_2O$ (MW 574.47): required: C, 58.54; H, 9.33; S, 5.58, found: C, 58.54; H, 9.14; S, 5.82.

IR (KBr pellet): 3439 cm$^{-1}$ (OH), 1705 cm$^{-1}$ (C=O) Mass spectroscopy: m/z 531 (M+H)+, 537 (M+Li)+ and 529 (M−Li)−

What is claimed is:

1. A compound of the formula

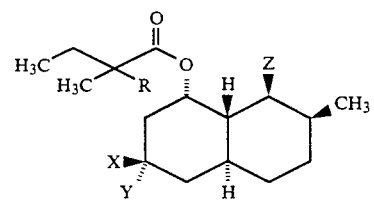

and pharmaceutically acceptable salts thereof, wherein:
X is hydrogen or —S(O)$_m$—R$^1$ and Y is hydrogen or S(O)$_n$—R$^2$, except that X and Y are not both hydrogen, or one of X and Y is —S—alkylene—SH and the other is hydrogen;

Z is 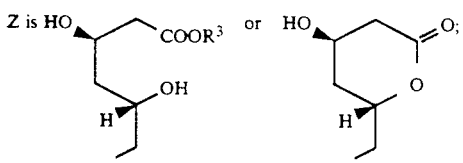

R is hydrogen, alkyl, cycloalkyl, aryl, or aralkyl;

$R^1$ and $R^2$ are each independently hydrogen, acyl, alkyl, alkenyl, alkynyl, aryl, aralkyl, alkaryl, cycloalkyl,

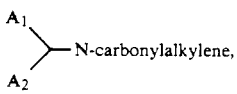

alkoxycarbonylalkylene, any of which is optionally substituted with 1, 2 or 3 hydroxy or halo groups, or $R^1$ and $R^2$ together are alkylene of 1 to 6 carbon atoms;

$R^3$ is hydrogen, alkyl, ammonium, alkylammonium, or alkali metal;

$A_1$ and $A_2$ are each independently hydrogen, alkyl, or alkaryl;

m is 0, 1, or 2;

n is 0, 1, or 2;

"alkyl", "alk-", and "alkylene" refer to groups of 1 to 12 carbon atoms;

"alkenyl" and "alkinyl" refer to groups of 2 to 12 carbon atoms;

"cycloalkyl" refers to cyclic hydrocarbon groups of 3 to 12 carbon atoms; and

"aryl" or "ar-" refers to phenyl; naphthyl; phenyl substituted with 1 to 2 lower alkyl groups, one or two lower alkoxy groups, and/or one to five halogens; and naphthyl substituted with one or two lower alkyl groups, one or two lower alkoxy groups, and/or 1 to 7 halogen atoms.

2. The compound of claim 1, wherein R is hydrogen or alkyl.

3. The compound of claim 1, wherein R is methyl.

4. The compound of claim 1, wherein at least one of $S(O)_n$—$R^1$ and $S(O)_m$—$R^2$ is $C_{1-4}$ alkylthio, $C_{1-4}$ alkylsulfinyl, $C_{1-4}$ alkylsulfonyl, phenylthio, phenylsulfinyl, phenylsulfonyl, or mercapto.

5. The compound of claim 1 wherein both $S(O)_n$—$R^1$ and $S(O)_m$—$R^2$ are alkylthio, arylthio, alkylsulfinyl, arylsulfinyl, alkylsulfonyl or arylsulfonyl.

6. The compound of claim 1, wherein $S(O)_n$—$R^1$ and $S(O)_m$—$R^2$ are, together with the carbon atom to which they are attached, are

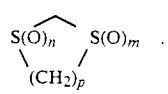

wherein p is 2, 3 or 4.

7. The compound of claim 1, wherein Z is

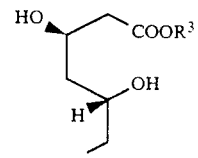

and $R^3$ is hydrogen or alkali metal.

8. The compound of claim 1, wherein Z is

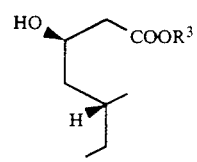

and $R^3$ is lithium.

9. The compounds of claim 1 selected from the group consisting of:

[1S-[1α,4aα,7β, 8β(2S*,4S*),8aβ]]-2,2-dimethylbutanoic acid, 3,3-bis(methylthio)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 8β, 8aα]]-8-(2,2-dimethyl-1-oxobutoxy)decahydro-β,Δ-dihydroxy-2-methyl-6,6-bis(methylthio)-1-naphthaleneheptanoic acid, monolithium salt;

[1S-[1α,4aα,7β, 8β(2S*,4S*),8aβ]]-2,2-Dimethylbutanoic acid, 3-spiro(1,3-dithiolanyl)decahydro-7-methyl-8-[2-(tetrahydro-4-hydroxy-6-oxo-2H-pyran-2-yl)ethyl]-1-naphthalenyl ester;

[1′S-[1′α(βS*, ΔS*), 2′α, 4α′β, 8′β, 8a′α]]-8′-(2,2-dimethyl-1-oxobutoxy)octahydro-β, Δ-dihydroxy-2′-methylspiro[1,3-dithiolane-2,6′(2′H)-naphthalene]-1′-heptanoic acid, monolithium salt;

[1S-[1α,4aα,7β, 8β(2S*,4S*),8aβ]]-2,2-dimethylbutanoic acid, 3,3-bis(propylthio)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 8β(R*), 8aα]]-8-(2,2-dimethyl-1-oxobutoxy)decahydro-β,Δ-dihydroxy-2-methyl-6,6-bis(propylthio)-1-naphthaleneheptanoic acid, monolithium salt;

[1S-[1α,4aα,7β, 8β(2S*,4S*),8aβ]]-2,2-dimethylbutanoic acid, 7-methyldecahydro-3-(methylsulfinyl)-3-(methylthio)-8-[2-(tetrahydro-4-hydroxy-6-oxo-2H-pyran-2-yl)ethyl]-1-naphthalenyl ester;

[1S-[1α(βS*, ΔS*), 2α,4aβ, 8β, 8aα]]-8-(2,2-dimethyl-1-oxobutoxy)decahydro-β,Δ-dihydroxy-2-methyl-6-(methylsulfinyl)-6-(methylthio)-1-naphthaleneheptanoic acid, monolithium salt;

[1S-[1α,4aα,7β, 8β(2S*,4S*),8aβ]]-2,2-dimethylbutanoic acid, 3,3-bis(methylsulfonyl)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 8β, 8aα]]-8-(2,2-dimethyl-1-oxobutoxy)decahydro-β,Δ-dihydroxy-2-methyl-6,6-bis(methylsulfonyl)-1-naphthaleneheptanoic acid, monolithium salt;

[1S-[1α,3α,4aα,7β, 8β(2S*,4S*),8aβ]]-2,2-dimethylbutanoic acid, 7-(methyldecahydro-3-(methylthio)-8-[2-(tetrahydro-4-hydroxy-6-oxo-2H-pyran-2-yl)ethyl]-1-naphthalenyl ester;

[1S-[1α(βS*, ΔS*), 2α,4aβ, 8β, 8aα]]-8-(2,2-dimethyl-1-oxobutoxy)decahydro-β,Δ-dihydroxy-2-methyl-6-(methylthio)-1-naphthaleneheptanoic acid, monolithium salt;

[1S-[1α,3α,4aα,7β, 8β(2S*,4S*),8aβ]]-2,2-dimethylbutanoic acid, 7-methyldecahydro-3-(methylsulfinyl)-8-[2-(tetrahydro-4-hydroxy-6-oxo-2H-pyran-2-yl)ethyl]-1-naphthalenyl ester;

[1S-[1α(βS*, ΔS*), 2α,4aβ, 8β, 8aα]]-8-(2,2-dimethyl-1-oxobutoxy)decahydro-β,Δ-dihydroxy-2-methyl-6-(methylsulfinyl)-1-naphthaleneheptanoic acid, monolithium salt;

[1S-[1α,4aα,7β, 8β(2S*,4S*),8aβ]]-2,2-dimethylbutanoic acid, 7-methyldecahydro-3-(methylsulfonyl)-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)decahydro-β,Δ-dihydroxy-2-methyl-6-(methylsulfonyl)-1-naphthaleneheptanoic acid, monolithium salt;

[1S-[1α,4aα,7β, 8β(2S*,4S*),8aβ]]-2,2-dimethylbutanoic acid, 3,3-bis(phenylthio)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 8β, 8aα]]-8-(2,2-dimethyl-1-oxobutoxy)decahydro-β,Δ-dihydroxy-2-methyl-6,6-bis(phenylthio)-1-naphthaleneheptanoic acid, monolithium salt;

[1S-[1α, 3α,4aα,7β, 8β(2S*,4S*),8aβ]]-2,2-dimethylbutanoic acid, 7-methyldecahydro-3-(phenylthio)-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)decahydro-β,Δ-dihydroxy-2-methyl-6-(phenylthio)-1-naphthaleneheptanoic acid, monolithium salt;

[1S-[1α,3α,4aα,7β, 8β(2S*,4S*),8aβ]]-2,2-dimethylbutanoic acid, 7-methyldecahydro-3-(phenylsulfinyl)-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)decahydro-β,Δ-dihydroxy-2-methyl-6-(phenylsulfinyl)-1-naphthaleneheptanoic acid, monolithium salt;

[1S-[1α,3α,4aα,7β, 8β(2S*,4S*),8aβ]]-2,2-dimethylbutanoic acid, 7-methyldecahydro-3-(phenylsulfonyl)-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)decahydro-β,Δ-dihydroxy-2-methyl-6-(phenylsulfonyl)-1-naphthaleneheptanoic acid, monolithium salt;

[1S-[1α,3α,4aα,7β, 8β(2S*,4S*),8aβ]]-2,2-dimethylbutanoic acid, 3-(acetylthio)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)decahydro-β,Δ-dihydroxy-6-mercapto-2-methyl-1-naphthaleneheptanoic acid, monosodium salt;

[1S-[1α,3α,4aα,7β, 8β(2S*,4S*),8aβ]]-2,2-dimethylbutanoic acid, 3,3-bis(ethylthio)decahydro-7-methyl-8-[2-(tetrahydro-4-hydroxy-6-oxo-2H-pyran-2-yl)ethyl]-1-naphthalenyl ester;

[1S-[1α,3α,4aα,7β, 8β(2S*,4S*),8aβ]]-2,2-dimethylbutanoic acid, 3-(ethylthio)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)-6-(ethylthio)decahydro-β,Δ-dihydroxy-2-methyl-1-naphthaleneheptanoic acid, monolithium salt;

[1S-[1α,4aα,7β, 8β(2S*,4S*)8aβ]]-2,2-dimethylbutanoic acid, 3,3-[1,2-ethanediylbis(sulfonyl)]-decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)-6,6-[1,2-ethanediylbis(sulfonyl)]decahydro-β,Δ-dihydroxy-2-methyl-1-naphthaleneheptanoic acid, monolithium salt;

[1S-[1α,3α,4aα,7β, 8β(2S*,4S*),8aβ]]-2,2-dimethylbutanoic acid, 3-(ethylsulfinyl)decahydro-7-methyl-8-[2-(tetrahydro-4-hydroxy-6-oxo-2H-pyran-2-yl)ethyl]-1-naphthalenyl ester, (R)-sulfur;

[1S-[1α,3α,4aα,7β, 8β(2S*,4S*),8aβ]]-2,2-dimethylbutanoic acid, 3-(ethylsulfinyl)decahydro-7-methyl-8-[2-(tetrahydro-4-hydroxy-6-oxo-2H-pyran-2-yl)ethyl]-1-naphthalenyl ester, (S)-sulfur;

[1S-[1α(βS*, ΔS*), 2α,4aβ, 6β, 8β, 8aα]]-8-(2,2-dimethyl-1-oxobutoxy)-6-(ethylsulfinyl)-decahydro-β,Δ-dihydroxy-2-methyl-1-naphthaleneheptanoic acid, (R)-sulfur, monolithium salt;

[1S-[1α(βS*, ΔS*), 2α,4aβ, 6β, 8β, 8aα]]-8-(2,2-dimethyl-1-oxobutoxy)-6-(ethylsulfinyl)-decahydro-β,Δ-dihydroxy-2-methyl-1-naphthaleneheptanoic acid, (S)-sulfur, monolithium salt;

[1S-[1α,3α,4aα,7β, 8β(2S*,4S*),8aβ]]-2,2-dimethylbutanoic acid, 3-(ethylsulfonyl)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 6β, 8β, 8aα]]-8-(2,2-dimethyl-1-oxobutoxy)-6-(ethylsulfonyl)decahydro-β,Δ-dihydroxy-2-methyl-1-(naphthalene)-heptanoic acid, monolithium salt;

[1S-[1α,4aα,7β, 8β(2S*,4S*),8aβ]]-2,2-Dimethylbutanoic acid, 3,3-bis(2-propenylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(benzylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(cyclohexylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(cyclopentylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(pentafluorophenylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(2,3,5,6-tetrafluorophenylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(1-methylethylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(3-chloropropylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(hexylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(2-methylbutylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis(methylbutylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis[(2-methoxy-2-oxoethyl)thio]decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3,3-bis[(2-ethoxy-2-oxoethyl)thio]decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2-propenylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(benzylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(cyclohexylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(cyclopentylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(pentafluorophenylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2,3,5,6-tetrafluorophenylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(1-methylethylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(3-chloropropylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(hexylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2-methylbutylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(3-methylbutylthio)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-[2-methoxy-2-oxoethyl)thio]decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-[(2-ethoxy-2-oxoethyl)thio]decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2-propenylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(benzylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(cyclohexylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(cyclopentylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(pentafluorophenylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2,3,5,6-tetrafluorophenylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(1-methylethylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(3-chloropropylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(hexylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2-methylbutylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(3-methylbutylsulfinyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-[(2-methoxy-2-oxoethyl)sulfinyl]decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-[(2-ethoxy-2-oxoethyl)sulfinyl]decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2-propenylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(benzylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(cyclohexylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(cyclopentylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(pentafluorophenylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2,3,5,6-tetrafluorophenylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(1-methylethylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(3-chloropropylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(hexylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(2-methylbutylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-(3-methylbutylsulfonyl)decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-[(2-methoxy-2-oxoethyl)sulfonyl]decahydro-7-methyl-8-[2-(tetrahydro-4-hydroxy-6-oxo-2H-pyran-2-yl)ethyl]-1-naphthalenyl ester;

[1S-[1α,4aα,7β, 8β(2S*,4S*),8aβ]]-2,2-Dimethylbutanoic acid, 3-[(2-ethoxy-2-oxoethyl)sulfinyl]decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(2-propenylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(benzylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(cyclohexylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(cyclopentylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(pentafluorophenylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(2,3,5,6-tetrafluorophenylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(1-methylethylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(3-chloropropylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(hexylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(2-methylbutylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(3-methylbutylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis[(2-methoxy-2-oxoethyl)thio]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6,6-bis(2-ethoxy-2-oxoethyl)thio]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2-propenylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(benzylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(cyclohexylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(cyclopentylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(pentafluorophenylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2,3,5,6-tetrafluorophenylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(methylethylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(3-chloropropylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(hexylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2-methylbutylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2- methyl-6-(3-methylbutylthio)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-[(2-methoxy-2-oxoethyl)thio]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-[(2-ethoxy-2-oxoethyl)thio]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2-propenylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(benzylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(cyclohexylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(cyclopentylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(pentafluorophenylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2,3,5,6-tetrafluorophenylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(1-methylethylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(3-chloropropylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(hexylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2-methylbutylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(3-methylbutylsulfinyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-[(2-methoxy-2-oxoethyl)sulfinyl]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-[(2-ethoxy-2-oxoethyl)sulfinyl]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2-propenylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(benzylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(cyclohexylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(cyclopentylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(pentafluorophenylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2,3,5,6-tetrafluorophenylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(1-methylethylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(3-chloropropylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(hexylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(2-methylbutylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-(3-methylbutylsulfonyl)-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-[(2-methoxy-2-oxoethyl)sulfonyl]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-[(2-ethoxy-2-oxoethyl)sulfonyl]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-6-[(2-methylpropyl)thio]-1-naphthaleneheptanoic acid, monolithium salt;

[1S-[1α(βS*, ΔS*), 2α,4aβ, 8β, 8aα]]-8-(2,2-dimethyl-1-oxobutoxy)decahydro-β, Δ-dihydroxy-2-methyl-1-naphthaleneheptanoic acid, monolithium salt;

[1S-[1α(βS*, ΔS*), 2α,4aβ, 6β(S*), 8β,8aα]]-8-(2,2-dimethyl-1-oxobutoxy)-6-[(fluoromethyl)sulphinyl]decahydro-β, Δ-dihydroxy-2-methyl-1-naphthaleneheptanoic acid, monolithium salt, minor isomer;

[1S-[1α(βS*, ΔS*), 2α,4aβ, 6β(R*), 8β,8aα]]-8-(2,2-dimethyl-1-oxobutoxy)-6-[(fluoromethyl)sulphinyl]decahydro-β, Δ-dihydroxy-2-methyl-1-naphthaleneheptanoic acid, monolithium salt;

[1S-[1α(βS*, ΔS*, 2α,4aβ, 6β(R*), 8β,8aα]]-8-(2,2-dimethyl-1-oxobutoxy)decahydro-β, Δ-dihydroxy-2-methyl-6-methylsulfinyl)-1-naphthaleneheptanoic acid, monolithium salt;

[1S-[1α(βS*, ΔS*), 2α,4aβ, 6β(S*), 8β,8aα]]-8-(2,2-dimethyl-1-oxopropoxy)decahydro-β, Δ-dihydroxy-2-methyl-6-(methylsulfinyl)-1-naphthaleneheptanoic acid, monolithium salt,

[1S-[1α,4aα, 7β, 8β(2S*, 4S*), 8aβ]]-2-methylbutanoic acid, 3,3-bis(methylthio)decahydro-7-methyl-8-[2-(tetrahydro-4-hydroxy-6-oxo-2H-pyran-2-yl)ethyl]-1-naphthalenyl ester;

[1S-[1α(βS*, ΔS*), 2α, 3aβ, 8aα]]-8-(2,2-dimethyl-1-oxopropoxy)decahydro-β, Δ-dihydroxy-6,6-bis[(2-hydroxyethyl)thio]-2-methyl-6-(methylsulfinyl)-1-naphthaleneheptanoic acid, monolithium salt;

[1S-[1α(βS*, ΔS*), 2α,4aβ, 6β,8aα]]-8-(2,2-dimethyl-1-oxopropoxy)decahydro-β, Δ-dihydroxy-6-(2-hydroxyethyl)thio]-2-methyl-6-(methylsulfinyl)-1-naphthaleneheptanoic acid, monolithium salt;

[1S-[1α(βS*, ΔS*), 2α,4aβ,6β, 8aα(R*),8aα]]-decahydro-β, Δ-dihydroxy-2-methyl-8-(2-methyl-1-oxobutoxy)-6-(methylsulfinyl)-1-naphthaleneheptanoic acid, monolithium salt;

[1S-[1α(βS*, ΔS*), 2α,4aβ, 6β,8aα]]-8-(2,2-dimethyl-1-oxopropoxy)decahydro-β, Δ-dihydroxy-2-methyl-6-[(2-methylpropyl)sulfonyl]-1-naphthaleneheptanoic acid, monolithium salt;

[1S-[1α(βS*, ΔS*), 2α,4aβ,6β, 8β, 8aα]]-8-(2,2-dimethyl-1-oxobutoxy)-6-[(fluoromethyl)sulfonyl]-decahydro-β, Δ-dihydroxy-2-methyl-1-naphthaleneheptanoic acid, monolithium salt;

[1S-[1α(βS*, ΔS*), 2α,4aβ,6β, 8β(R*),8aα]]-decahydro-β, Δ-dihydroxy-2-methyl-8-(2-methyl-1-oxobutoxy)-6-(methylsulfonyl)-1-naphthaleneheptanoic acid, monolithium salt;

[1S-[1α(βS*, ΔS*), 2α,4aβ,6β, 8β, 8aα]]-8-(2,2-dimethyl-1-oxobutoxy)decahydro-β, Δ-dihydroxy-6-[(2-hydroxyethyl)sulfonyl]-2-methyl-1-naphthaleneheptanoic acid, monolithium salt;

[1S-[1α,4aα, 7β, 8β(2S*, 4S*), 8aβ]]-2,2-dimethylbutanoic acid, 3,3-bis(cyclopentylsulfinyl)decahydro-7-methyl-8-[2-(tetrahydro-4-hydroxy-6-oxo-2H-pyran-2-yl]ethyl]-1-naphthalenyl ester;

[1S-[1α,4aα, 7β, 8β(2S*, 4S*), 8aβ]]-2,2-dimethylbutanoic acid, 3-(cyclopentylsulfinyl)decahydro-7-methyl-8-[2-(tetrahydro-4-hydroxy-6-oxo-2H-pyran-2-yl]ethyl]-1-naphthalenyl ester;

[1S-[1α, (βS*, ΔS*), 2α,4aβ, 6β, 8β, 8aα]]-6-(cyclopentylsulfinyl)-8-(2,2-dimethyl-1-oxobutoxy)-decahydro-β, Δ-dihydroxy-2-methyl-1-naphthaleneheptanoic acid, major isomer, monolithium salt;

[1S-[1α, (βS*, ΔS*), 2α,4aβ, 6β, 8β, 8aα]]-6-(cyclopentylsulfinyl)-8-(2,2-dimethyl-1-oxobutoxy)-decahydro-β, Δ-dihydroxy-2-methyl-1-naphthaleneheptanoic acid, minor isomer, monolithium salt;

[1S-[1α, (βS*, ΔS*), 2α,4aβ, 6β, 8β, 8aα]]-8-(2,2-dimethyl-1-oxobutoxy)decahydro-β, Δ-dihydroxy-2-methyl-6-[(2-methylpropyl)sulfinyl]-1-naphthaleneheptanoic acid, minor isomer, monolithium salt; and

[1S-[1α, (βS*, ΔS*), 2α,4aβ, 6β, 8β, 8aα]]-8-(2,2-dimethyl-1-oxobutoxy)decahydro-β, Δ-dihydroxy-2-methyl-6-[(2-methylpropyl)sulfinyl]-1-naphthaleneheptanoic acid, major isomer, monolithium salt.

10. A method of inhibiting or treating hypercholesterolemia which comprises administering to a patient in need of such treatment an effective amount of a compound as defined in claim 1.

11. A method of inhibiting or treating atherosclerosis, which comprises administering to a patient in need of such treatment an effective amount of a compound as defined in claim 1.

12. A hypocholesterolemic or hypolipidemic composition comprising a compound as defined in claim 1 and a pharmaceutically acceptable carrier therefor.

13. A method of inhibiting cholesterol biosynthesis, which comprises administering to a patient in need of such treatment a cholesterol biosynthesis-inhibiting amount of a compound as defined in claim 1.

14. A combination comprising a compound as defined in claim 1 and an antihyperlipoproteinemic agent.

15. The combination as defined in claim 15 wherein the antihyperlipoproteinemic agent is probucol, gemfibrozil, a bile acid sequestrant, clofibrate, nicotinic acid, neomycin, p-aminosalicylic acid or benzafibrate.

16. A compound of the formula

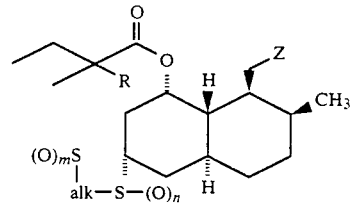

and pharmaceutically acceptable salts thereof, wherein:
alk is alkylene;

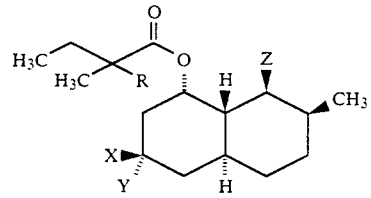

R is hydrogen, alkyl, cycloalkyl, aryl, or aralkyl;
$R^3$ is hydrogen, alkyl, ammonium, alkylammonium, or alkali metal;
m is 0, 1, or 2;
n is 0, 1, or 2;
"alkyl", "alk-", and "alkylene" refer to groups of 1 to 12 carbon atoms;
"cycloalkyl" refers to cyclic hydrocarbon groups of 3 to 12 carbon atoms; and
"aryl" or "ar-" refers to phenyl; naphthyl; phenyl substituted with 1 to 2 lower alkyl groups, one or two lower alkoxy groups, and/or one to five halogens; and naphthyl substituted with one or two lower alkyl groups, one or two lower alkoxy groups, and/or 1 to 7 halogen atoms.

* * * * *